(12) United States Patent
Kendall

(10) Patent No.: US 8,052,633 B2
(45) Date of Patent: Nov. 8, 2011

(54) DELIVERY DEVICE

(76) Inventor: Mark Anthony Fernance Kendall, Chelmer (AU)

( * ) Notice: Subject to any disclaimer, the term of this patent is extended or adjusted under 35 U.S.C. 154(b) by 1154 days.

(21) Appl. No.: 11/496,053

(22) Filed: Jul. 27, 2006

(65) Prior Publication Data

US 2011/0245776 A1   Oct. 6, 2011

Related U.S. Application Data

(63) Continuation-in-part of application No. PCT/GB2005/000336, filed on Jan. 31, 2005.

(30) Foreign Application Priority Data

Jan. 30, 2004 (GB) .................................. 0402131.7

(51) Int. Cl.
*A61N 1/30* (2006.01)
(52) U.S. Cl. .......................................................... 604/19
(58) Field of Classification Search .................. None
See application file for complete search history.

(56) References Cited

U.S. PATENT DOCUMENTS

| | | | |
|---|---|---|---|
| 5,457,041 A | 10/1995 | Ginaven et al. | |
| 5,859,937 A * | 1/1999 | Nomura | 385/12 |
| 6,503,231 B1 | 1/2003 | Prausnitz et al. | |
| 6,558,361 B1 * | 5/2003 | Yeshurun | 604/272 |
| 7,250,037 B2 * | 7/2007 | Shermer et al. | 604/134 |

FOREIGN PATENT DOCUMENTS

| | | |
|---|---|---|
| WO | WO 00/05339 * | 2/2000 |
| WO | WO 02/064193 A2 | 8/2002 |
| WO | WO 02/100476 A2 | 12/2002 |
| WO | WO 2004/000389 A2 | 12/2003 |
| WO | WO 2005/069736 A2 | 8/2005 |
| WO | WO 2005/072630 A1 | 8/2005 |

OTHER PUBLICATIONS

Widera et al, Effect of delivery parameters on immunization to ovalbumin following intracutaneous administration by a coated microneedle array patch system, Vaccine 24 (2006), 1653-1664.
International Preliminary Report on Patentability for International Application No. PCT/GB2005/000336, Jun. 7, 2006 (10 pages).

* cited by examiner

*Primary Examiner* — Ann Lam
(74) *Attorney, Agent, or Firm* — Steven M. Jensen; Edwards Angell Palmer & Dodge LLP

(57) ABSTRACT

A device for delivery of material or stimulus to targets within a body to produce a desired response, the targets being at least one of cells of interest, cell organelles of interest and cell nuclei of interest. The device includes a number of projections for penetrating a body surface, with the number of projections being selected to produce a desired response, and the number being at least 500. A spacing between projections is also at least partially determined based on an arrangement of the targets within the body.

52 Claims, 28 Drawing Sheets

Fig. 9B
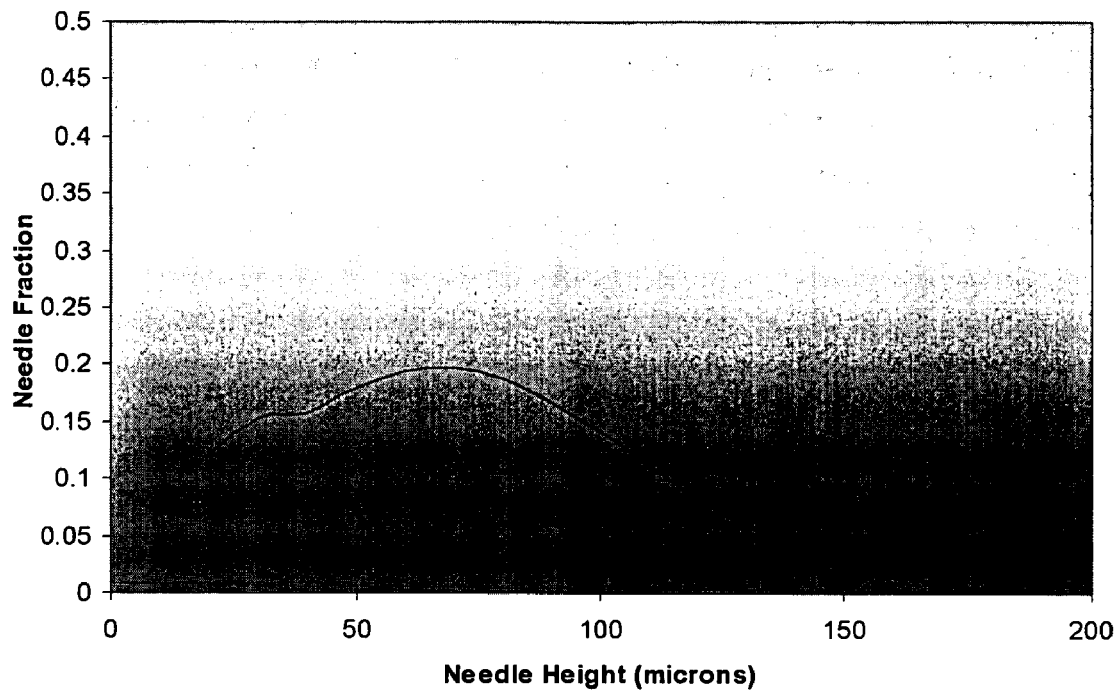
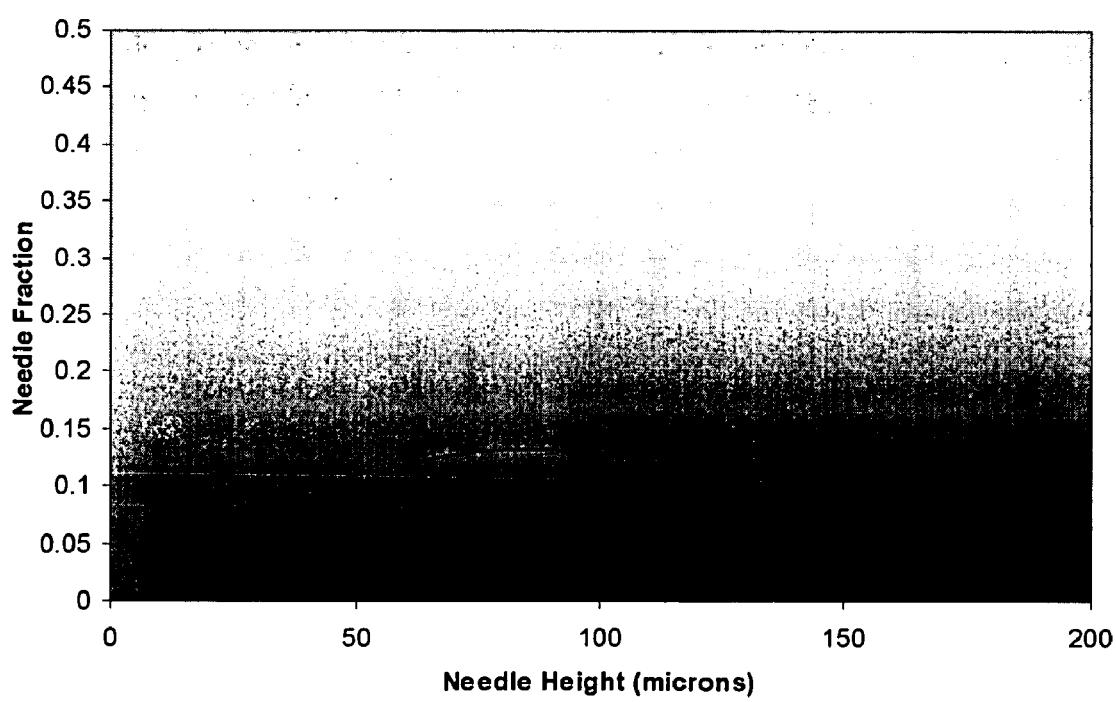
Fig. 9C

DELIVERY DEVICE

CROSS-REFERENCE TO RELATED CASE

The current application is a continuation-in-part (CIP) of International Application Number PCT/GB2005/000336 which designates the U.S. and has an International Filing Date of 31 Jan. 2005 and which was published as International Publication No. WO2005/072630 on 11 Aug. 2005. The entirety of International Application Number PCT/GB2005/000336 is hereby incorporated herein by reference.

BACKGROUND OF THE INVENTION

The present invention relates to a device for delivery of material or stimulus to targets within a body to produce a desired response, and in particular to a device including a number of projections for penetrating a body surface. The invention can also relate to devices for delivering bioactive substances and other stimuli to living cells, to methods of manufacture of the device and to various uses of the device.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

In recent years, attempts have been made to devise new methods of delivering drugs and other bioactive materials, for vaccination and other purposes, which provide alternatives that are more convenient and/or enhanced in performance to the customary routes of administration such as intramuscular and intradermal injection. Limitations of intradermal injection include: cross-contamination through needle-stick injuries in health workers; injection phobia from a needle and syringe; and most importantly, as a result of its comparatively large scale and method of administration, the needle and syringe cannot target key cells in the outer skin layers (FIG. 11 (a)). This is a serious limitation to many existing and emerging strategies for the prevention, treatment and monitoring of a range of untreatable diseases.

The skin structure is shown in FIG. 11, with a summary of key existing delivery methods. Non-invasive methods of delivery through the skin have been used, including patches, liquid solutions and creams. Their success is dependant upon the ability to breach the semi-permeable stratum corneum (SC) into the viable epidermis. Typically, larger biomolecules are unable to breach this barrier.

Alternatively, there are many more "invasive" means to breach the SC for pharmaceutical delivery to the viable epidermis. Simple methods include: tape stripping with an abrasive tape or sandpaper and the application of depilatory agents. Amongst the more advanced technologies are electroporation, ablation by laser or heat, radiofrequency high voltage currents, iontophoresis, liposomes, sonophoresis. Many of these approaches remain untested for complex entities such as vaccines and immunotherapies. Moreover, they do not specifically deliver entities within key skin cells.

Needle-free injection approaches include the high-speed liquid jet injector, which had a rise and fall in popularity in the mid twentieth century—and has recently seen a resurgence (Furth, P. A., Shamay, A. & Henninghausen, L. (1995) Gene transfer into mammalian cells by jet injection. *Hybridoma*, 14:149-152.). However, this method delivers jets of liquid to the epidermis and dermis (labelled (c) in Fig A), usually with a diameter >100 µm and not within key cells. Furthermore, as a result of the concentrated jet momentum, many skin cells die. Delivery into the dermis also leads to patients reporting pain from injection.

The ballistic, needle-free delivery of microparticles (or gene gun) offers a route for delivering biological agents directly into cells of the skin. In this needle-free technique, pharmaceutical or immunomodulatory agents, formulated as or coated to particles, are accelerated in a high-speed gas jet at sufficient momentum to penetrate the skin (or mucosal) layer and to achieve a pharmacological effect. A schematic of microparticles in the skin following ballistic delivery is shown in FIG. 11(b). The ability of this "scatter gun" approach to deliver genes and drugs to epidermal cells is highly limited and sensitive to biological variability in skin properties on the dynamic high strain rate ballistics process. These effects are discussed in Kendall, M. A. F., Rishworth, S., Carter, F. V. & Mitchell, T. J. (2004) "The effects of relative humidity and ambient temperature on the ballistic delivery of micro-particles into excised porcine skin." *J. Investigative Dermatology*, 122(3):739-746); and Kendall, M. A. F., Mitchell, T. J. & Wrighton-Smith, P. (2004) Intradermal ballistic delivery of microparticles into excised human skin for drug and vaccine applications. *J. Biomechanics*, 37(11):1733-1741.

First, the ballistic delivery of particles into the skin to target epidermal cells is extremely sensitive to the small variations in the stratum corneum-including the stratum corneum thickness, which varies massively with body site, age, sex, race and exposure to climatic conditions. (The quasi-static loading of skin with micro-nanostructures would be less sensitive to these differences).

Second, it has been shown that even when all these parameters are strictly controlled—and the only parameter varied is the climatic relative humidity (15%-95%), or, independently, temperature (20° C.-40° C.)—the result is a large variation in penetration depth. These results are shown in FIG. 12, with particle penetration as a function of ambient relative humidity (FIG. 12 (a)) and ambient temperature (FIG. 12 (b)) plotted along with theoretical calculations of particle penetration and measured stratum corneum thickness. This variation alone is significant and sufficient to make the difference between particles breaching the stratum corneum, or not.

The compound effect of these two (and other) sources of variability is the gene gun/biolistics process does not consistently target epidermal cells-leading to inconsistent biological responses (e.g. in DNA vaccination).

Interestingly, it has also been shown that the high strain-rate loading of the skin under ballistic particle impact (approximately $10^6$ per second) increases the stratum corneum breaking stress by up to a factor of 10 compared to quasi-static values-due to a ductile-to-brittle change in the skin mechanical properties. This means that the tissue is more difficult to penetrate as the particle impact velocity is increased. Therefore it is desirable to devise a way to deliver micro/nanostructures to the skin at lower strain-rates than the ballistic approach to exploit the weaker stratum corneum.

When the microparticles are delivered to the skin, it is unclear whether there are any adverse longer term effects. For example, in the case of insoluble particles, many of them slough off with the usual skin turnover. However, gold particles have been detected in the lymph nodes following ballistic particle delivery-presumably by migration with Langerhans cells. Uncertainty of adverse effects of these delivered materials would be removed by delivery routes that do not leave such materials in tissue site.

Moreover, when the microparticles successfully target cells, there is a significant probability they kill the cells they target. Consider a typical ballistic delivery condition: over 1 million 2-3 um diameter gold particles coated in DNA to the skin at 400-600 m/s, over a target diameter of 4 mm (Kendall, M. A. F., Mulholland, W. J., Tirlapur, U. K., Arbuthnott, E. S. & Armitage, M. (2003) Targeted delivery of micro-particles to epithelial cells for immunotherapy and vaccines: an experimental and probabilistic study. *6th International Conference on Cellular Engineering*. Aug. 20-22 2003, Sydney, Australia.). Reported experiments with these conditions using cell death stains (ethidium bromide/acridin orange) show that microparticles impacting the skin do kill cells (McSloy, N. J., Raju, P. A. & Kendall, M. A. F. (2004) The effects of shock waves and particle penetration in skin on cell viability following gene gun delivery. *British Society for Gene Therapy, 1st Annual Conference*. Oxford, UK, Mar. 28-30 2004; Raju, P. A. & Kendall, M. A. F. (2004) Epidermal cell viability following the ballistic delivery of DNA vaccine microparticles. *DNA Vaccines 2004-the Gene Vaccine Conference*. 17-19 Nov. 2004, Monte Carlo, Monaco.).

FIG. 13A shows the percentage of cells that had membrane rupture (i.e. death) as a function of the localised particle channel density. In FIG. 13B we see schematically the way the data in FIG. 13A was achieved, relating "tracks" left by particle penetration to the death of cells in a layer of the viable epidermis. Clearly, FIG. 13A shows that at a channel density above 0.01 channels/micron, all the cells in that layer are dead. Indeed, FIG. 13C shows that cells are killed when the particle is passing up to 10 μm outside of the cell boundary. The mechanism of cell death is due to the propagation of stress and shock waves in the skin generated by the rapid deceleration of the microparticles (McSloy et al. (2004)). The rapid rise time of these stress waves in the skin, and their magnitude both contribute to cell death and the results are consistent with the findings reported by Doukas, A. G. & Flotte, T. J. (1996). Physical characterisation and biological effects of laser-induced stress waves. *Ultrasound in Medicine and Biology*, 22(2):151-164. The effects of shock waves and particle penetration in the skin on cell viability following gene gun delivery. *Masters Thesis*, Department of Engineering Science, University of Oxford.). This mechanism of ballistic particle penetration killing cells negatively affects the ability of the direct and efficient delivery of genes and drugs to the cells.

This cell death effect of ballistic particle delivery could be reduced by significantly decreasing the particle size to the nanometre regime-thereby reducing the stresses on the cells. However, another limitation of the gene gun is that it is unsuitable in delivering sub-micron sized particles to cells. This is illustrated by the following. As reported (Kendall, M. A. F., Mitchell, T. J. & Wrighton-Smith, P. (2004) Intradermal ballistic delivery of micro-particles into excised human skin for drug and vaccine applications. *J Biomechanics*, 37(11): 1733-1741), and shown in FIG. 14, ballistic particle penetration is proportional to the particle impact parameter, ρvr, which is the product of the particle density (ρ), velocity (v) and radius (r). This parameter is also proportional to the particle momentum per-unit-area, which has been shown to drive the mechanism of particle penetration depth (Mitchell et al. (2003)). From FIG. 14, we see a 1 μm radius gold particle (density 18000 kg/m$^3$) would need to impact the skin at ~600 m/s in order to penetrate to reach cells ~20 μm into the skin.

Experimental results show that reducing the particle radius, say, by an order of magnitude, to 100 nm, and placing it in a standard biolistic device leads to negligible particle impact in the skin. Indeed from FIG. 14 we see delivery to a 20 μm depth would need an impact velocity of ~6000 m/s, which is impractical for two reasons: 1) these hypervelocity conditions can not be safely achieved with a system configured for human use (they are usually achieved with massive free-piston shock tunnels); 2) even if 6000 m/s was obtained in the free-jet, a gas impingement region above the skin would seriously decrease the particle velocity—it is possible that the particle would not even hit the skin at all. Interestingly if a method was conceived to safely and practically deliver nanoparticles to the skin at higher velocity (e.g. the stated case of an 100 nm radius gold particle at a velocity of ~6000 m/s), the cell death benefit of smaller scale would be offset by higher peak stresses-killing more cells—and higher strain rates that are likely to further "toughen" the skin, making delivery even more difficult.

In conclusion, these collective facts rule out the gene gun as a viable option for delivering nanoparticles and therefore precludes it from many of the developments in biomolecules, drugs and sensors at this scale.

The huge research effort in micro-and nanotechnologies provides tremendous potential for simple and practical cell targeting strategies to overcome many limitations of current biolistic (and other) cell targeting approaches. For example, FIG. 11(c) shows that the most conceptually simple and appealing approach to gene delivery is the direct injection of naked DNA to live cell nuclei at a sub-micrometre scale that does not adversely damage the cell (Luo, D. & Saltzman, W. M. (2000) Synthetic DNA delivery systems. *Nature Biotechnology*, 18:33-36). Cell death is minimised by both the sub-micrometre scale of the injector and the low, quasi-static strain-rate of the probe (compared to ballistic delivery) resulting in low stress distributions. Although this is a very efficient gene and bioagent delivery route, the drawback is that such precise targeting by direct microinjection can only be achieved one cell at a time and with great difficulty to the operator in vivo. Hence, the method is slow, laborious and impractical.

Researchers have overcome some of these disadvantages for transdermal drug delivery by fabricating arrays of micrometre-scale projections (thousands on a patch) to breach the stratum corneum for the intradermal delivery of antigens and adjuvants to humans and other mammals.

In the scientific literature, the first description of this technique appears to be the paper 'Microfabricated Microneedles: A Novel Approach to Transdermal Drug Delivery. S. Henry et al, J. Pharmaceutical Sci. vol 87(8) p 922-925 (1998), with the accompanying patent of U.S. Pat. No. 6,503,231. The objective of U.S. Pat. No. 6,503,231 is to provide a microneedle array device for relatively painless, controlled, safe, convenient transdermal delivery of a variety of drugs and for biosampling. This is achieved by the microneedles breaching the tissue barrier (e.g. for skin: the stratum corneum) and then the therapeutic or diagnostic material is injected through the hollow microneedles into the tissue. Specifically, in claim 1 of U.S. Pat. No. 6,503,231, it is stated that the microneedles are to be hollow, with a length of 100 μm-1 mm, and claim 3 states the width of 1 μm-100 μm, with subsequent claims stating ways the hollow needles can be connected to reservoirs for the injection of liquids, fabrication methods, materials and examples of drugs to be delivered. Thus, U.S. Pat. No. 6,503, 231 describes a patch suitable for delivering materials and/or energy across tissue barriers. The microneedles are hollow and/or porous to permit drug delivery at clinically relevant rates across skin or other tissue barriers, without damage, pain, or irritation to the tissue.

Other related microneedle devices in the patent literature are U.S. Pat. Nos. 5,527,288 and 5,611,806. More recently published patent applications on this topic are WO02/085446, WO02/085447, WO03/048031, WO03/053258 and WO02/100476A2.

These microneedles array patch technologies have achieved only limited success to date. Generally, there are a range of approaches configured to breach the stratum corneum to allow an enhanced take-up of drug in the viable epidermis. Although this has not been discussed in the patents referred to above, based upon reported research on ballistic particle delivery and cell death; the low strain rate of application, combined with the cases of smaller projections are likely to induce a lower incidence of cell death near the tips, than ballistic microparticle delivery. Also, unlike ballistic microparticle delivery, these projections are removed from the tissue-alleviating the possibility of adverse effects of "carrier" materials delivered to the body, long term.

However, unlike biolistic targeting (FIG. 11(b)), and the direct injection of cells (FIG. 11(c)), these microneedle arrays do not have the advantage of readily and directly targeting inside the skin cells. This cellular/organelle targeting capability is key in a range of existing and potential methods of vaccination, gene therapy, cancer treatment and immunotherapy (Needle-free epidermal powder immunization. Chen et al, Expert Rev. Vaccines 1(3) p 265-276 (2002)) and diagnostic technologies.

Whilst U.S. Pat. No. 5,457,041 describes a patch for targeting cells, this is only suitable for use in vitro, and requires specialised apparatus to direct the micro-needles towards identified cells. The apparatus uses a microscope, to allow an operator to locate the cells in the sample tissue, and then direct the application of the micro-needles appropriately. As a result, this makes the device unsuitable for use in clinical environments, and limits the ability of the device to elicit a desired biological response.

Therefore, there still remains a need to provide projection-based technology which achieves a more accurately directed delivery of the active agent or stimulus to the desired site of action surrounding or within cells, without appreciable damage to them.

SUMMARY OF THE PRESENT INVENTION

In a first broad form the present invention provides a device for delivery of material or stimulus to targets within a body to produce a desired response, the targets being at least one of cells of interest, cell organelles of interest and cell nuclei of interest, the device including a number of projections for penetrating a body surface, and wherein:
 a) the number of projections is selected to produce a desired response, the number being at least 500; and,
 b) a spacing between projections is at least partially determined based on an arrangement of the targets within the body.

Typically the number of projections is selected by:
 a) determining a likelihood of a projection targeting at least one of the targets;
 b) determining a number of targets to be targeted; and,
 c) determining the number of projections using the determined likelihood and the determined number of targets.

Typically the likelihood $P_{contact}$ of a projection targeting a target of interest is at least partially based on:

$$P_{contact} = \frac{V_{tar}}{V_{layer}} \qquad 1$$

ii) where:
 (a) $V_{layer}$ is the volume of the layer containing targets,
 (b) $V_{tar}$ is the volume including the target of interest to which material or stimulus can be delivered.

Typically the number of targets to be targeted depends on the number of targets that need to be transfected to produce the desired response.

Typically the number of targets to be targeted is at least one of:
 a) at least 10;
 b) at least 100;
 c) at least 1000;
 d) at least 10000;
 e) at least 100000;
 f) at least 1000000; and,
 g) at least 10000000.

Typically the number of projections is at least one of:
 a) at least 10;
 b) at least 100;
 c) at least 1000;
 d) at least 10000;
 e) at least 100000;
 f) at least 1000000; and,
 g) at least 10000000.

Typically a maximum number of projections is based on at least one of:
 a) the total surface area of the target site available;
 b) a minimum projection spacing (S); and,
 c) an upper limit in active material or stimulus to be delivered Typically the projection spacing is based at least partially on at least one of:
 a) a size of the targets of interest; and,
 b) a spacing between the targets of interest.

Typically the spacing between at least some of the projections is selected to avoid multiple projections targeting a single target of interest.

Typically the spacing between at least some of the projections is selected to be greater than a diameter of the targets of interest.

Typically the spacing between at least some of the projections is selected to be approximately equal to the spacing between the targets of interest.

Typically the spacing S between at least one of:
 a) $1 \, \mu m \leq S \leq 10000 \, \mu m$; and,
 b) $10 \, \mu m \leq S \leq 200 \, \mu m$.

Typically projection dimensions are based at least partially on an arrangement of targets within the body.

Typically at least some of the projections have a diameter of at least one of:
 a) less than the size of targets; and,
 b) of the order of the size of targets within the targets.

Typically at least some of the projections have a projection length at least partially based on a depth of the targets below a surface of the body against which the device is to be applied in use.

Typically the projections include a support section and a targeting section.

Typically the targeting section has a diameter of less than at least one of:
 a) $1 \, \mu m$; and,
 b) $0.5 \, \mu m$.

Typically a length for the targeting section is at least:
 a) less than $0.5 \, \mu m$; and,
 b) less than $1.0 \, \mu m$; and,
 c) less than $2.0 \, \mu m$.

Typically a length for the support section is at least partially based on a depth of the targets below a surface of the body against which the device is to be applied in use.

Typically the length for the support section is at least partially determined in accordance with properties of a surface of the body against which the device is to be applied in use.

Typically at least one of a support section length and the number of projections is at least partially based on a likelihood of a projection penetrating the targets:

$$P_{depth} = \int_{B-Q\sigma}^{T+B-Q\sigma} \frac{1}{\sigma\sqrt{2\pi}} e^{-\left(\frac{x-D}{\sigma}\right)^2}$$

where:
- (a) $\sigma$ is the standard deviation from a mean location, accounting for the skin surface undulations.
- (b) D is a distance of the targets below a surface of the body against which the device is to be applied in use;
- (c) Q is a number of standard deviations from a mean level of the surface of the body at which the device comes to rest in use;
- (d) B is a length of the support section; and,
- (e) T is a length of a targeting section.

Typically a length for the support section is at least one of:
a) for epidermal delivery <200 μm;
b) for dermal cell delivery <1000 μm;
c) for delivery to basal cells in the epithelium of the mucosa 600-800 μm; and,
d) for lung delivery of the order of 100 μm in this case.

Typically the length of the delivery end section is greater than the target dimension.

Typically at least some of the projections within a targeting configuration have different dimensions.

Typically the projections are solid.

Typically the projections are non-porous and non-hollow.

Typically at least part of at least some of the projections are coated with a bioactive material.

Typically at least part of at least some of the projections are coated with a non-liquid material.

Typically at least part of a targeting section of at least some of the projections are coated.

Typically the coating is at least one of:
a) nanoparticles;
b) a nucleic acid or protein;
c) an antigen, allergen, or adjuvant;
d) parasites, bacteria, viruses, or virus-like particles;
e) quantum dots, SERS tags, raman tags or other nanobiosensors;
f) metals or metallic compounds; and,
g) molecules, elements or compounds.

Typically the device includes at least some uncoated projections to thereby stimulate or perturb the targets in use.

In one example, the device includes:
a) a flexible substrate; and,
b) a number of patches, each patch including a number of projections for penetrating a body surface, the number of patches being mounted to a flexible backing.

In a second broad form the present invention provides a method of selecting constructional features for a device a for delivery of material or stimulus to targets within a body to produce a desired response, the targets being at least one of cells of interest, cell organelles of interest and cell nuclei of interest, the device including a number of projections for penetrating a body surface, and wherein the method includes:

a) selecting the number of projections to produce a desired response, the number being at least 500; and,
b) selecting a spacing between projections at least partially based on an arrangement of the targets within the body.

In a third broad form the present invention provides a method of fabricating a device for delivery of material or stimulus to targets within a body to produce a desired response, the targets being at least one of cells of interest, cell organelles of interest and cell nuclei of interest, the device including a number of projections for penetrating a body surface, and wherein the method includes:

a) selecting the number of projections to produce a desired response, the number being at least 500;
b) selecting a spacing between projections at least partially based on an arrangement of the targets within the body; and,
c) fabricating the device using the selected number of projections, and the selected spacing In a fourth broad form the present invention provides a method of treating a subject the method including using a device for delivery of material or stimulus to targets within the subject's body to produce a desired response, the targets being at least one of cells of interest, cell organelles of interest and cell nuclei of interest, the device including a number of projections for penetrating a body surface, and wherein:

a) the number of projections is selected to produce a desired response, the number being at least 500; and,
b) a spacing between projections is at least partially determined based on an arrangement of the targets within the body.

In a fifth broad form the present invention provides apparatus for delivery of material or stimulus to targets of interest within a body to produce a desired response, the targets being at least one of cells of interest, cell organelles of interest and cell nuclei of interest, the apparatus including:

a) a structure;
b) a plurality of projections movably mounted to the structure for penetrating a body surface;
c) an actuator for selectively releasing the plurality of projections mounted on the movable structure from a retracted position such that upon contact with the body surface the plurality of projections enter the body.

Typically the plurality of projections are provided on a patch.

Typically the actuator includes:
a) a spring coupled to the structure and the at least one patch; and,
b) a releasing means for releasing the spring, to thereby release the plurality of projections from the retracted position.

Typically the releasing means is a tensioned string for holding the spring in compression.

Typically the releasing means is manually operated.

Typically the apparatus includes a number of arms, each arm being coupled to a respective spring and including a first end pivotally mounted to the structure and a second end coupled to a respective plurality of projections, and wherein activation of the releasing means causes each of the arms to be released from a retracted position to thereby cause projections on the respective patch to enter the body.

Typically the arms are circumferentially spaced around a part of the structure.

Typically the structure is flexible structure allowing the structure to be guided to a desired location within the body.

Typically the releasing means includes an inflatable structure coated with the plurality of projections.

Typically:
a) the number of projections is selected to produce a desired response, the number being at least 500; and,
b) a spacing between projections is at least partially determined based on an arrangement of the targets within the body.

BRIEF DESCRIPTION OF THE DRAWINGS

An example of the present invention will now be described with reference to the accompanying drawings, in which:—

FIGS. 9A to 9C show examples of projection viability against the projection height, for variation in the skin surface level standard deviation of 20 μm, 40 μm and 60 μm respectively;

DETAILED DESCRIPTION OF THE PREFERRED EMBODIMENTS

An example of a device for delivering material or stimulus targets within a body will now be described with reference to FIGS. 1A to 1E.

In this example, the device is in the form of patch 100 having a base 120 and a number of projections 110. The base 120 and projections 110 may be formed from any suitable material, as will be described in more detail below, but in one example, are formed from a silicon type material, allowing the device to be fabricated using fabrication processes such as vapour deposition, silicon etching, Deep Reactive Ion Etching (DRIE), or the like.

In the example shown, the device has a width W and a breadth B with the projections 110 being separated by spacing S.

Figure 1A:
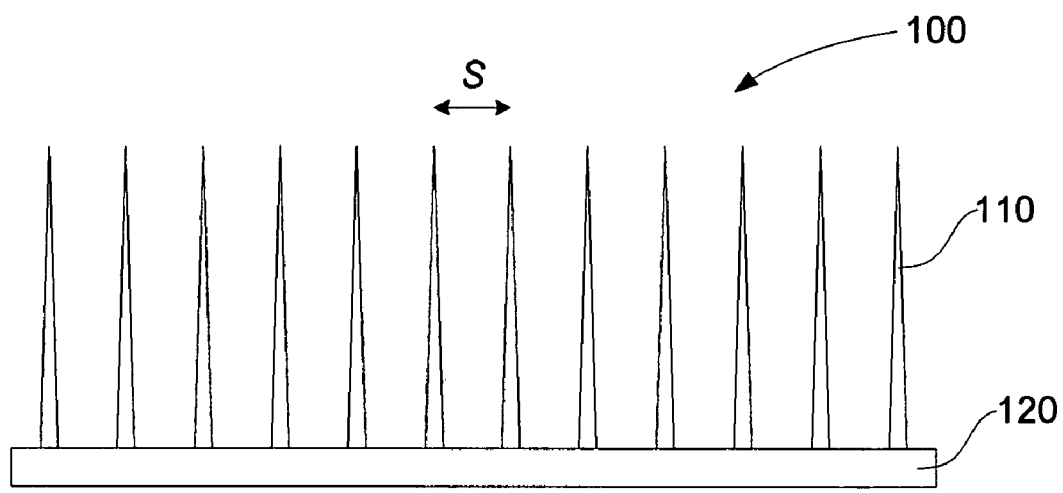
FIGS. 1A and 1B are schematic diagrams of an example of device for delivery of material or stimulus to targets within a body.
Figure 1B:
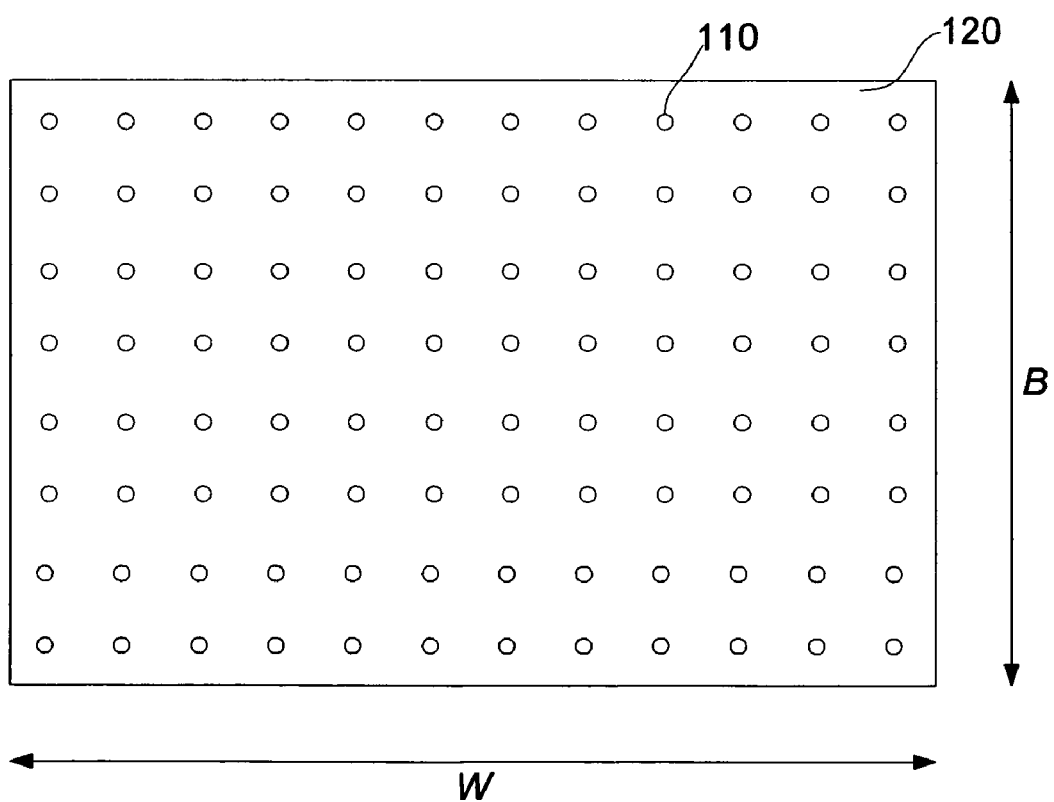
Figure 1C:
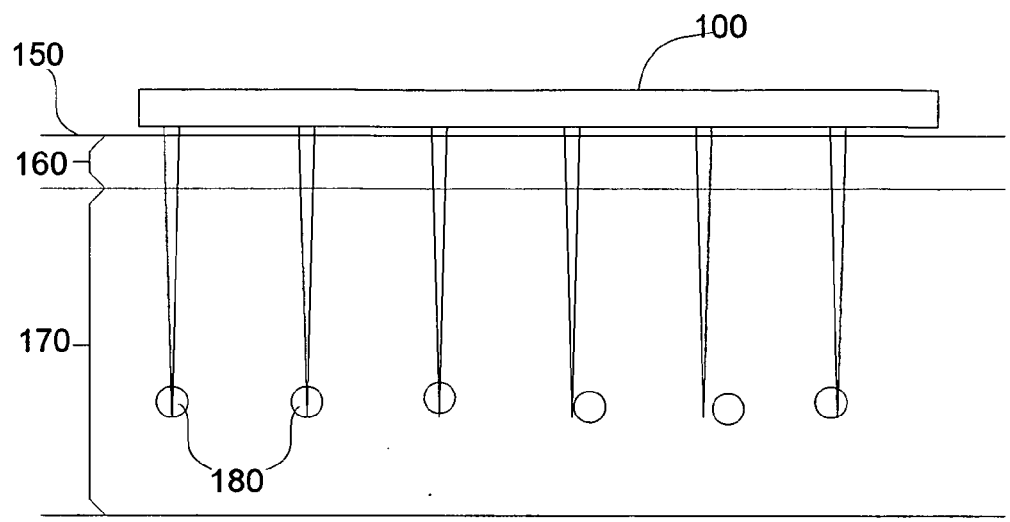
FIG. 1C is a schematic diagram of an example of the device of FIG. 1A in use.

In use, the patch 100 is positioned against a surface of a subject, allowing the projections to enter the surface and provide stimulus or material to targets therein. An example of this is shown in FIG. 1C.

In this example, the patch 100 is urged against a subject's skin shown generally at 150, so that the projections 110 pierce the Stratum Corneum 160, and enter the Viable Epidermis 170 to reach targets of interest, shown generally at 180.

Figure 1D:
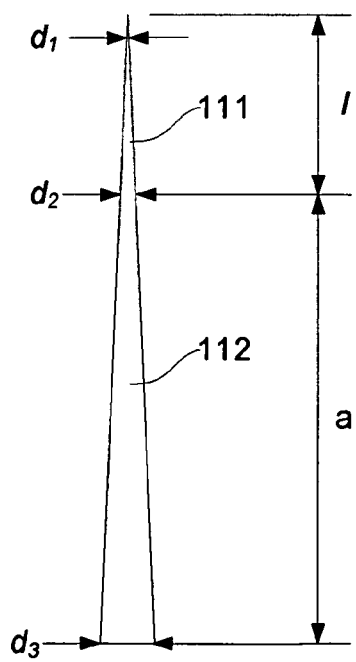
FIGS. 1D and 1E are schematic diagrams of examples of projections used in the device of FIG. 1A.
Figure 1E:
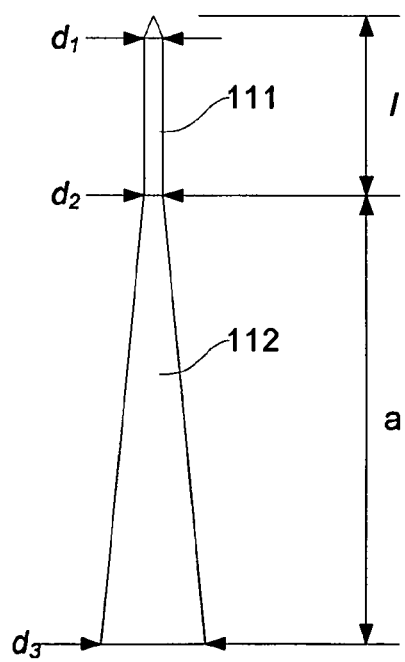

Examples of suitable projections are shown in more detail in FIGS. 1D and 1E.

In each example, the projection generally includes a targeting section 111, intended to deliver the material or stimulus to targets within the body, and a support section 112 for supporting the targeting section 111.

In the example of FIG. 1D, the projection is formed from a conically shaped member, which tapers gradually along its entire length. In this example, the targeting section 111 is therefore defined to be the part of the projection having a diameter of less than $d_2$.

As an alternative example however, the structure of the projection may vary along its length to provide a targeting section 111 with a designed structure. In this example, the targeting section 111 is in the form of a substantially cylindrical shape, such that the diameter $d_1$ is approximately equal to the diameter $d_2$.

In either case, the support section has a length a, whilst the targeting section 111 has a length l. The diameter of the tip is indicated by $d_1$, whilst the diameter of the support section base is given by $d_3$.

In use, the device is intended to deliver material or stimulus to specific targets within the body. Thus, rather than just operating to deliver material to, for example, the blood supply, or tissue within the body, the device is configured so as to ensure material or stimulus reaches specifically selected targets such as cells, cell organelles, cell nuclei, or the like. Furthermore, the device is designed to achieve this without requiring specific directional control of device application so as to ensure the projections reach the targets. In other words, the device is intended to ensure successful delivery of material or stimulus to specific targets within a subject, without requiring that the projections are aimed at the specific targets, but rather by allowing general placement in a suitable region. Thus, for example placement may be as simple as placement anywhere on the user's skin in order to target Langerhans cells of the device on the subject.

Figure 2:
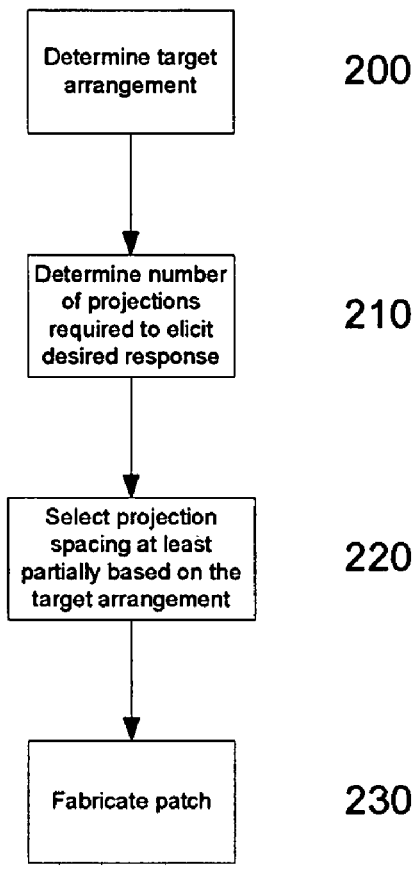
FIG. 2 is a flow chart of an example of the process of selecting device parameters.

To achieve this, the device is provided with a particular configuration to ensure successful targeting. Accordingly, it is generally necessary to select patch parameters, such as the number of projections N, and spacing S between projections, to be dependent upon the intended use of the device. A mechanism for achieving this will now be described with reference to FIG. 2.

In this example, at step 200 it is necessary to determine an arrangement of desired targets. This may be achieved in any one of a number of ways and will depend on the nature of the targets. Thus, for example if the targets are a specific type of cell, cell nuclei, or cell organelle, this information can be determined from literature or studies detailing the typical location of cells, or other targets, within the body.

At step 210 a number of projections required to elicit a desired response is determined. This can depend on a range of factors, such as the ability of projections to reach the desired targets, the ability of the projections to deliver material or stimulus to the targets, as well as the ability of the targets to elicit a response. Thus, for example, non-uniform distribution of targets within the body means that it is not possible to assume that each projection will deliver material or stimulus to a desired target during use of the device.

The number of projections may be determined in any one of a number of ways. Thus, for example, this can include selecting a number of projections from a predetermined list outlining the number of projections required for specific uses. However, if the number has not previously been determined, for example, if the target has not previously been used, then some form of analysis is typically required.

In one example, this is achieved by analysing the distribution of targets within the body and then determining a likelihood of any one projection reaching a target. An indication of the number of targets to which stimulus or material must be delivered can then be used to determine an indication of the number of projections required.

As will be described in more detail below, in general a desired response cannot be obtained with less than 500 projections. More typically at least 750 projections are required. However, in some instances, even more projections such as at least 1000, 2000, 5000, 7500, 10,000, 100,000, 1,000,000 or even 10,000,000 may be used, and specific examples will be described in more detail below.

Once a number of projections has been selected, a projection spacing is determined at least partially based on the target arrangement at step 230.

The spacing may be determined in any one of a number of ways, but typically includes setting a lower spacing limit to ensure that only a single projection delivers material or stimulus to a single target. The maximum spacing S is typically set based on the required patch size (B×W) and/or the spacing between targets. It will be appreciated that whilst the example shown is rectangular, alternative shapes, such as circular, elliptical, hexagonal, or the like, may be used and that the use of a rectangular patch is for the purpose of example only.

At step 240 a patch is fabricated in accordance with the selected patch parameters, including the number of projections N and the spacing S. Fabrication may be achieved in a number of ways, as will be described in more detail below.

By selecting at least a number of projections N required to elicit a desired response, this allows a patch to be provided with sufficient projections to ensure that a desired response is achieved by delivery of material or stimulus to specific targets. Furthermore, by utilising a probabilistic analysis, this technique ensures that the required targeting will be achieved without requiring the individual projections to be aimed at the individual targets. Thus, in contrast to other prior art techniques, the patch 100 may simply be inserted into a body at a general location, and does not need specialised apparatus to direct the projections towards specific cells or other targets within the body.

Figure 3A:
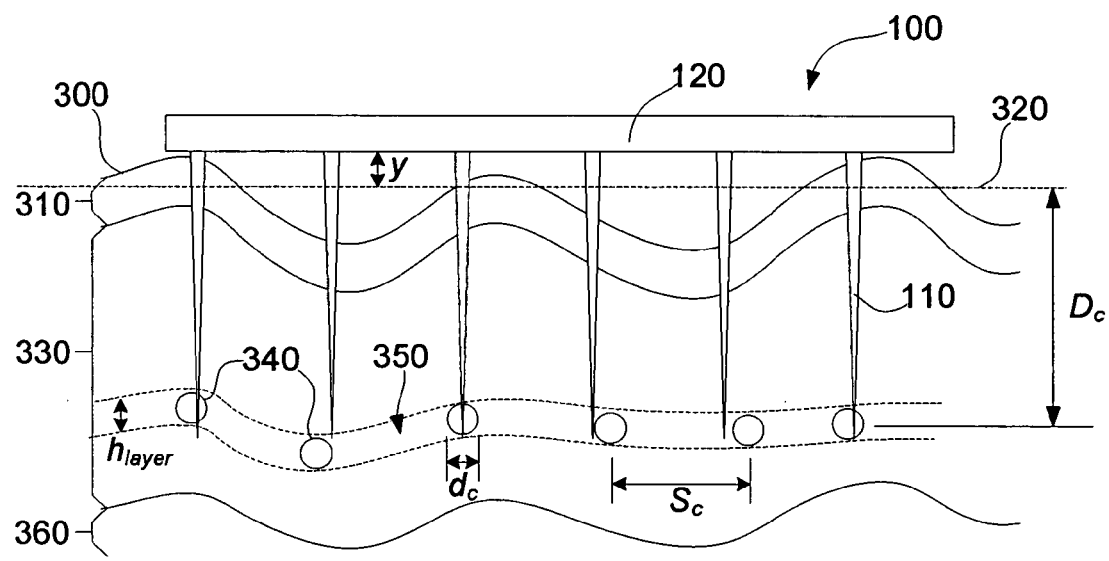
FIGS. 3A and 3B are schematic diagrams of alternative examples of the device of FIG. 1A in use taking into account variations in surface properties and target locations.
Figure 3B:
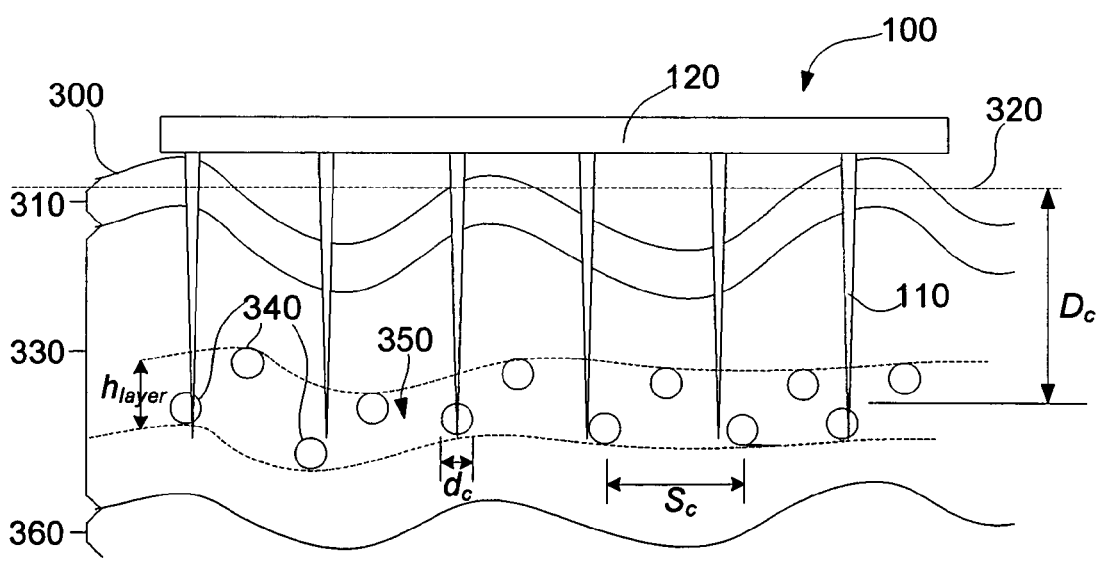

A more detailed example of the process will now be described. For the purpose of this example the patch configuration, and in particular the insertion of the patch into the body is as shown in FIG. 3A and FIG. 3B. In particular, this example is modified to take into account variations and undulations in the surface of the body, as well as variations in target depth.

In this example, the patch 100 is urged against the surface 300 of the Stratum Corneum 310. The surface 300 includes undulations, resulting in a mean surface level 320 shown by dotted lines, with the patch base 120 resting against the surface 300 at a distance y above the mean level 320.

The projections 110 enter the Viable Epidermis 330 to deliver material or stimulus to targets 340, which are generally arranged in a layer 350, referred to as the target layer. The Dermis is also shown at 360 in this example.

In the example of FIG. 3A the targets 340 are provided in a single layer with each target being approximately a constant depth $D_c$ below the Stratum Corneum 310. In this example, the layer height $h_{layer}$ is therefore approximately equal to the diameter of the targets $d_c$, with the targets separated by a spacing $S_c$. It would be appreciated by persons skilled in the art that in this instance the targets may therefore be Langerhans Cells, or the like.

In the example of FIG. 3B, the targets 340 are dispersed vertically through the Viable Epidermis 330, so that the target layer 350 has a greater height $h_{layer}$ than in the previous example. Additionally, in the example, the depth of the targets is calculated on the basis of the mean layer depth, as shown.

Figure 4:
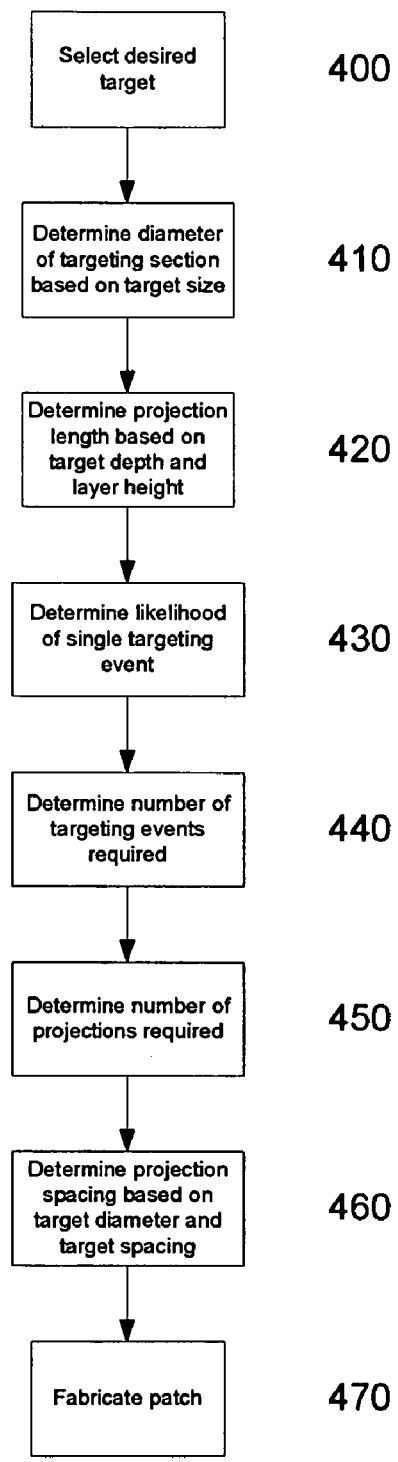
FIG. 4 is a flow chart of a second example of the process of selecting device parameters.

An example of the process for selecting a device configuration to take into account the arrangements in FIGS. 3A and 3B will now be described in more detail with reference to FIG. 4.

At step 400 a desired target and corresponding target arrangement is determined.

The target selected will depend on the intended application. Thus, for example, the target may be cells, cell nuclei or cell organelles. Additionally, different types of cells may need to be targeted. Thus, for example, cells such as Langerhans Cells may be stimulated for providing an immunological response, whereas cells such as squamous or basal cells may need to be targeted to treat cell carcinoma. An example of other potential targets will be described in more detail below.

Determining the target arrangement typically involves determining parameters relating to the target such as target depth $D_c$, target diameter $d_c$, layer height $h_{layer}$ and target spacing $S_c$. Thus these correspond to the parameters outlined above with respect to FIGS. 3A and 3B.

At step 410 the diameter of the targeting section 111 for at least some of the projections is determined.

The diameter of the targeting section is typically based on the size of the target. Thus, for example, the diameter of the targeting section does not usually exceed the scale of the target, as this may lead to target necrosis. In general this leads to an upper limit for targeting section diameters of:

$d_1 \leq 1$ μm and $d_2 \leq 1$ μm.

However, it will be appreciated that smaller diameters such as 500 nm, or below, may be used, as described in specific examples below. Additionally or alternatively, it may be desirable to include projections having a larger diameter, for example to cause cell necrosis. In one example, at least some of the projections have a diameter greater than 1 μm, which can be used to induce bystander responses. In other examples, all of the projections have a diameter greater than 1 μm to thereby kill targets.

At step 420 the projection length is determined. In one example, the projection length is based on the depth of the target layer $D_c$ and the layer height $h_{layer}$. Thus, the length of the supporting section of a can be selected so that the targeting section 111 at least reaches the target layer within the body, but typically does not extend a large distance beyond the target layer. In this example, the length a of the support section 112 is typically given by:

$(D_c + h_{layer}/2) \geq a \geq (D_c - h_{layer}/2)$

Similarly the length l of the targeting section 111 is typically selected to be at least equal to the layer height $h_{layer}$ to ensure penetration of targets within the layer 340, so that:

$l \geq h_{layer}$

As shown in the examples of FIGS. 3A and 3B however the skin of the body is not generally flat but is undulating. As a result, this means that the base 120 of the device 100 generally sits a distance y above the mean skin level 320. To take this into account, the length of the support section 112 may be increased such that:

$(y + D_c + h_{layer}/2) \geq a \geq (y + D_c - h_{layer}/2)$

Alternatively, a probabilistic analysis can be used to determine the likelihood of a viable projection of a given length reaching the targets with the body. This will depend on a number of factors, examples of which, for the targeting of Langerhans cells (LC), include:

The surface of the skin is normally distributed

It is assumed that the LC reside exactly 17 μm below the surface just above the basal layer (Arbuthnott, 2003, Emislom et al, 1995), in the case of the Balb/c mouse ear. In reality, there may be a small variation in depth of LC. For example, the depth of LC varies significantly from site-to-site within a given animal of human model, and there is typically variation in the depth of LC between models—for example the depth of LC in humans is greater than in mice.

The patch typically comes to rest two standard deviations away the mean skin level The needles have a viable tip length of 20 μm (i.e. l, (defined as 111) is 20 μm. Penetration by any other part of the needle other than this tip causes cell death.

The Skins surface is normally distributed with mean 0 and standard deviation σ.

Within the model:

The Langerhans cells lie $D_c$ microns directly below the skins surface.

The patch comes to rest Q standard deviations from the skins mean level.

The needles have body (unviable) length support section a and tip (viable) length l.

In this example, the likelihood of viable targeting of targets at the defined depths ($P_{depth}$) is given by:

$$P_{depth} = \int_{a-Q\sigma}^{l+a-Q\sigma} \frac{dx}{\sigma\sqrt{2\pi}} e^{-\left(\frac{x-D_c}{\sigma}\right)^2} \quad (1)$$

where:
σ is the standard deviation from a mean location, accounting for the skin surface undulations.
$D_c$ is a distance of the cells of interest below a surface of the body against which the device is to be applied in use;
Q is a number of standard deviations from a mean level of the surface of the body at which the device comes to rest in use;
a is a length of the support section; and,
l is a length of a targeting section.

In this example it is assumed that the skin surface level is normally distributed on a local scale, which is typically a safe assumption based on histology samples, although if the area inspected is too large global curvature invalidates the assumption. At first instance, it is assumed that the patch comes to rest at a distance y of two standard deviations away from mean skin level.

The use of such a model allows support section and targeting section lengths a, l to be selected to ensure a predetermined probability of the targeting section 111 successfully reaching the targets. In one example, the probability is selected to be one, to ensure successful delivery of the material or stimulus. Alternatively, lower probabilities may be selected, with this being taken into account in determining the number of projections provided, as will be described in more detail below.

At step 430, the likelihood of a single targeting event is determined. In particular, this is the likelihood of a projection, assuming the projection reaches the target layer 350, of delivering material to or stimulus to a respective target 340.

In one example, it is assumed that the targeting section 111 is effectively a point diameter cylinder that extends into the target layer 350. In this instance the likelihood of a single targeting event is given by the volume of the target divided by the volume of the layer.

$$P_{contact} = \frac{V_{tar}}{V_{layer}} \quad (2)$$

where:
$V_{layer}$ is the volume of the layer containing cells of interest,
$V_{tar}$ is the volume including the target to which material or stimulus can be delivered.

In this regard it will be appreciated that the volume to which stimulus or material may be delivered may be significantly greater than the size of the physical target itself, depending on the delivery mechanism used. Thus, for example, if material to be delivered to a cell is absorbed when placed within the vicinity of the cell, then the target volume $V_{tar}$ will be larger than the volume of the cell.

However, in a more detailed example, equation (2) still holds, but it can be assumed that the projection has its own volume ($V_{pro}$), and in this case the probability of contact is modified to change $V_{tar}$ to take into account the additional probe volume. In one example, if the projection is as shown in FIG. 1E, in which $d_1=d_2$, the volume of the targeting section within the target layer is given by:

$$V_{tar} = \sum_{i=1}^{N_{tar}} ((2d_1 + d_c)^2 d_c) \quad (3)$$

where: $N_{tar}$ is the number of targets, with diameter $d_c$.

Equation (3) can be modified to take into account variations in target size and shape, and probe size and shape. When $d_1$ and $d_c$ are constant, equation (3) becomes:

$$V_{tar} = N_{Tar}(2d_1+d_c)^2 d_c \quad (4)$$

So for a region of target layer of size z×z, where a projection reaches through the target layer, and containing a number of targets $N_{tar}$, the probability is given by:

$$P_{contact} = \frac{N_{Tar}(2d_1 + d_c)^2 d_c}{z^2 h_{layer}} \quad (5)$$

The above example assumes that the projection reaches fully through the target layer 350 (i.e. $P_{depth}=1$). However, this may not occur and accordingly the above described equation can be utilised to take into account the probability of the projection reaching the relevant cell layer, as described in equation (1) above.

So the general expression for the probability of a projection targeting the targets of interest (e.g. key cells, nuclei etc), defined as $P_{tar}$ is:

$$P_{tar}=P_{contact} \times P_{depth} \quad (6)$$

It will be appreciated that in the event that the projection lengths a, l are selected such that $P_{depth}=1$, then $P_{tar}=P_{contact}$.

At step 440 the number of targeting events required is determined. This is typically determined on the basis of studies performed indicating the number of targets to which material or stimuli must be delivered in order for a biological response to be affected. Often, this is determined by parametric empirical studies.

For example, when it is desired to deliver DNA to transfect Langerhans cells, at least one cell must be targeted. However, it is believed that to ensure a successful biological response, at least 10 cells, and more preferably at least 100 cells and up to or over 1,000 cells are targeted. It will be appreciated however that for different delivery mechanisms a different number of targets may be desirable.

At step 450, having determined the number of targeting events required (N), it is possible to use this and the probability of a single targeting event to determine a number of projections required, which is given by:

$$N=T/P_{tar}.$$

where:
T is the total number of delivery events required to produce the desired response.

Often in immunotherapeutic and drug applications (including vaccines), T is defined as a range, that can vary significantly between application and/or model (i.e. animal or human).

Figure 5A:
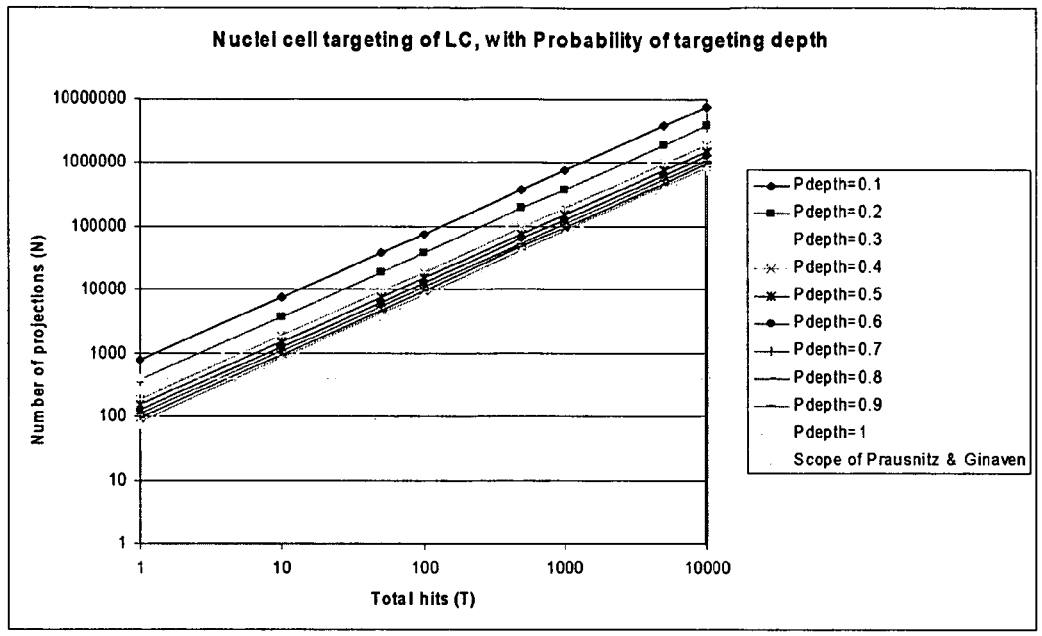
FIGS. 5A and 5B show examples of the relationship between the number of projections and total hits for targeting Langerhans cell nuclei and Langerhans cells respectively.
Figure 5B:
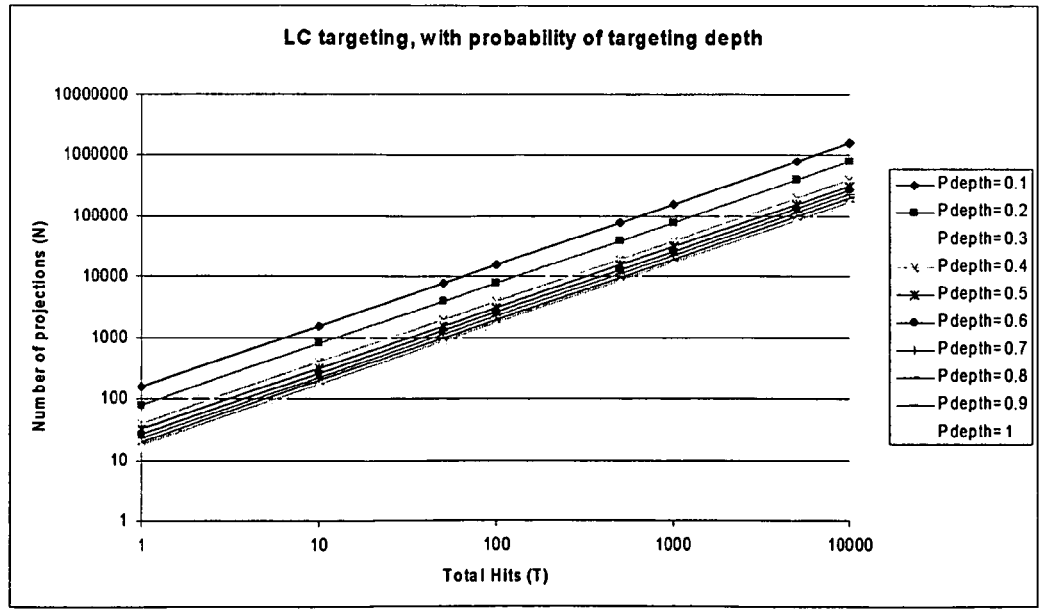

Specific examples of this are shown in FIGS. 5A and 5B, for the targeting of Langerhans cell nuclei and Langerhans cells respectively.

In these examples it is assumed that:
A Langerhans Cell (LC) penetrated by one needle remains viable. If it is penetrated by any more than one projection cell death occurs.
When a projection contacts the target site (e.g. cell nucleus or cytosol), the desired biological "event" occurs each time. In reality, there is probability of the event happening. For example, if cell transfection is required, then the probability of this event through the delivery of DNA to nucleus via a projection is ~0.9, whereas the probability of the same event from the coated projection entering only the cytoplasm is ~0.1 (Nagasaki 2005).
A dead cell cannot be transfected.
Penetration by a needle with a diameter greater than 1 μm will cause cell death.
LC are assumed as spherical with 10 μm diameter.
Nuclei of LC are assumed to be spherical, with a diameter of 4 μm (Arbuthnott, 2003).
All LC lie just above the basal layer between the epidermis and dermis (as reported by Kendall et al. (2003).
LC are oval with dimensions circa 11.25×6 μm but to simplify the model, the average of these two figures is taken as the diameter of 10 μm. In one example of young Balb/C mice the LC density is 895 cells/mm² (Choi. et al 1987). With LC uniformly distributed in the suprabasal region (Numahara et al. 2001) this gives a centre to centre spacing of approximately 30 microns justifying the spacing assumption. For simplicity, it is assumed that the LC spacing of 1000 cells/mm², giving a planar spacing between cell centres of 32 μm.

FIG. 5A shows the relationship between the number of projections and total hits is given for the patches 100 described above, with a range of depth probabilities ($P_{depth}$), for targeting Langerhans cell nuclei.

FIG. 5B shows the relationship between the number of projections and total hits is given for the patches 100 described above, with a range of depth probabilities (i.e. the probability of a viable targeting of the target layer 350), for targeting Langerhans cells.

Typically this requires at least 500 projections and more typically at least 1,000 projections for targeting LC and 10,000 projections for targeting LC nuclei. Specific examples of this will be described in more detail below.

At step 460 the projection spacing (S) is then determined based on the target diameter and target spacing. It is usual to assume that no more than one projection should enter a single cell this will typically lead to cell death. Accordingly, it is typical to select a projection spacing which is at least greater than a cell diameter, such that:

$$S \geq d_c$$

More preferably it is typical to select a size for the projection spacing based on a preferred overall patch size. In particular, it is preferred that patches are made below a certain upper limit defined by practical utility to the targeting site of the patient or animal.

Figure 10:
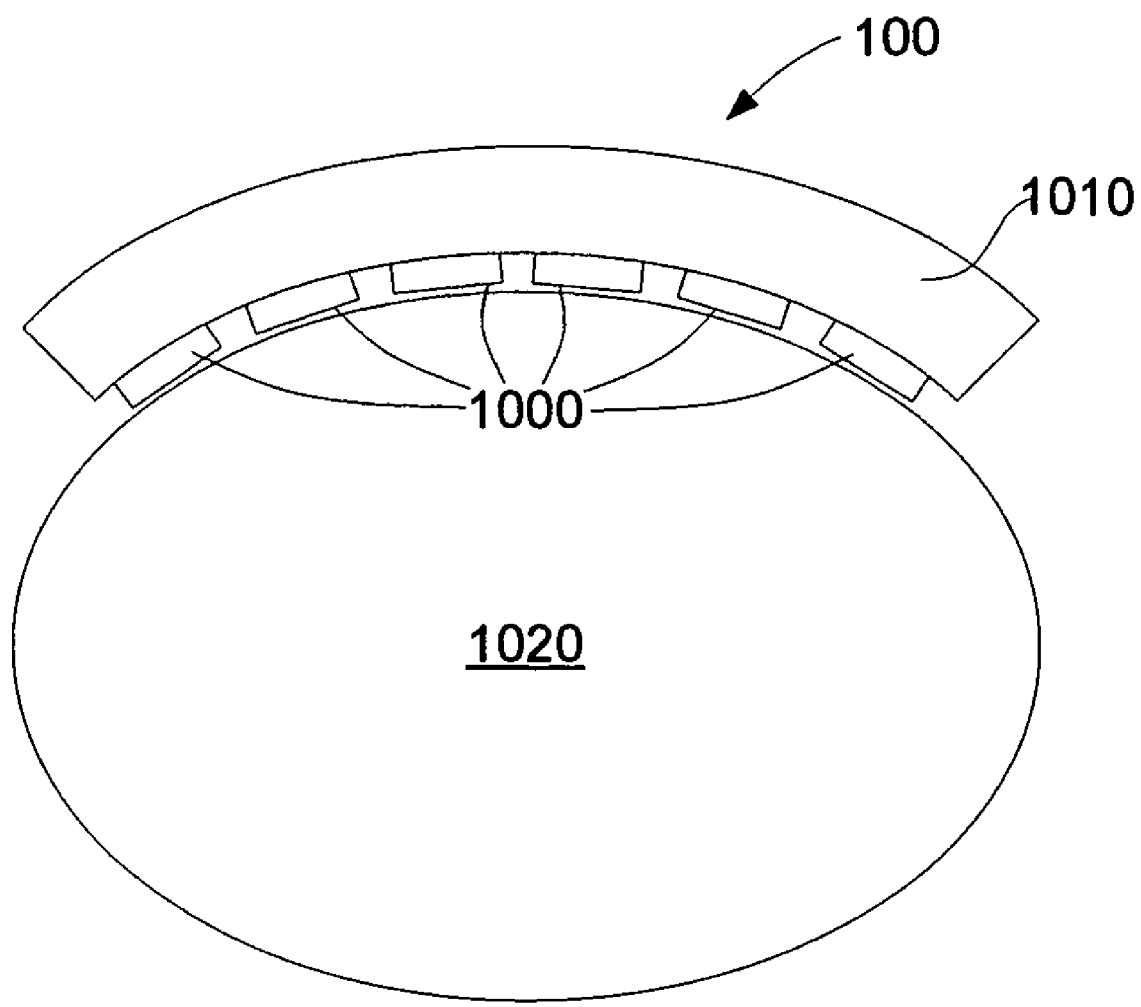
FIG. 10 is a schematic diagram of an alternative example of a patch.
Figure 11:
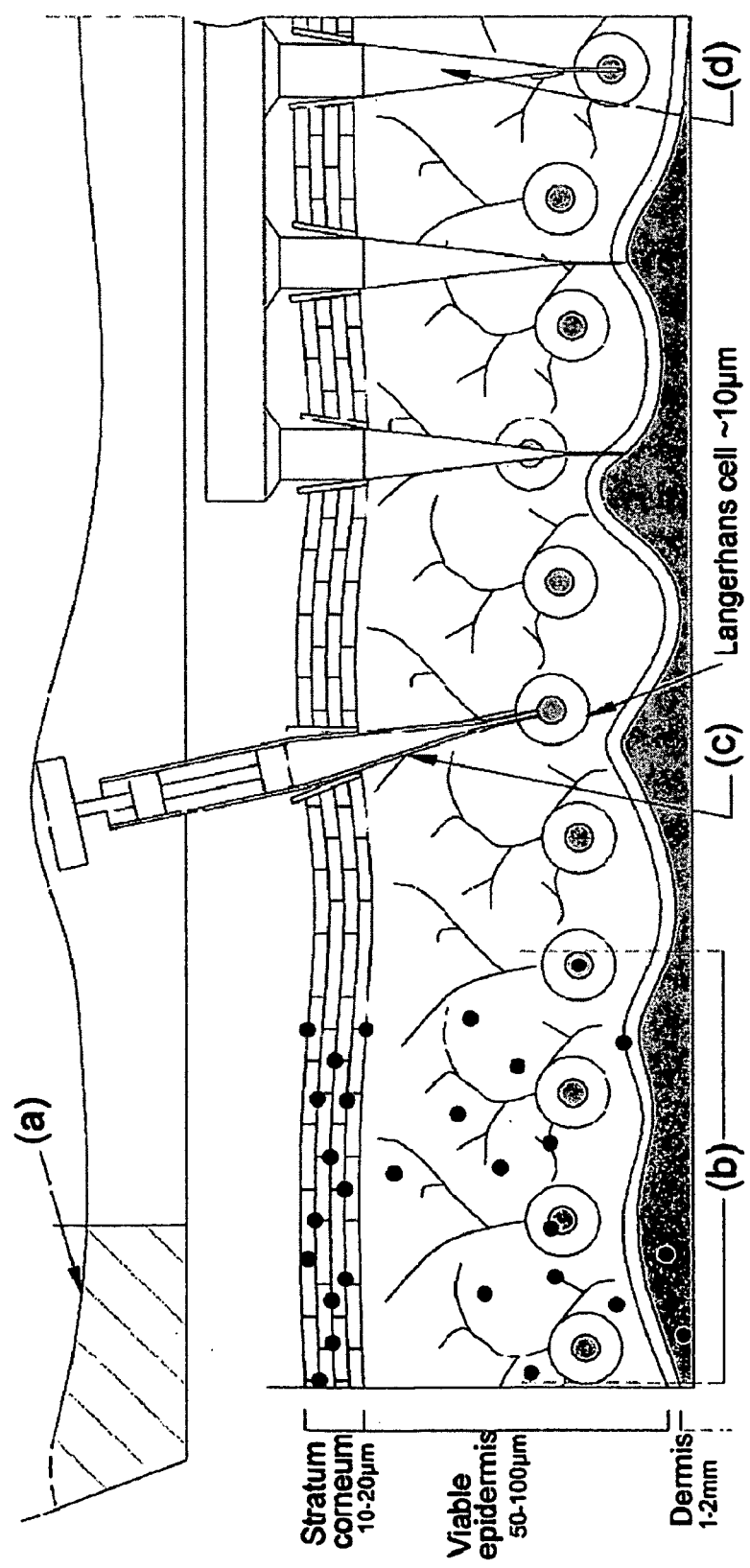
FIG. 11 illustrates a schematic cross-section of skin structure: (a) half-section scale of a typical smaller needle and syringe (diameter ~0.5 mm); (b) penetration of microparticles following biolistic delivery; (c) idealised direct injection of a cell nucleus; (d) a micro-nanoprojection array.
Figure 12:
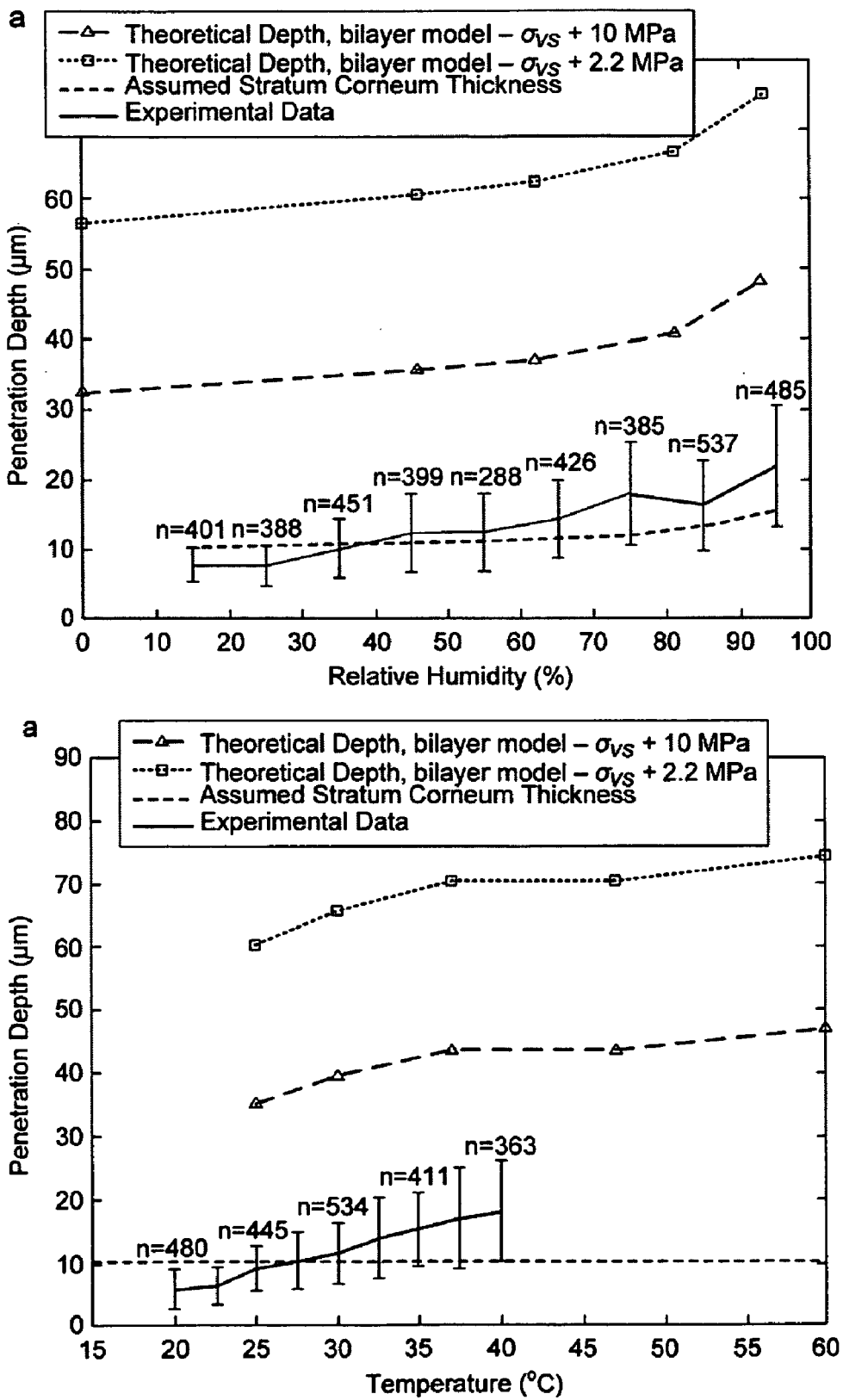
FIG. 12 illustrates the effects of relative humidity (a) and ambient temperature (b) on ballistic particle penetration into the skin.
Figure 13A:
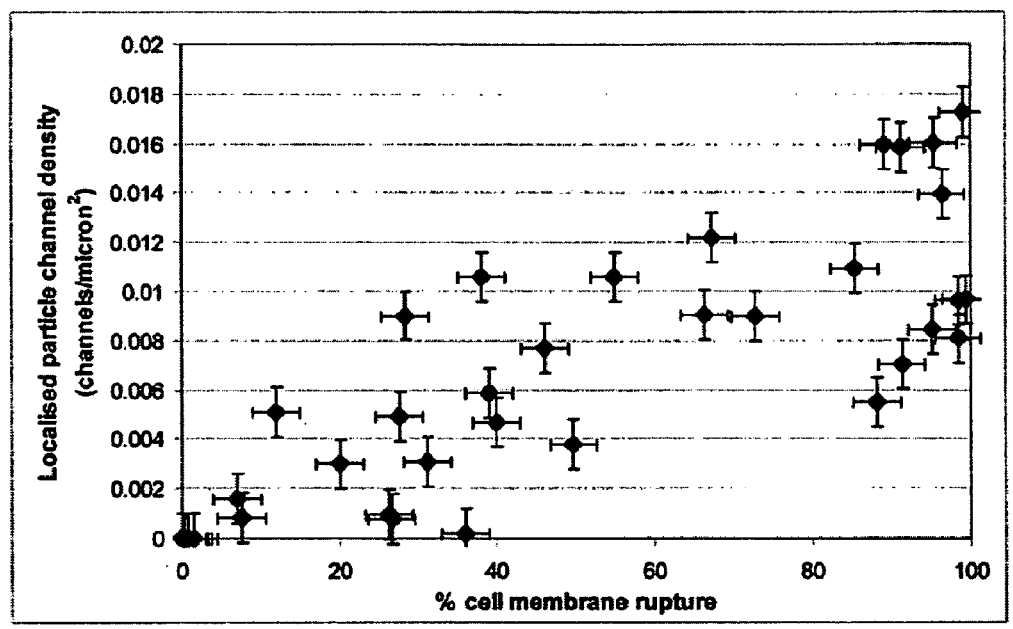
FIG. 13A is a graph showing the relationship between percentage cell death (membrane rupture) and particle density (McSloy (2004) MA Thesis, University of Oxford)
Figure 13B:
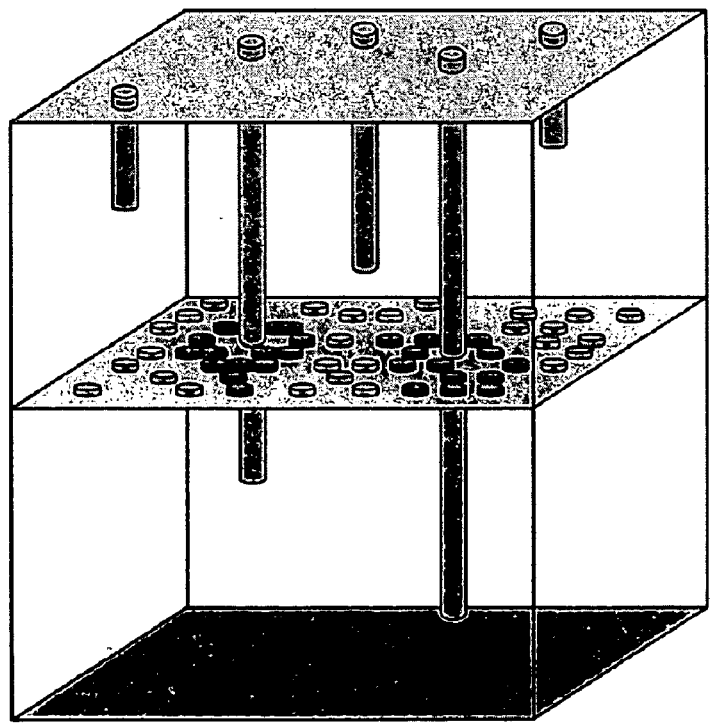
FIG. 13B is a diagram showing how the data for FIG. 13A was retrieved (McSloy (2004) MA Thesis, University of Oxford)
Figure 13C:
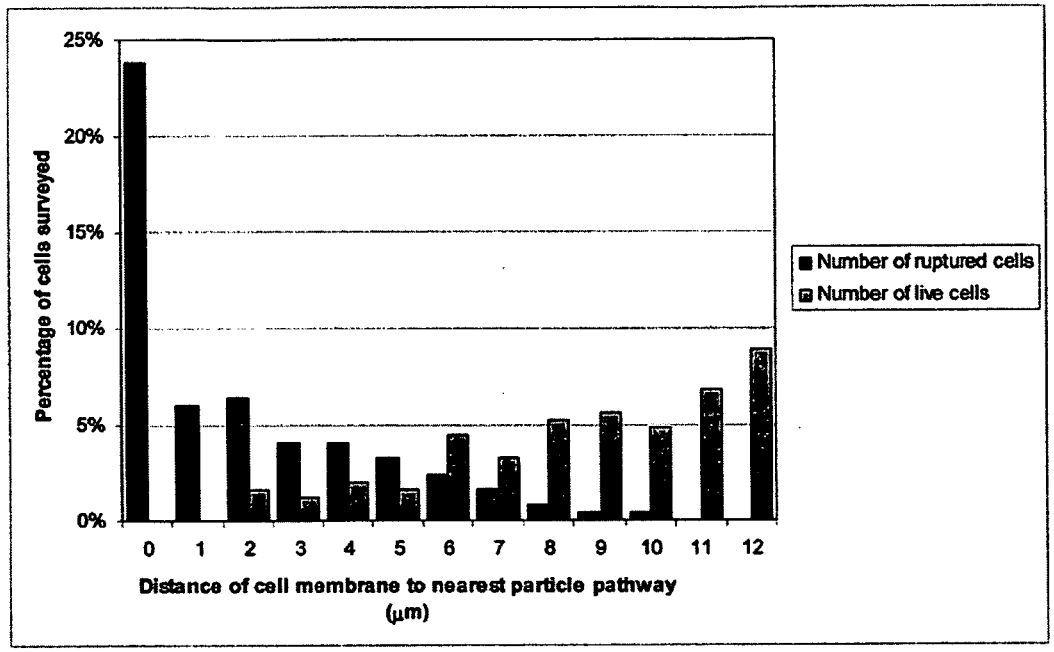
FIG. 13C is a graph showing membrane rupture versus distance of cell pathway.
Figure 14:
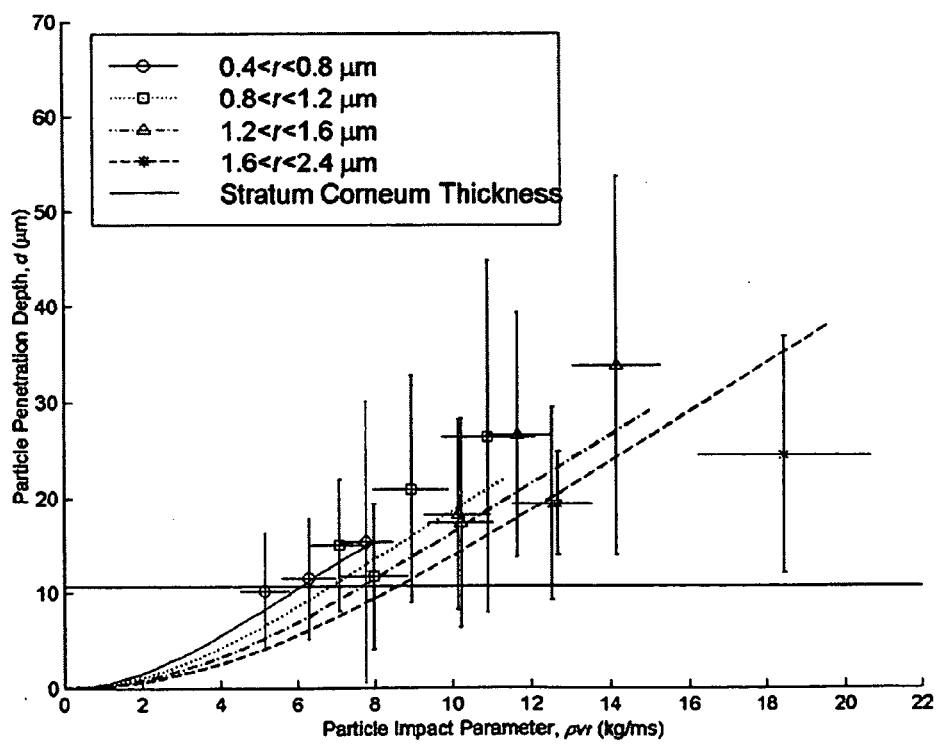
FIG. 14 illustrates the particle penetration parameter (pvr) vs. penetration depth obtained by the ballistic delivery of gold microparticles into skin (Kendall et al. (2004), Journal of Biomechanics)

For example, if the targeting site is the skin of the human abdomen, then the surface area could be approaching the surface area of the abdomen (e.g. ~400 cm², or 20×20 cm, say). It would not be practical to achieve such larger surface areas over surfaces with "bulk" curvature (such as the abdomen example, or arm) with one large rigid patch. In one example, surface area can be achieved using the patch shown in FIG. 10. In this example, the patch 100 is formed from several smaller patches 1000 provided on a flexible backing material 1010. The patch assembly could be extended to wrap around the patient site 1020.

In any event, an upper limit on the spacing S is typically selected to ensure that the desired number of projections fit on a patch of the desired size.

Figure 6:
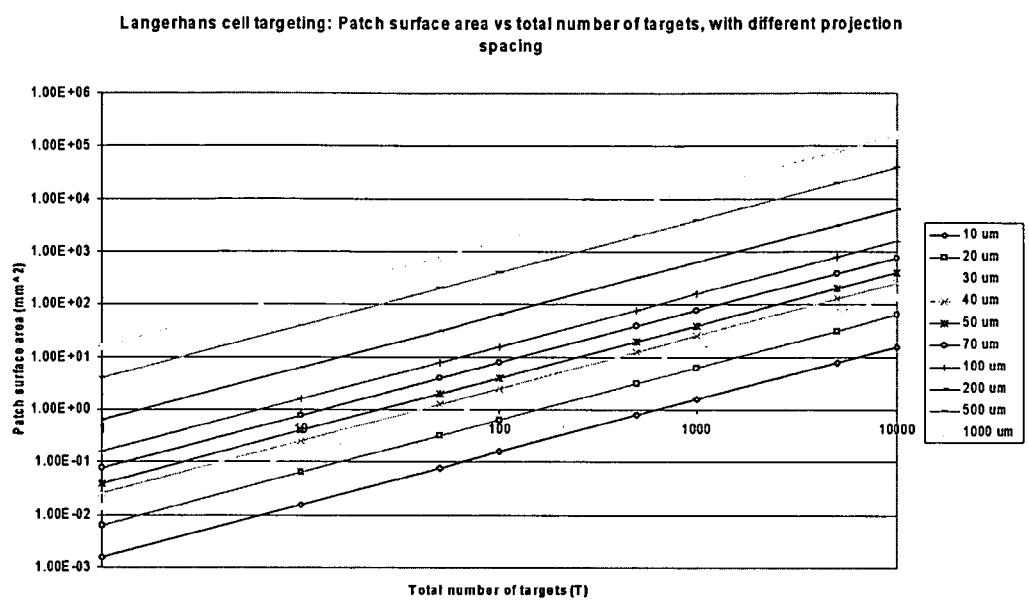
FIG. 6 shows an example of the relationship between the total number of targeted LC and the patch surface area as a function of projection spacing geometry.

A specific example of this is shown in FIG. 6, in which the relationship between the total number of targeted LC (T) and the patch surface area (mm²) as a function of spacing geometry, is shown. In this example, the probability of penetration to the cell depth is assumed to be one (i.e. $P_{depth}=1$) for simplicity. Irrespective of this, the projection spacing S is typically of the order of spacing of the targets $S_c$.

Figure 7:
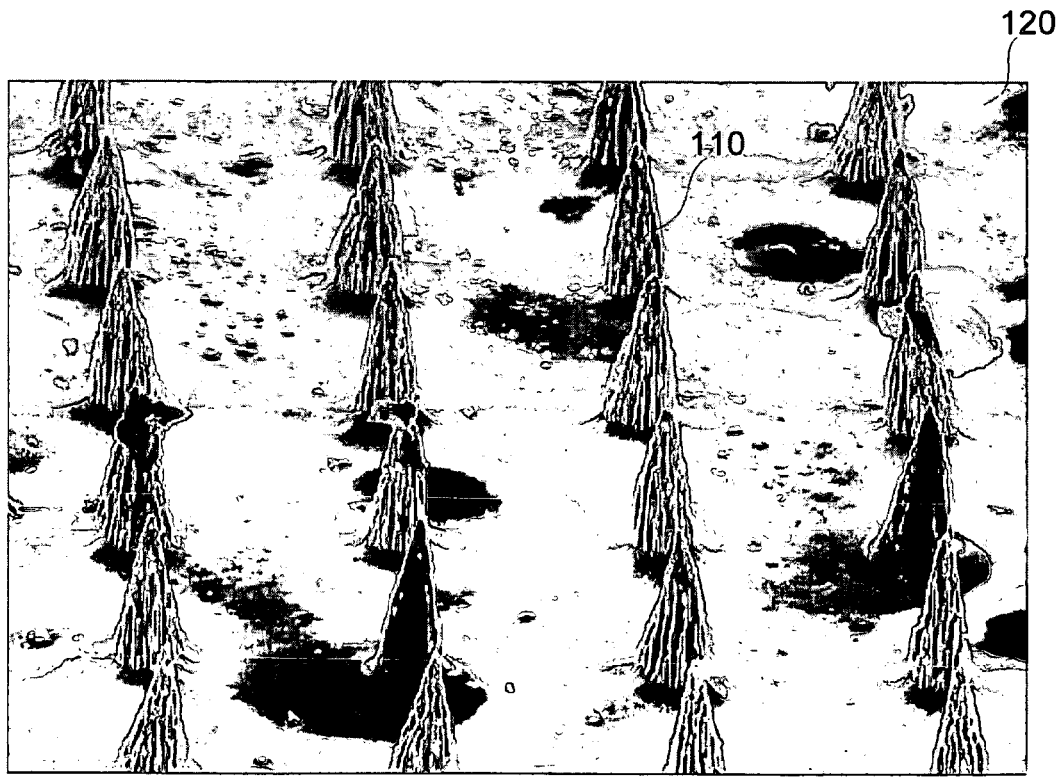
FIG. 7 is an SEM photograph of an example of a constructed patch.

Once the spacing is selected the patch can be fabricated at step 470. In general, this will typically require considerations are taken into account to ensure the projections are sufficiently robust to withstand penetration of the Stratum Corneum and Viable Epidermis without breaking. Example manufacturing processes will be described in more detail below, and an example of a constructed patch 100 is shown in FIG. 7. In this example, the device has 9795 projections, with a spacing of 70 µm (S), over a surface area of 48 mm².

In general, a number of factors regarding the patch fabrication should be noted.

Typically the projections are solid, non-porous and non-hollow. The use of solid projections enhances the projection strength, thereby reducing the likelihood of projection breakage, which in turn helps maximise successful delivery of material or stimulus to the targets. Also, solid projections simplify device fabrication processes, allowing for the production of cheaper patches than for the case of porous or hollow projections. This in turn further enhances the suitability of the patch for use in medical environments.

To achieve delivery of material, it is typical to coat at least the targeting section 111 with a non-liquid bioactive material, such as DNA.

The patch 100 may also be fabricated to perturb targets so as to induce "bystander" interactions. This may be used for example, so that cell death is used to release molecules to activate nearby targeted cells. This can be achieved in a number of manners, such as by providing a mixture of coated and uncoated projections, as well as by providing projections of differing dimensions including clusters of more than 1 projection to target individual cells and/or larger scale tips to damage cells or other targets, upon insertion/residence/retrieval.

Specific Examples

A number of specific examples will now be described.
Transfection Probability

In this example, which focuses on the transfection of Langerhans cells, a number of additional practical considerations may also be taken into account.

Figure 8:
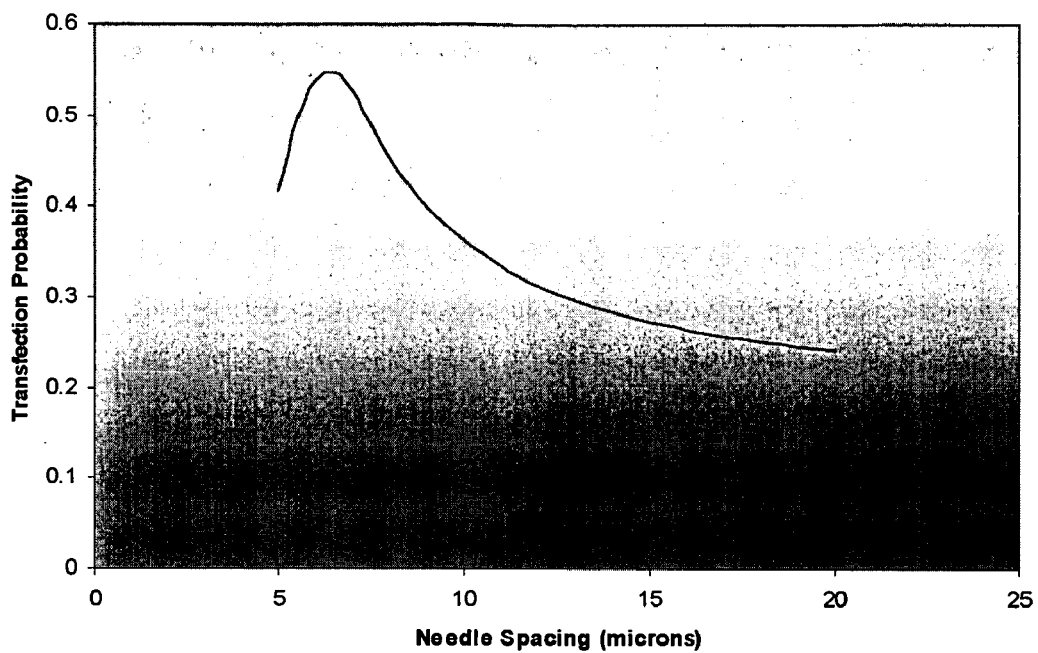
FIG. 8 shows an example of the Transfection Probability vs Needle Spacing, for targeting of Langerhans cells.

In particular, if the model of a point targeting section with no radius is used, this predicts an idealised projection spacing S=6.5 µm, as used in the example of FIG. 8. In this case, the LC diameter is ~10 µm, so that to satisfy the requirements set out above, namely that $S \leq d_c$, so $S \geq 10$ µm.

Also, for structural reasons, the diameter of the base of the projections $d_3$ is likely to be above 6.5 µm, and a "clearance" will be needed between each projection, so for practical reasons, the minimum projection spacing (S) is at least 10 µm.

Figure 9A:
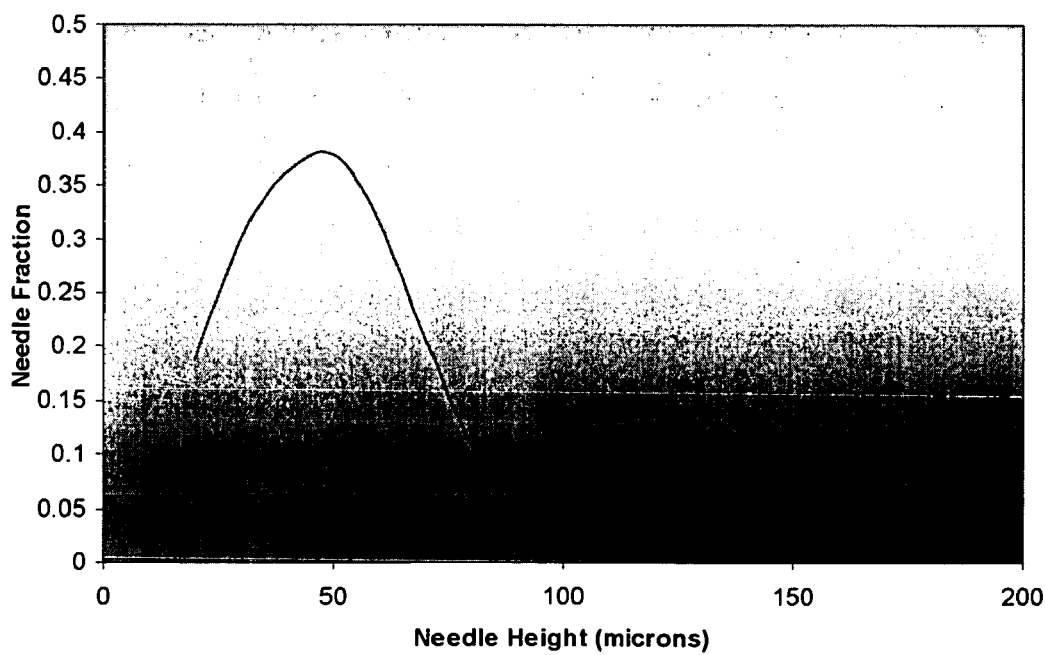

FIG. 8 shows an example of the Transfection Probability vs Needle Spacing, for targeting of Langerhans cells with a spacing of 32 µm. The $S \geq d_c$ criterion and practical considerations of minimum size of the base $d_3$ suggest the spacing is to at least be 10 µm, as discussed above.
Needle Length Optimisation For this example, the sensitivity of needle length to standard deviation of the skin surface is shown in FIGS. 9A to 9C. In particular, these show the fraction of projections ($P_{depth}$) that are smaller than 1 µm in diameter and penetrate to 17 µm in the epidermis (the depth of LC), against the projection height, for skin level standard deviation of 20 µm, 40 µm and 60 µm respectively.

It is clear from this, that the magnitude of skin undulations has a strong influence over the choice of optimum projection length.
Minimum Number of Projections In one example, for targeting a single LC nucleus the likelihood of contact of a projection is given by $P_{contact}=0.031$, using equation (2) above, and data regarding LC nuclei size, set out in more detail below. The value of $P_{depth}$ defined in equation (1), above has a range of 0-1, and with N=500, $P_{depth}=0.064$.

Utilising this, it can be seen that a viable range of lengths result in targeting of a single cell, as shown below.

| FIG. | SD (roughness) (µm) | Needle length needed (T = 1; N = 500) |
|------|---------------------|---------------------------------------|
| 9A   | 20                  | >80 µm.                               |
| 9B   | 40                  | >130 µm.                              |
| 9C   | 60                  | >160 µm                               |

All of these cases in the table above are well away from the optimal lengths for the projections (i.e. where $P_{depth}$ is a maximum in FIGS. 9A-9C), so they do represent a "poor"

case scenario, where the device is not tuned well for the target (device tuning would be improved by reducing the needle length to closer to the optimal regions shown in FIGS. 9A-9C, for example). However, the target of LC nuclei is very well defined. So, on balance, a minimum of 500 projections is needed before there is a reasonable statistical chance of just one targeting event.

It will be appreciated that it is typical however to deliver to more than one target, and accordingly, it is typical for a greater number of projections to be provided.

For example, the direct targeting of 2 LC nuclei (i.e. T=2) would be achieved with the device configurations in the table above with 1000 projections (i.e. N=1000).

Similarly, the direct targeting of 10 LC nuclei (i.e. T=10) would be achieved with the device configurations in the table above with 5000 projections (i.e. N=5000).

In the case of targeting situations with a lower $P_{contact}$, for instance in targeting a sparsely-populated dermal dendritic cell phenotype (not in a tightly defined layer like LC), greater than the minimum of 500 projections would be needed for at least one single targeting event. For example, if $P_{contact}$ is 1/10 of the stated LC case (i.e. $P_{contact}$=0.0031), then applying a similar analysis, and adjusting for the deeper location of cells to maintain $P_{depth}$=0.064, then 5000 projections would be needed for the one targeting event.

Again, it will be appreciated that it is typical however to deliver to more than one target, and accordingly, it is typical for a greater number of projections to be provided.

Maximum Number of Projections

The upper limit of projections is typically defined by a range of parameters. These include the total surface area of the target site available, and the minimum projection spacing (S). For example, in previously stated case of a human abdomen, with the patch assembly wrapped around to the back (i.e. ~800 cm$^2$), and the minimum spacing for targeting cells (S=10 μm) results in 8,000,000 projections.

Another consideration is the payload to be delivered to the target site, where for a given application there is an upper limit in active material or stimulus to be delivered. Here, if a given mass of active material is coated to a single projection, then the total number of projections would be selected such that the total payload is less than this upper limit.

In any event, it will be appreciated from the above that it is typical to use at least 500 projections, but more typically at least 750, 1000, 2000, 5000, 7500, 10,000, 100,000 projections, and even as many as 10,000,000 projections.

Delivery

Illustrative stimuli or material that can be delivered with the device of the present invention include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

In some embodiments, the stimulus or material is selected from nucleic acids, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs.

In other embodiments, the stimulus or material is selected from peptides or polypeptides, illustrative examples of which include insulin, proinsulin, follicle stimulating hormone, insulin like growthfactor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon likepeptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

In still other embodiments, the stimulus or material is selected from receptor ligands. Illustrative examples of receptors include Fc receptor, heparin sulfate receptor, vitronectin receptor, Vcam-1 receptor, hemaglutinin receptor, Pyr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotien) receptor, aminopeptidease N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

In specific embodiments, the stimuli or material are selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain embodiments, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein; gp75, oncofetal antigen, GM2 and GD2 gangliosides, cdc27, p21ras, gp100$^{Pmel117}$ or a combination thereof. Other tumour-specific antigens include, but are not limited to: etv6, am11, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruit-fly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

Exemplary pathogenic organisms include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neurarninidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis*, *Candida* spp., *Cladophialophora carrionii*, *Coccoidiodes immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. duboisii, *Hortaea werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete* fungi, *Absidia corymbifera*, *Rhizomucor pusillus* and *Rhizopus arrhizus*. Thus, representative fungal antigens that can be used in the compositions and methods of the present invention include, but are not limited to, candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components; and tinea fungal antigens such as trichophytin and other *coccidiodes* fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: plasmodium falciparum antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other *toxoplasma* antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The present invention also contemplates toxin components as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

In specific embodiments, the antigen is delivered to antigen-presenting cells. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some embodiments, the antigen-presenting cell is selected from monocytes, macrophages, B lymphocytes, cells of myeloid lineage, dendritic cells or Langerhans cells. In certain advantageous embodiments, the antigen-presenting cell expresses CD11c and includes a dendritic cell or Langerhans cell. In some embodiments the antigen-presenting cell stimulates an immune response. In other embodiments, the antigen-presenting cell induces a tolerogenic response.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one embodiment, the cytolysin is fused or otherwise linked to the antigen, wherein the fusion or linkage permits the delivery of the antigen to the cytosol of the target cell. In another embodiment, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred embodiment of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of non-virulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogenes, Shigella flexneri*, mycobacterium, *Salmonella, Bacillus subtilis*, etc. In a particular embodiment, the bacteria are attenuated to be non-replicative, non-integrative into the host cell genome, and/or non-motile inter- or intra-cellularly.

The delivery vehicles described above can be used to deliver one or more antigens to virtually any antigen-presenting cell capable of endocytosis of the subject vehicle, including phagocytic and non-phagocytic antigen-presenting cells. In embodiments when the delivery vehicle is a microbe, the subject methods generally require microbial uptake by the target cell and subsequent lysis within the antigen-presenting cell vacuole (including phagosomes and endosomes).

In other embodiments, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2):205-208), Vigna and Naldini (2000, *J. Gene Med.* 2(5): 308-316), Kay, et al. (2001, *Nat. Med.* 7(1):33-40), Athanasopoulos, et al. (2000, *Int. J. Mol. Med.* 6(4):363-375) and Walther and Stein (2000, *Drugs* 60(2):249-271).

Experimental Results

Preliminary data in a mouse model, using a virus as a delivery vehicle to the skin using an embodiment of the patches 100 described above elicited significantly higher cytotoxic T-lymphocyte responses than conventional intradermal injection of the same antigenic preparation, with the same payload.

Accordingly, the above described examples provide a device for the delivery of a bioactive material (agent) or other stimulus to an internal site in the body, comprising a plurality (number) of projections that can penetrate a body surface so as to deliver the bioactive material or stimulus to the required site.

In one example, the number of projections is selected to be at least 500, to thereby induce a biological response. Typically the exact number of projections is determined in accordance with the above described equations, thereby maximising the chance of delivery of material or stimulus to the target.

The delivery end portion of the projection may also be dimensioned so as to be capable of insertion into targeted cells to deliver the bioactive material or stimulus without appreciable damage to the targeted cells or specific sites therein. Thus, the dimensions of the delivery end portion of the microprojections, including the length or diameter, can be selected which enables delivery of the agent or stimulus to targeted cells and internal components within cells.

The nanoneedles are typically solid (non-hollow) in cross-section. This leads to a number of technical advantages which include: reliable delivery of bioactive material or stimulus; ease and cost of manufacturing, and increased strength.

Variations

A number of variations and options for use with the above described devices will now be described.

Herein, the terms "projection", "micro-nanoprojection", "nanoneedle", "nanoprojection", "needle", "rod" etc are used interchangeably to describe the solid projections.

In cases where a material or agent is to be transported, projections may be coated on the outside of the nanoneedles. This provides a higher probability of delivering the coating to the depth of interest compared to microparticle delivery from a gene gun and thus is more efficient.

A further feature is that the nanoneedles may be used for delivery not only through the skin but through other body surfaces, including mucosal surfaces, to cellular sites below the outer layer or layers of such surfaces. The term "internal site", as used herein, is to be understood as indicating a site below the outer layer(s) of skin and other tissues for which the devices of the present invention are to be used.

Furthermore, these nanoneedles may be used to deliver stimuli to cells or cell components other than those resulting from the administration of bioactive agents such as drugs and antigenic materials for example. Mere penetration of cellular sites with nanoneedles may be sufficient to induce a beneficial response, as indicated hereinafter.

The device is suitable for intracellular delivery. The device is suitable for delivery to specific organelles within cells. Examples of organelles to which the device can be applied include a cell nucleus, endoplasmic reticulum, ribosome, or lysosome for example.

In one embodiment the device is provided having a needle support section, that is to say the projections comprise a suitable support section, of sufficient length to reach the desired site and a (needle) delivery end section having a length no greater than 20 microns and a maximum width no greater than 5 microns, preferably no greater than 2 microns.

In one example, the maximum width of the delivery end section is no greater than 1000 nm, even more preferably the maximum width of the delivery end section is no greater than 500 nm.

In one embodiment, the device can be used for delivery intradermally. This device may have a needle support section, that is to say the projections comprise a suitable support section, of length at least 10 microns and a (needle) delivery end section having a length no greater than 20 microns and a maximum width no greater than 5 microns, preferably no greater than 2 microns.

The maximum width of the delivery end section is usually no greater than 1000 nm, even more preferably the maximum width of the delivery end section is no greater than 500 nm.

In a further embodiment, the device is for mucosal delivery. This device may have a needle support section, that is to say the projections comprise a suitable support section, of sufficient length to reach the desired site, such as of length at least 100 microns and a (needle) delivery end section having a length no greater than 20 microns and a maximum width no greater than 5 microns, preferably no greater than 2 microns.

In one embodiment, the device of the invention is for delivery to lung or other internal organ or tissue. In a further embodiment, the device is for in-vitro delivery to tissue, cell cultures, cell lines, organs, artificial tissues and tissue engineered products. This device typically has a needle support section, that is to say the projections comprise a suitable support section, of length at least 5 microns and a needle delivery end section having a length no greater than 20 microns and a maximum width no greater than 5 microns, preferably no greater than 2 microns.

In one embodiment, the device comprises projections in which the (needle) delivery end section and support length, that is to say the "needle support section", is coated with a bioactive material across the whole or part of its length. The (needle) delivery end section and support length may be coated on selective areas thereof. This may depend upon the bioactive material being used or the target selected for example.

In a further embodiment, a bioactive material is releasably incorporated into the material of which the needle, or projection, is composed. All, or part of the projection may be constructed of a biocompatible, biodegradable polymer (such as Poly Lactic Acid (PLA), PolyGlycolic Acid (PGA) or PGLA or Poly Glucleic Acid), which is formulated with the bioactive material of choice. The projections may then be inserted into the appropriate target site and, as they dissolve, the bioactive material will enter the organelle(s)/cells.

In one example, at least the delivery end section of the needle is composed of a biodegradable material.

In an alternative embodiment of the invention, a device is also provided in which the needle has no bioactive material on or within it. The targeted cell or organelle is perturbed/stimulated by the physical disruption caused by the (delivery end of the) nanoneedle (projection). This physical stimulus may, for example, be coupled with electric stimulus as a form of specific nanoelectroporation of particular organelles or the cell.

The bioactive material or stimulus delivered by the device of the invention may be any suitable material or stimulus which gives the desired effect at the target site.

Examples of bioactive materials, which are not intended to be limiting with respect to the invention include polynucleotides and nucleic acid or protein molecules, antigens, allergens, adjuvants, molecules, elements or compounds. In addition, the device may be coated with materials such as biosensors, nanosensors or MEMS.

In one aspect, the device is provided in the form of a patch containing a plurality of needles (projections) for application to a body surface. A multiplicity of projections can allow multiple cells and organelles to be targeted and provided with a bioactive material or stimulus at the same time. The patch may be of any suitable shape, such as square or round for example. The overall number of projections per patch depends upon the particular application in which the device is to be used. Preferably, the patch has at least 10 needles per mm, and more preferably at least 100 needles per mm². Considerations and specific examples of such a patch are provided in more detail below.

Examples of specific manufacturing steps used to fabricate the device are described in greater detail below. In one preferred aspect, the device of the invention is constructed from biocompatible materials such as Titanium, Gold, Silver or Silicon, for example. This may be the entire device, or alternatively it may only be the projections or the delivery end section of the projections which are made from the biocompatible materials.

One manufacturing method for the device utilises the Deep Reactive Ion Etching (DRIE) of the patterns direct from silicon wafers, see the construction section below.

Another manufacturing method for the device utilises manufacturing from a male template constructed with X-ray lithography, electrodeposition and moulding (LIGA). The templates are then multiply inserted into a soft polymer to produce a plurality of masks. The masks are then vacuum deposited/sputtered with the material of choice for the nanoprojections, such as titanium, gold, silver, or tungsten. Magnetron sputtering may also be applied, see the construction section below.

An alternative means for producing masks is with 2 photon Stereolithography, a technique which is known in the art and is described in more detail below.

In one embodiment, the device is constructed of silicon.

The device may be for a single use or may be used and then recoated with the same or a different bioactive material or other stimulus, for example.

In one embodiment, the device comprises projections which are of differing lengths and/or diameters (or thicknesses depending on the shape of the projections) to allow targeting of different targets within the same use of the device.

An example of the practical application of such a device is explained in further detail below (see section 6.2.4).

Also provided throughout the specification are numerous uses of the device, which has many useful medical applications in the treatment of a number of diseases.

Further Examples

Further examples will now be described in more detail. For the purpose of these examples, the explanation will focus on the targeting of cells, cell organelles or cell nuclei. However it will be appreciated that the techniques may be used to deliver material/stimulus to any suitable specific target.

1. Specific Targets For Delivery

Figure 15:
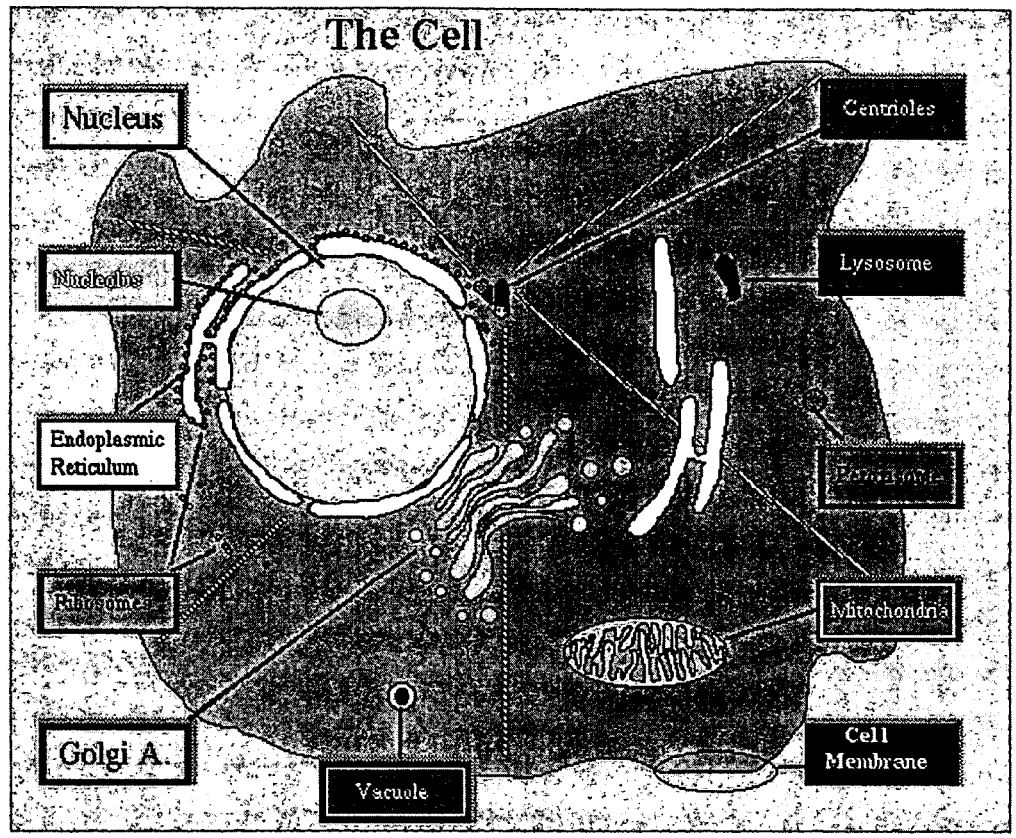
FIG. 15 shows examples of organelles within the cell (http://niko.unl.edu/bsl01/notes/chapter4.html)

In one example, the target of interest is within the cells. The position and shape of key organelles within the cells are shown in FIG. 15. All eucaryotic cells have the same basic set of membrane enclosed organelles. The number and volume of the key organelles varies with cell type. As to the targeting of specific organelles, there is a probability attached to each event on the basis of volume. Consider the non-specific targeting of the cell (i.e. at the correct depth, but without the precise targeting with the aid of imaging techniques). The probability of targeting the nucleus, for example, in a cell is given by the volume of the nucleus vs. the remainder of the cell.

In Table 1 below, the scale of organelles and their mass fraction and number are listed. The primary data for this summary is from "Genes VI" by Benjamin Lewin and "The Molecular Biology of the Cell" Alberts et al., 4th Ed. This information pertains to the Liver Cell. Also listed in Table 1 are example applications and that may be induced or enhanced as a result of targeting these organelles.

Working in increasing scale, the starting point is the cell membrane, which is ~10 nm thick.

In piercing these membranes with a minimal disruption to the viability of the cell, a range of drugs, vaccines and other compounds can be delivered to cells. Specifically, the Endoplasmic Reticulum (a convoluted envelope, 75 nm in thickness) may be targeted within RNA to transfect cells in the areas of Vaccination or Gene Therapy. Lysosomes, which are 200-500 nm in size can be targeted for release of enzymes to induce autolysis (cell death). For an effective cellular response (MHC Class I) with DNA vaccination and gene therapy, it is important that the DNA material is delivered intact to the cell nucleus.

Most of these organelles are of the submicron scale.

TABLE 1

The scale, number and potential targets of key organelles within cells.
(http://niko.unl.edu/bs101/notes/sizes.html and
"Molecular Biology of the Cell" 4'" Ed, Alberts et al.)

| Scale | Organelle | Mass/Volume Fraction | Number per cell | Utility as target | Application |
|---|---|---|---|---|---|
| ~0.1 nm | Hydrogen Atom | | | | |
| ~0.8 nm | Amino Acid | | | | |
| ~2 nm (diameter) | DNA Alpha helix | ~2% | | | |
| ~2 nm | mRNA | ~2% | ~2,500 | | |
| ~2 nm | tRNA | ~3% | ~160,000 | | |

TABLE 1-continued

The scale, number and potential targets of key organelles within cells.
(http://niko.unl.edu/bs101/notes/sizes.html and
"Molecular Biology of the Cell" 4'" Ed, Alberts et al.)

| Scale | Organelle | Mass/ Volume Fraction | Number per cell | Utility as target | Application |
|---|---|---|---|---|---|
| ~2 nm | RNA | ~21% | | | |
| ~4 nm | Globular Protein | | | | |
| ~10 nm | Cell membranes | ~10% | | Use nanoneedles to pierce these membranes with minimal disruption to the cell. | To enhance drug/vaccine delivery of cells through perfusion |
| ~11 nm | Ribosome | ~9% | | | |
| ~25 nm | Microtubule diameter | | | | |
| ~75 nm (envelope thickness) | Endoplasmic reticulum (smooth, rough, Golgi) | ~15% | | Target with RNA, mRNA, iRNA for up regulating or interfering the production of proteins | Vaccination, gene therapy for cancerous cells. |
| ~100 nm | Large Virus | | | | |
| ~200-500 nm | Lysosomes | ~1% | | Pierce the lysosomes to release enzymes and induces autolysis (self digestion of the cell). | Inducing cell death in cancerous cells. |
| ~3 μm × 200 nm | Mitochondrion | ~22% | | | |
| ~3-6 μm | Nucleus | ~6% (Liver) 16% (LC) | 1 | Target for DNA delivery to the cell directly and/or disturb the double membrane. | DNA vaccination or gene therapy. |
| ~10-30 μm (diameter) | Cell | | | Langerhans cells are ~10 μm in diameter. | |

2. Routes Of Delivery To Cells

The type and scale of organelles within cells has been presented. Now the location of these cells within the tissue is identified. The selected tissue routes are.
Intradermal
Mucosal
Lung
Internal tissues
In-vitro sites.

2.1 Intradermal Delivery

Figure 16:
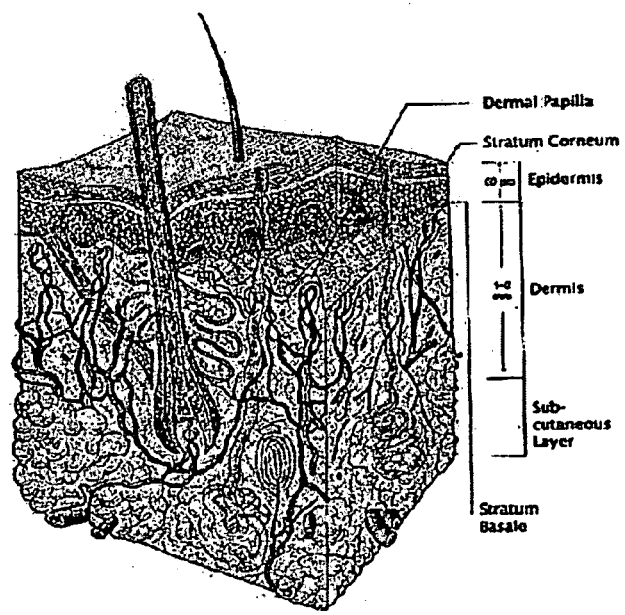
FIG. 16 is a schematic diagram of the skin structure.
Figure 17:
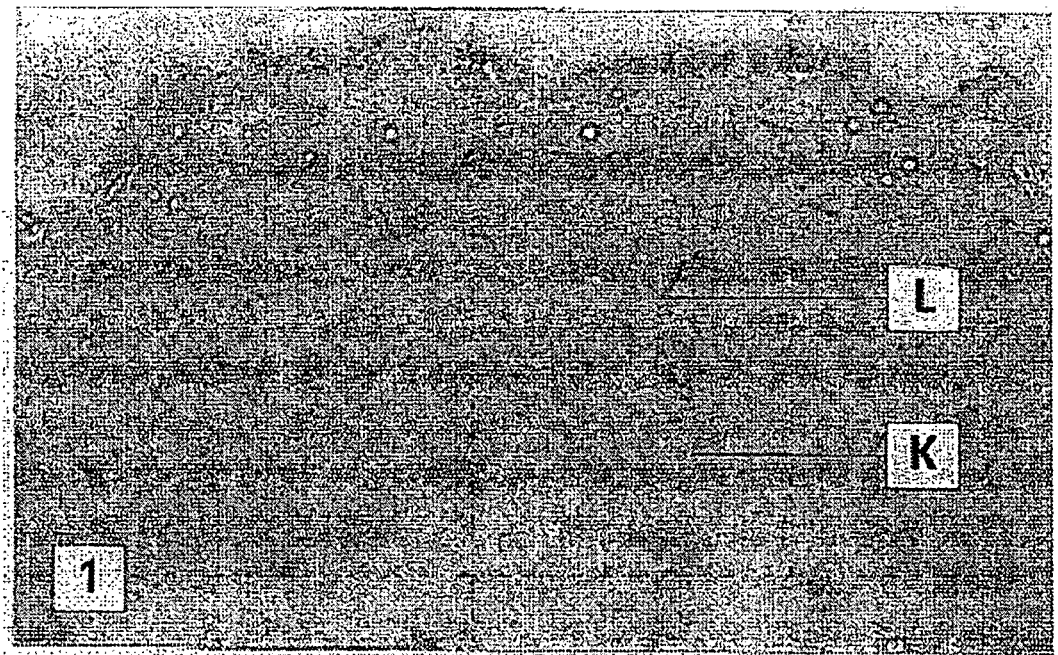
FIG. 17 is an example of a histology micrograph of human skin with a Langerhans Cell (L) and Keratinocyte (K) stained. From Roitt et al, the height of which is approximately 50 μm.

The skin is one convenient route for drug and vaccine delivery. A schematic of the skin is shown in FIG. 16. A full description of the anatomy of the skin is given in textbooks. A closer view of a histology section of skin is shown in FIG. 17 in a photomicrograph. Respective thicknesses of layers vary between species and sites.

Figure 18:
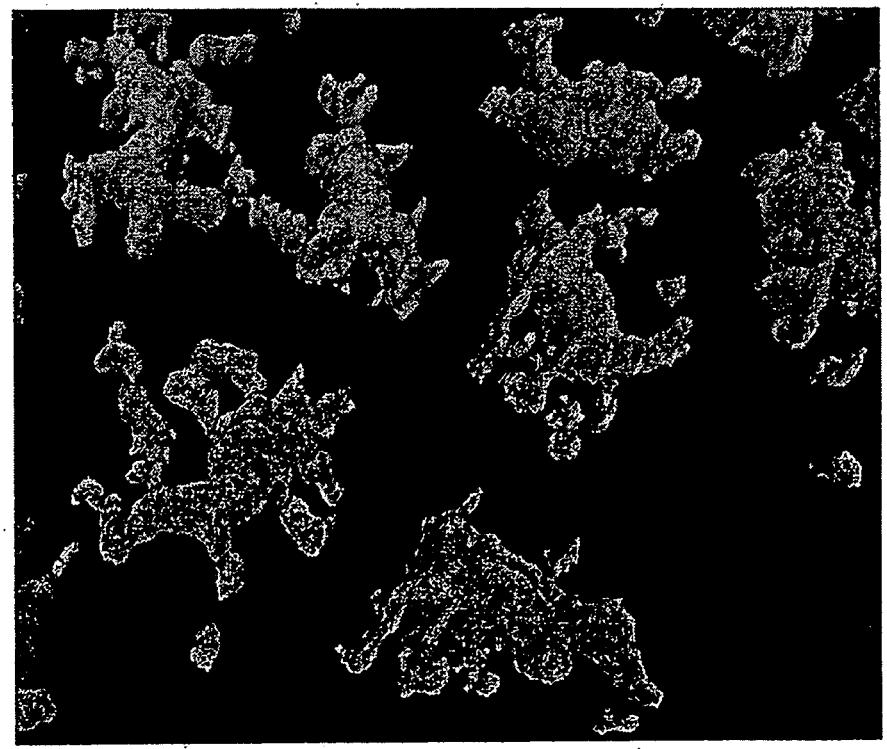
FIG. 18 illustrates the distribution of Langerhans Cells in a mouse ear (Kendall M. A. F., Mulholland W. J., Tirlapur U. K., Arbuthnott E. S., and Armitage, M. (2003) "Targeted delivery of micro-particles to epithelial cells for immunotherapy and vaccines: an experimental and probabilistic study", The 6th International Conference on Cellular Engineering, Sydney, August 20-22)

A key barrier to many drugs and vaccines is the Stratum Corneum (SC). In humans, this barrier is 10-20 μm thick with large variations from site-to-site with different ages and sexes. Below the SC is the Viable Epidermis (VE), which is typically 40-60 μm thick in humans. Within the VE are immunologically sensitive Langerhans Cells (LC). FIG. 17 shows a stained LC, marked as "L", residing above the basal layer. The spatial distribution of LC is illustrated in a 3D distribution of LC in a mouse, FIG. 18 (Kendall M. A. F., Mulholland W. J., Tirlapur U. K., Arbuthnott E. S., and Armitage, M. (2003) "Targeted delivery of micro-particles to epithelial cells for immunotherapy and vaccines: an experimental and probabilistic study", The 6th International Conference on Cellular Engineering, Sydney, August 20-22).

There are typically about 1000 LC per square mm and they reside just above the basement membrane of the viable epidermis (i.e. 30-80 μm deep). Importantly, the depth of LC varies significantly with the biological variability of the tissue, including rete ridges etc.

One objective in vaccination and gene therapy applications is to target LC residing 30-80 μm below the skin surface. In order to do this, the SC and cell membranes are to be breached. Furthermore, the organelles within the LC are to be targeted to elicit particular responses. One example is in the triggering of MHC I responses, whereby intact DNA is to be delivered to cell the nucleus. Alternatively, mRNA can be delivered to the Endoplasmic Reticulum or the cytoplasm.

Similarly, in the treatment of skin cancers such as Squamous Cell Carcinoma, cancerous cells within the VE may be directly targeted.

In some applications it may be beneficial to target cells deeper into the dermis. For example, in Basal Cell Carcinoma, the cells to be targeted are deeper in the tissue, approaching hundreds of microns (600 μm to 800 μm) (British Journal of Dermatology 149(5) Page 1035-2003).

2.2 Mucosal Delivery

Figure 19:
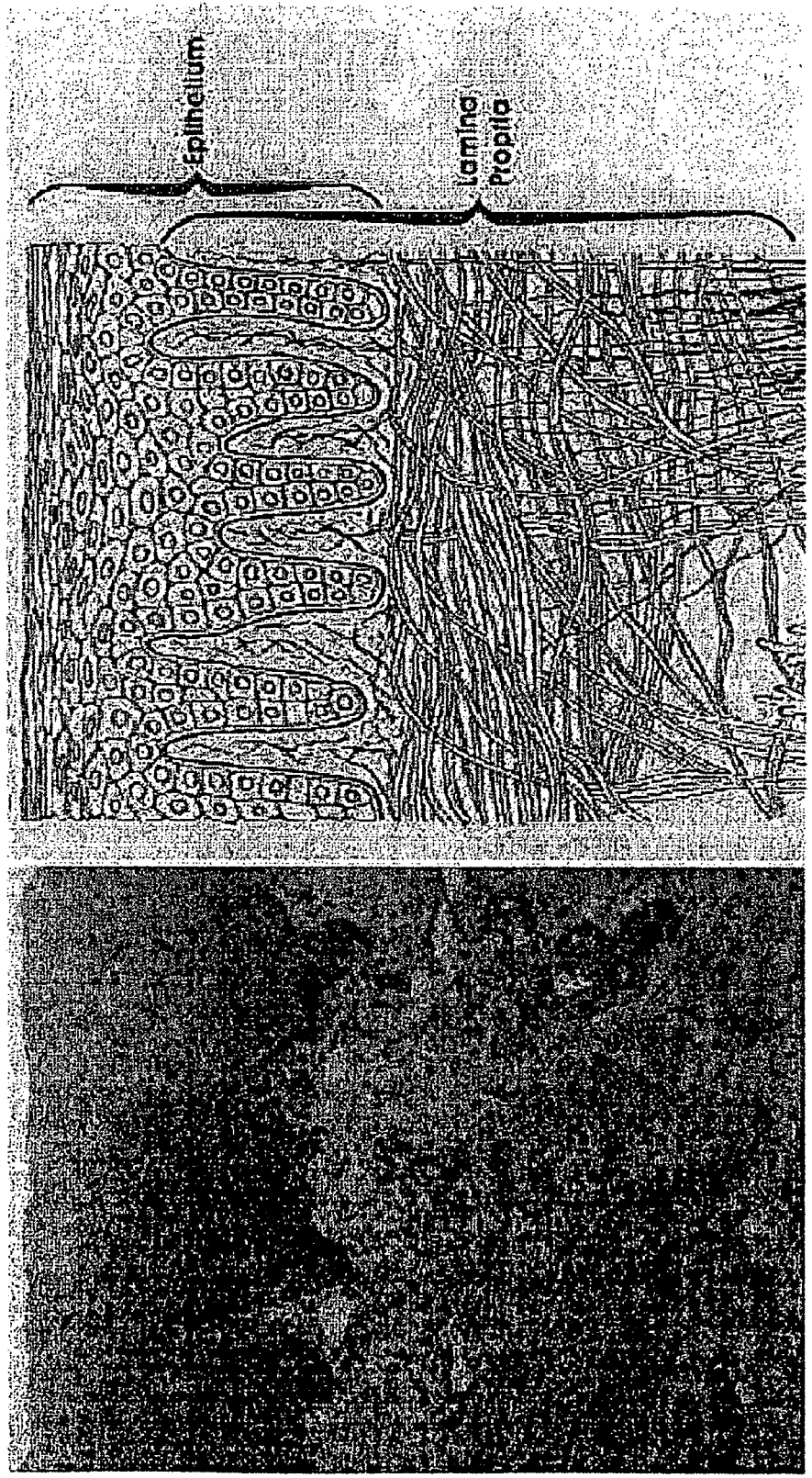
FIG. 19 illustrates a sample of canine buccal mucosal tissue and the structure of the mucosa, Mitchell, T (2003) DPhil Thesis, Department of Engineering Science, University of Oxford.

FIG. 19 shows a photomicrograph of a histology section of the mucosa. The physiology of the mucosa is similar to the skin. However there are some notable differences:

the mucosa does not have a stratum corneum
the epithelium is 600-800 µm thick. This is considerably deeper than the epidermis of the skin (the exact thickness varies with site, age and species).

Therefore, to target organelles within cells at the basement membrane of the epithelium, a depth $D_c$ of 600-800 µm is required.

2.3 Lung Delivery

The epithelial cells on the lining of the lung are the target for various gene therapy approaches. These cells are underneath a mucous/liquid lining, which may be 10-100 µm thick. Therefore this lining needs to be overcome. In the example of gene therapy for the treatment of Cystic Fibrosis, this lining is to be overcome to target celial cells on the surface of the epithelium.

2.4 Other Internal Organ Delivery

Cells within other the internal organs can also be targeted for a range of applications, such as:
Internal cancers
Liver (e.g. for Malaria treatment)
Heart (e.g. for angiogenesis blood vessel formation).

2.5 In-Vitro Delivery

Tissue, cell-lines, tissue culture, excised organs, tissue engineered constructs and artificial tissues may also be targeted, in-vitro. Examples include:
stimulation of cell lines and cell monolayers in culture.
stimulation/delivery of growth factors and/or genes (e.g. in tissue engineering and wound healing).

3. Constructional Features of the Micro-Nanoprojections

3.1 General Micro-Nanoprojection Dimensions

With typical cell and organelle scales described and locations in tissues highlighted, the structural terms of the nanoneedles individually are described, and then as examples of arrays for targeting cells at different tissue sites.

Figure 20:
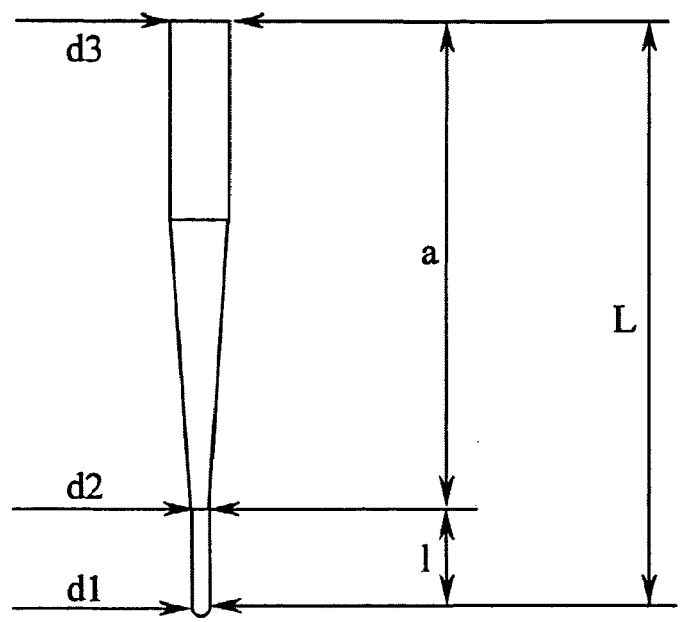
FIG. 20 illustrates the shape and dimensions of examples nanoneedles.

Nanoneedles are configured to penetrate the cell membrane with minimal damage, targeting the organelles of interest. The overall dimensions of the nanoneedle projection are shown in FIG. 20. The nanoneedle is divided into two main sections:

3.1.1 The Targeting Section, Length (L)

Referring to FIG. 20, the radius of the tip (r) is to be as small as practicable with limits set by manufacturing methods and material considerations, where usually the diameter at the distal end of l is $d_1$. Usually $d_1 \sim 2r$. The diameter of the upper end of l is defined as $d_2$. Over the length l, the effective diameter, tapering from $d_1$ to $d_2$ is to be considerably less than the diameter of the cell ($d_{cell}$) or other target. It is shown in Table 1 approximately that 10 µm<$d_{cell}$<30 µm. So, approximately, $d_1$<<10 µm, preferably <1 µm, ideally in some cases <500 nm. Ideally, the scale of $d_1$ is to be of the order of the organelle of interest.

For practical engineering and manufacturing and purposes (e.g. buckling/loading/fracture) it is often preferred that the projection along l tapers out to a larger diameter ($d_2$>$d_1$) that still is less than the diameter of the cell (<$d_{cell}$). However, along the length of l, the profile may be configured such that the diameter is constant (i.e. $d_1$=$d_2$).

The length of the targeting section (l) is sufficient to ensure that the organelle of interest is targeted (i.e. l>organelle dimension). For example, in targeting the cell nucleus, l>3-6 µm). Ideally, l is even longer to account for variation in cell depth location (e.g. as shown by the variation in the Langerhans cell depth Figure A) and increase the probability of the desired needle-organelle contact. The upper length of l is determined by the combination of material properties, needle shape and loading to ensure that the needle does not break under mechanical loading. Engineering analyses shows this mechanical loading is mostly compression, with tension and bending moments. Good engineering practice to ensure the material does not break includes Euler buckling, fracture mechanics, and work-to-failure. In considering a population of projections in an array, statistical methods (e.g. Weibull statistics) and other related methods may be applied to ensure a very small fraction of the projection population breaks.

Consider, as an example, the case of compression loading with the primary mode of projection failure is by buckling. This compression buckling criteria set by the Euler Bucking force ($P_{cr}$)

$$P_{cr} = \frac{\pi^2 EI}{4l^2}$$

where (E) is the Young's modulus of the nanoneedle material, I is the moment of inertia (I=

$$\frac{\pi d^4}{64}$$

for a cylinder). Therefore the material properties of the nanoneedle and shape determine the maximum force permitted for buckling ($P_{cr}$). Good engineering practice dictates that $P_{cr}$ must be less than the insertion force of the needle, to ensure it does not break.

3.1.2 Support Section of the Micro-Nanoprojection (A)

Referring again to FIG. 20, the support section of the micro-nanoprojection (a) is sufficient to bring the targeting section of the cell (l) into contact with the cells/organelles of interest. The diameter of the support section along the length a tapers at the distal end from $d_2$ to $d_3$ at the base, where usually engineering and material considerations result in $d_3$>$d_2$ to ensure it does not buckle or break by another mode of failure. In some cases, the diameter along the length of a may be constant (i.e. $d_3$=$d_2$). FIG. 20 shows that a, l and the overall length of the projection (L) are related by:

$$L=a+l$$

In section 2 the depths of cells for various applications in intradermal, mucosal, lung and internal organ delivery are outlined. The rationale and approximate values of a for targeting these individual sites are presented as examples.

In epidermal delivery, a is the sum of the desired depth in the tissue and an allowance above the target (for instance for tissue surface curvature). This dimension in epidermal delivery is usually <200 µm in length, and preferably <100 µm in length-depending on the tissue species and site. In the targeting of dermal cells, this depth is even greater with a <1000

μm, and preferably <600 μm. In another example, the targeting of basal cells in the epithelium of the mucosa, an a of 600-800 μm is required. In lung delivery, the local barrier of the mucous lining to the cells is 50-100 μm thus a would be of the order of 100 μm in this case.

3.2 Specific Applications

3.2. 1 Example 1

Targeting the nuclei of LC in the viable epidermis, 40-50 μm deep in the tissue. The force to insert the needle is estimated with the Unified Penetration Model (proposed by Dehn J: A unified theory of penetration. International Journal of Impact Engineering, 5:239-248.1987).

$$F_{insert} \approx 3A\sigma_y = 3\frac{\pi}{4}d^2\sigma_y$$

where $\sigma_y$ is the yield stress of the tissue.

Assume, in the highest loading case, the upper value of the yield stress of the SC of 20 MPa applies to all the skin (from Wildnauer R H, Bothwell J W, Douglas A B: Stratum corneum properties I. influence of relative humidity on normal and extracted stratum corneum. Journal of Investigative Dermatology, 56(1):72-78. 1971). Note, this estimate of insertion force is a factor of 10 greater than calculations inferred from measurements with a probe in the skin (unpublished results, by Crowley (2003, 4$^{th}$ Year Project, Engineering Science, University of Oxford).

By setting $F_{insert}=P_{cr}$ we arrive at $$l = \left(\frac{\pi E d^2}{192\sigma_y}\right)^{0.5}$$

which approximates the Euler Buckling relationship between the maximal permissible length of extension for a probe of diameter d, constructed of a material with a Young's modulus (E), penetrating into a tissue with a Yield Stress ($\sigma_y$).

Figure 21:
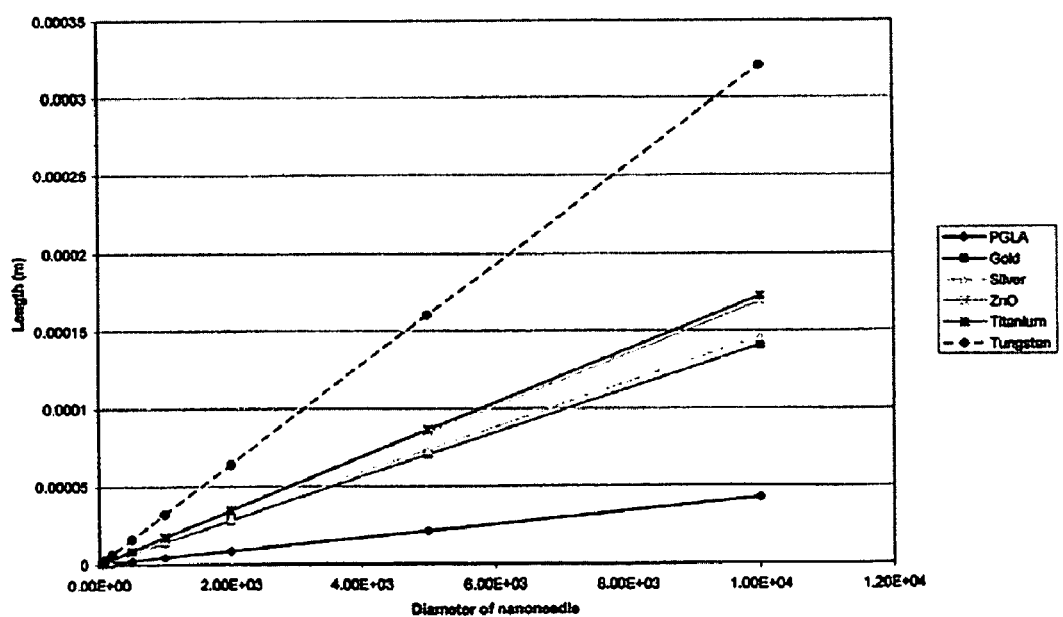
FIG. 21 illustrates the maximum needle length vs. nanoneedle diameter calculated using expression (3) and the Young's Modulus (E) values for Gold, Titanium, ZnO, PGCA, Silver and Tungsten (respectively: 77.2, 116, 111.2 and 7 GPa)

FIG. 21 plots the cell/organelle targeting section length (l) as a function of diameter for six materials. Note that these are upper limit calculations of the loading effects.

Consider the curve for titanium (E=116 GPa) in which a 400 μm diameter ($d_1=d_2$) cell/organelle targeting section corresponds to a length of 7 μm, and a 1 μm diameter corresponds to a maximum length of 14.1 μm. In this case, the nucleus of the LC is the organelle of interest with a size of 3-6 μm. Here, we choose a organelle targeting section of $d_1=d_2=1$ μm and a length (l) of 10 μm (symbols corresponding to the diagram of FIG. 20). The support length (a) is 40 μm, tapering to a base diameter ($d_3$) of 5 μm. These dimensions are summarised in Table 2.

Alternatively, a nanoneedle constructed of a stiffer material such as silicon (E=189 GPa) results in a smaller cell/organelle targeting section of $d_1=d_2=200$ nm over a length (l) of 5 μm. Of course, a brittle material such as silicon would also require fracture (and other) analyses that may lead to more conservative (i.e. larger) dimensions—these numbers throughout this section are simply illustrative.

Utility of an even stiffer material such as Tungsten (E=400 GPa) results in the same nanoneedle diameter of $d_1=d_2=200$ nm extended over a length (l) of >6 μm—or alternatively the possibility of a smaller diameter $d_1=d_2<200$ nm for a length of 5 μm.

3.2. 2 Example 2

Targeting the Endoplasmic Reticulum LC of the Viable Epidermis. Table 1 lists the thickness of the Endoplasmic Reticulum envelope to be 75 nm. Choosing titanium, the organelle targeting section is set at 400 nm over a length of 5 μm. As shown in Table 2, the remainder of the components are identical to those set out in Example 1.

3.2. 3 Example 3

Targeting cell nuclei at a depth of 600 μm in the tissue. Here, the targeting section is identical to Example 1, whereas the considerably longer length (a=600 μm) requires a significantly wider base ($d_3=50$ μm).

3.2. 4 Example 4

Figure 28:
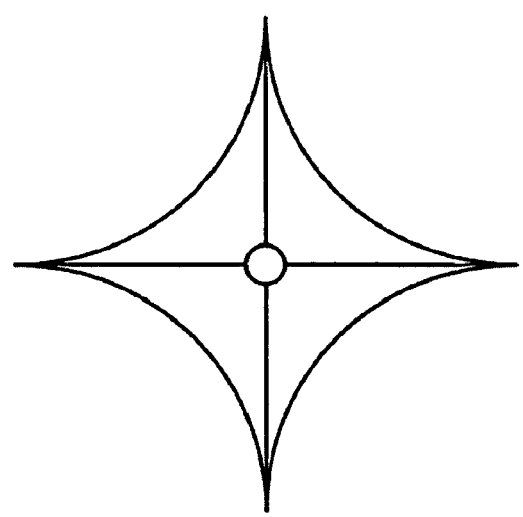
FIG. 28 is a plan view diagram of possible alternative geometry of the nanoneedle.

FIG. 20 shows an axi-symmetric design for the nanoneedle. Alternative shapes may be used with:
higher values of mass-moment of inertia (I)
more knife-like geometries with sharper leading edges.
One possible example of an alternative shape taking on these features is shown in plan view in FIG. 28.

TABLE 2

The geometry of three nanoneedle examples.

| Example | r (nm) | $d_1$ (nm) | $d_2$ (nm) | l (μm) | $d_3$ (μm) | a (μm) |
|---|---|---|---|---|---|---|
| 1. Nucleus of LC, 40-50 μm deep | <1000 | 1000 | 1000 | 10 | 5 | 40 |
| 2. Endoplasmic Reticulum of LC 40-50 μm deep | <400 | 400 | 400 | 5 | 5 | 45 |
| 3. Cell nuclei, 600 μm deep. | <400 | 1000 | 1000 | 10 | 50 | 600 |

4. Route For Transfer Of Bioactive Material To End Point (Coating)

Consider the generic shape of the micro-nanoprojection (FIG. 20). The bioactive material is coated to the outer surface of the micro-nanoprojection. The following lists two example protocols on how this is done, followed by a list of possible coating combinations.

4.1 Coating DNA on Metallic (e.g. Gold or Tungsten) Micro-Nanoprojections

Consider the case of coating eGFP to tungsten micro-nanoprojections. Essentially, published and well established protocols devised for coating gold microcarriers for biolistic delivery are employed. Examples of these protocols are detailed in:

PowderJect and Bio-Rad patents and protocols such as: http://plantsciences.montana.edu/wheat-transformation/biolisti.htm); J. E. Biewenga, O. H. Destree, L. H. Schrama, "Plasmid-mediated gene transfer in neurons using the biolistics technique", J. Neurosci. Methods 71 (1997) 67-75; S, Novakovic, M. Knezevic, R. Golouh, B. Jezersek, "Transfection of mammalian cells by the methods of receptor mediated gene transfer and particle bombardment", J. Exp. Clin. Cancer Res. 18 (1999) 531-536; H. Wellmann, B. Kaltschmidt, C. Kaltschmidt, "Optimized protocol for biolistic transfection of brain slices and dissociated cultured neurons with a hand-held gene gun," J. Neurosci. Methods 92 (1999) 55-64; and, John O'Brien, Sarah C. R. Lummis "An improved method of preparing microcarriers for biolistic transfection", Brain Research Protocols 10 (2002) 12-15.

In this example, subsequently applied to the Experimental Exemplificaton 1 (section 5.3) the protocol of O'Brien and Lummis (2002) is applied.

Alternatively, in coating silicon, protocols developed for the sub-micron patterning of DNA oligonucleotides for "lab-on-a-chip" technology can be applied to coating the projections on the array (H. B. Yin, T. Brown, J. S. Wilkinson, R. W. Eason and T. Melvin (2004) "Submicron patterning of DNA oligonucleotides on silicon" Nucleic Acids Research, 2004, Vol. 32, No. 14 el 18). This process is an example of two-stage process for the covalent attachment of DNA oligonucleotides onto crystalline silicon (100) surfaces. In summary, UV light exposure of a hydrogen-terminated silicon (100) surface coated with alkenes functionalized with N-hydroxysuccinimide ester groups result in the covalent attachment of the alkene as a monolayer on the surface. Submicron-scale patterning of surfaces is achieved by illumination with an interference pattern obtained by the transmission of 248 nm excimer laser light through a phase mask. The N-hydroxysuccinimide ester surface act as a template for the subsequent covalent attachment of aminohexyl-modified DNA oligonucleotides. Oligonucleotide patterns, with feature sizes of 500 nm, are reliably produced over large areas. The patterned surfaces are characterized with atomic force microscopy, scanning electron microscopy, epifluorescence microscopy and ellipsometry. Complementary oligonucleotides are hybridized to the surface-attached oligonucleotides with a density of $\sim 7 \times 10^{12}$ DNA oligonucleotides per square centimeter (for example).

Some-possible coating combinations include:
- No coating: The cell is perturbed/stimulated by the physical disruption of the micro-nanoprojection structure. This physical stimulus can be coupled with electric stimulus as a form of specific nanoelectroporation of particular organelles or the cell.
- Coating entire nanoneedles: The bioactive material can coat the whole surface of the nanoneedle (over the length L).
- Selective coating: For certain applications only parts of the nanoneedle need be coated. For instance, the targeting section (l) can be selectively coated by only immersing this part of the needle in the coating media. Alternatively, different combinations of various coatings can be made on the one nanoneedle (combinations of DNA and adjuvants, proteins, cytokines, inhibitors etc). Or, in the case of nanoneedle arrays, different coatings may be provided on different individual micro-nanoprojections.
- Coating materials: In addition to bioactive materials (such as DNA, RNA and proteins), the micro-nanoprojections may also be coated with nanobiosensors (e.g. quantum dots, nanomachines, MEMS) using a range of coating protocols.
- Material formulated in degradable micro-nanoprojections: All, or part of the micro-nanoprojection can be constructed of a biocompatible, biodegradable polymer (such as Poly Lactic Acid (PLA), Poly Glucleic Acid (PGA) or PGLA), which is formulated with the bioactive material of choice. The micro-nanoprojections may then be inserted and, as they dissolve, the bioactive material will enter the organelle(s)/cells.

In the cases of bonding of the biomaterials to the surface of the micro-nanoprojections, access to the organelles may be by the following:

- The bioactive material can stay on the surface of the nanoneedle, but elicit the response within the organelle/cell.
- The bioactive material bonds can be broken by exposure of enzymes, proteins or hydration within the cell/organelle.

5. Experimental Exemplification 1

This section outlines the simplest embodiment of the nanoneedle concept: an individual projection, coated on the surface with a bioactive material (here DNA coded for GFP transfection), used to deliver this material to a living cell, in-vitro, where a biological response is measured (transfection) and the cell is alive.

5.1 Fabrication of Micro-Nanoprojection

Following the engineering analyses discussed in section 3, Tungsten was selected as the material for fabricating the individual nanoprojection, largely because of its high stiffness (E=400 GPa) and ease of fabrication.

Individual micro-nano projections were fabricated from tungsten rod of diameter 280 μm (Source, ADVENT Research Materials Ltd) using electropolishing (approximately following the protocol of Cerezo, A., Larson D. J. & Smith G. D. W. (2001) "Progress in the atomic-scale analysis of materials with the three-dimensional atom probe". *Materials Research Society Bulletin*, 26(2):102-107.

Figure 22:
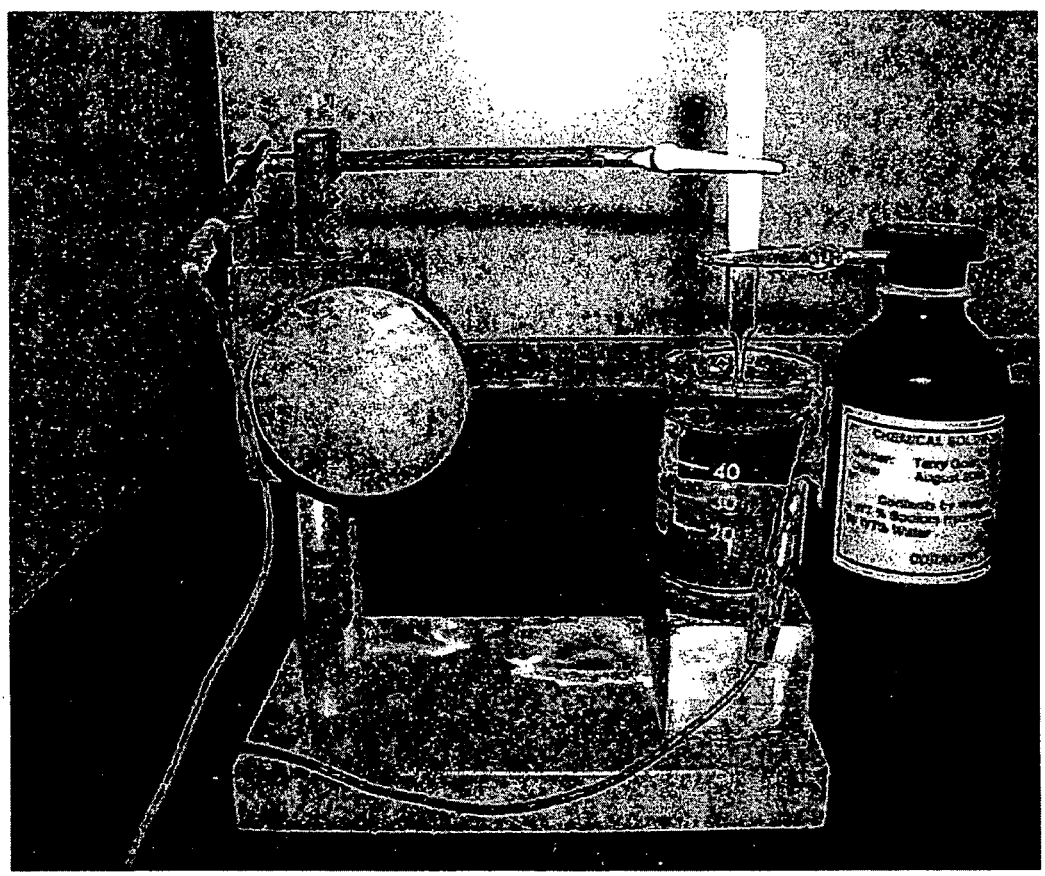
FIG. 22 is a photograph of the electropolishing set-up for fabricating individual tungsten micro-nanoprojections.

A photograph of the electropolishing set-up is shown in FIG. 22, with the electrical leads connected to an A/C power supply (not shown). The solution in the beaker was distilled water with 4% NaOH molar. For the electropolishing tungsten probes with the sharpest tips, the following settings were used:

3 mm of probe submersed into the solution
10 volts A. C. for approx. 42 seconds.

Following optimisation, electropolishing was ceased when probe length began to diminish (detected by visual sighting by naked human eye).

5.2 Example of Individual Electropolished Projections

Recall the dimension parameters correspond to the generic micro-nanoprojection tip outlined in the schematic of FIG. 20.

Figure 23A:
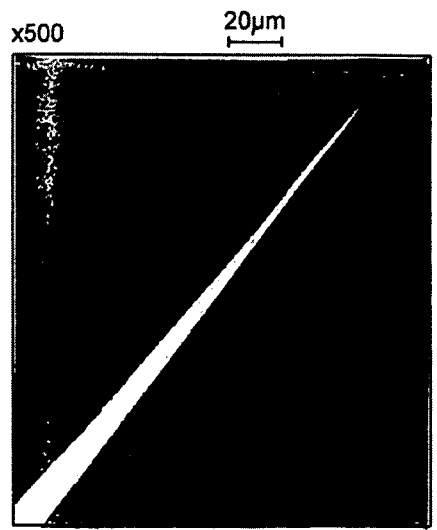
FIG. 23 is a Transmission Electron Micrographs (TEM) of a micro-nanoprojection electropolished from tungsten at (a) X 500 magnification and (b) 88000 magnification.
Figure 23B:
Figure 23C:
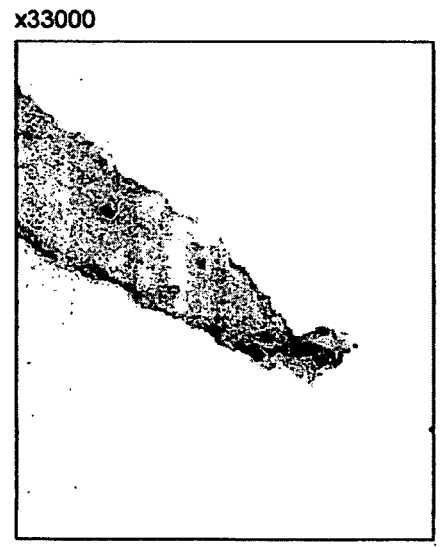

FIG. 23 shows Transmission Electron Microscopy (TEM) of an electropolished Tungsten tip at two different resolutions, with the scale bar in (a) of 20 μm, and in (b) of 0.11 μm. FIG. 23 (b) shows the minimum tip size ($d_1$) is ~100 nm (i.e. r~50 nm) By using the electropolishing process, the projection gradually tapers to the full thickness of the original rod (i.e. $d_3$=280 μm). In this case, the cell targeting length (l) is approximately 20 μm-defined by where the diameter ($d_2$) remains less than ~1 μm.

Individual micro-nano projections were glued into hole drilled into perspex cylindrical holders to allow fitting into microprojection systems (see section 5.5).

5.3 Coating of Micro-Nanoprojections with eGFP DNA Plasmid

The tungsten micro-nanoprojections were coated by adapting a protocol devised for the coating of gold microparticles for biolistic delivery developed by O'Brien and Lummis (2002) "An improved method of preparing microcarriers for biolistic transfection", Brain Research Protocols 10 (2002) 12-15. The adapted protocol is as follows:

(i) Coat tungsten micro-nanoprojection in 50% glycerol/ 50% water solution by dipping the wire in the solution for 10 minutes.
(ii) Remove the tungsten.
(iii) Individual tungsten micro-nanoprojections were placed in a tube to which was added 50 ml of 1 M spermidine for 5 minutes.
(iv) Add 1 µg/ml of 50 ml of DNA Spermidine and gently mix the two solutions with aspiration with the wire in the solution.
(v) Gently, the tube was stirred for a few minutes, and then, whilst stirring, 1 M CaCl in solution was added in a drop wise manner.
(vi) Gently mix the solution and let DNA precipitate on to the wire for 30 minutes.
(vii) Remove wire from solution and dip it in 100% ethanol. Repeat this process 3 times.
(viii) Let the wire dry before use.
(ix) The process was then repeated for the other micro-nanoprojections.

Figure 24A:
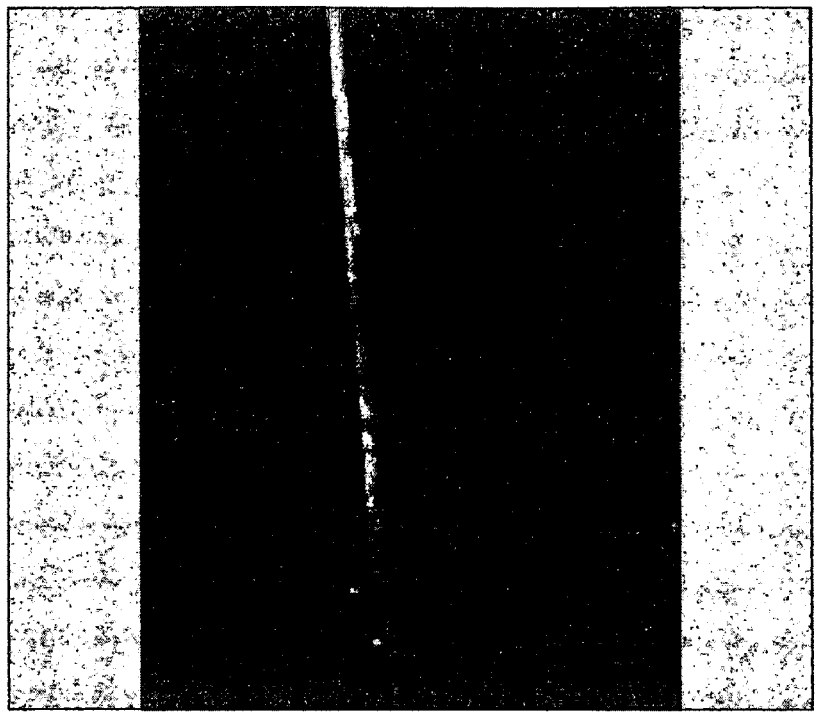
FIG. 24 illustrates fluorescent microscope images of tungsten rods, (a) uncoated and (b) coated in eGFP plasmid DNA immersed in an ethidium bromide solution.
Figure 24B:
Figure 25A:
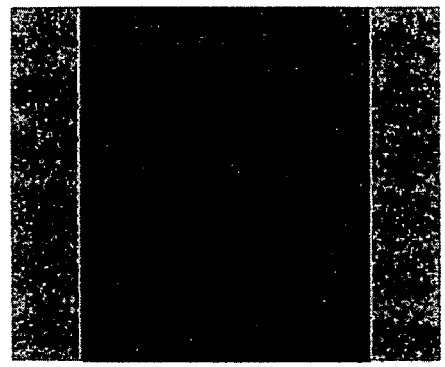
FIG. 25 is an example of an optically sectioned Multi-Photon Microscopy (MPM) images of the agar after insertion of a DNA coated tungsten probe (a) on the surface (b) at a depth of 13 μm (c) at a depth of (32 μm). Also shown in (d) is an optical section at 32 μm of agar gel following insertion of a probe without a DNA coating.
Figure 25B:
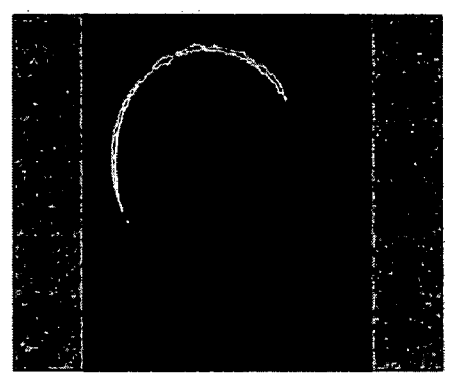
Figure 25C:
Figure 25D:
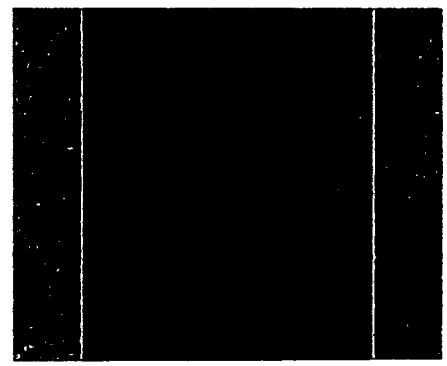
Figure 26:
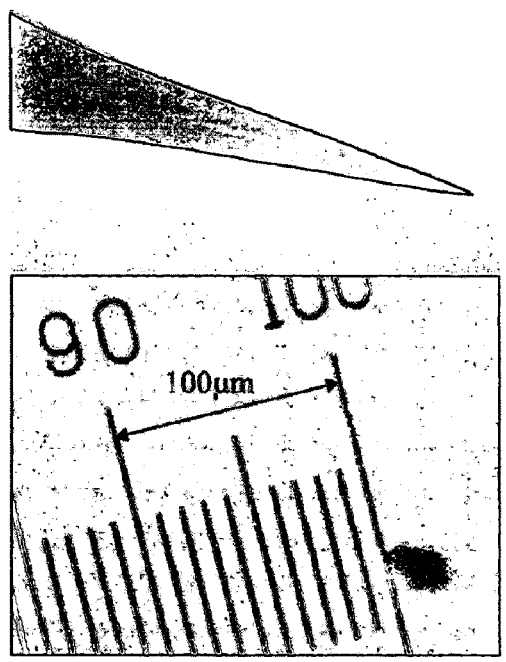
FIG. 26 illustrates a photomicrograph of a micro-nanoprojection electropolished from tungsten used in skin tissue indentation experiment with scale bar.

FIG. 24 shows images of lengths of tungsten wire (280 µm diameter) imaged with a fluorescent microscope with (a) uncoated wire and (b) DNA coated wire (using the described protocol, above) immersed in a liquid with a propidium iodide stain (red fluorescing dye). As expected there is no red fluorescence with the uncoated wire, while the strong red fluorescence of the NDA coated tungsten qualitatively shows that the coating was successful.

5. 4 Assessment of Delivery into In-Vitro Test Bed

To assess the delivery profile of DNA in the in-vitro equivalent of skin tissue, DNA coated projections were inserted into an agar (3%) gel stained with acridine orange (green fluorescing dye). This gel (without the stain) is routinely used for in-vitro testing of biolistic devices for DNA vaccination and other applications.

The uncoated and coated tungsten rods were inserted and removed by hand into the agar (to a depth >1 mm) for a cycle duration of approximately 1 second.

FIG. 25 shows optically sectioned Multi-Photon Microscopy (MPM) images of the agar after insertion of a DNA coated tungsten probe (a) on the surface (b) at a depth of 13 µm (c) at a depth of (32 µm). Also shown in (d) is an optical section at 32 µm of agar gel following insertion of a probe without a DNA coating.

On the surface of the agar, there is very little fluorescence, indicating little DNA. In contrast, at depth sections of 13 µm and 32 µm the fluorescence in the coated case is significant-indicating that DNA remained intact on the surface of the probe during insertion and then came off by exposure of the gel and/or by the action of removing the probe. This fluorescent signal was very strong compared with the uncoated probe control at 32 µm.

5.5 Experiment of DNA Delivery into a Cell

The described electropolished tungsten micro-nanoprojections coated with GFP plasmid DNA were tested, with the objective of determining whether the DNA could be delivered to transfect the cell, without damaging the cell.

The cell line is called A549 which is a human lung carcinoma (epithelial) cell line. Cells were cultured in Dulbecco's modified eagle medium (DMEM) supplemented with 10% fetal calf serum at 37° C., 5% $CO_2$.

These cells were mounted on three separate Petri dishes with an optical slide underneath. The adherent properties of the cells ensured they remained in contact with the base of the dish.

One of the Petri dishes with cells was set aside as a control. The other two Petri dishes were probed with the micro-nanoprojections. In total, 6 micro-nanoprojection systems were used.

Probing of the cells was performed with a microinjection system (Eppendorf Femtoject and Injectman NI2 microinjection kit) fitted to an inverted fluorescent microscope (Zeiss Axiovert 25 microscope with stage heater).

The micro-nanoprojection were fitted into the standard microinjection holder and then moved with course and fine adjustment of a motorized X-Y-Z axis controller to just contact the cell membrane, before retraction of less than 1 µm.

A cycle time of probing was set between limits of 0.1 and 15 seconds, with a traverse distance of 3-5 µm-then the cycle was automatically performed on the system.

After 3 cells, the probe was replaced and refitted with a replacement. In total 10 cells were perturbed with a micro-nanoprojection coated in eGFP plasmid DNA.

All the cell samples were then incubated for 24 hours before viewing with a widefield fluorescent microscope, with the appropriate fluorescent filters. The observed results show: in the control there is no sign of eGFP transfection, as expected. However, in the cell micro-nanoprojection cases, we see that 10 cells have transfected. Thus we have a 100% transfection efficiency and no evidence of cell death.

These data prove the micro-nanoprojections, coated in DNA can individually target cells, transfecting them and not kill them.

Also, subsequent analysis of the micro-nanoprojections showed they remained intact, illustrating that unlike biolistic delivery, the "carrier" material is not left behind.

6. Experimental Exemplification 2

With the biological result achieved on a single cell, in-vitro (Experimental exemplification 1). this section outlines a logical progression, which is the physical testing of an individual micro-nano projection into a representative skin sample for structural integrity-thereby testing the engineering analyses outlined in section 3.

6.1 Experiment Design

Using the electroporation process described in Embodiment 1, a micro-nanoproprojection was fabricated of Tungsten with a tip radius (r) of <400 nm.

The tissue was freshly excised Balb/C mice ears (age 8-10 weeks), which were glued to a metal cylinder holder. The reported stratum corneum and viable epidermis thicknesses of these samples are respectively ~5 µm and 12 µm (Arbuthnott (2003)).

Figure 27:
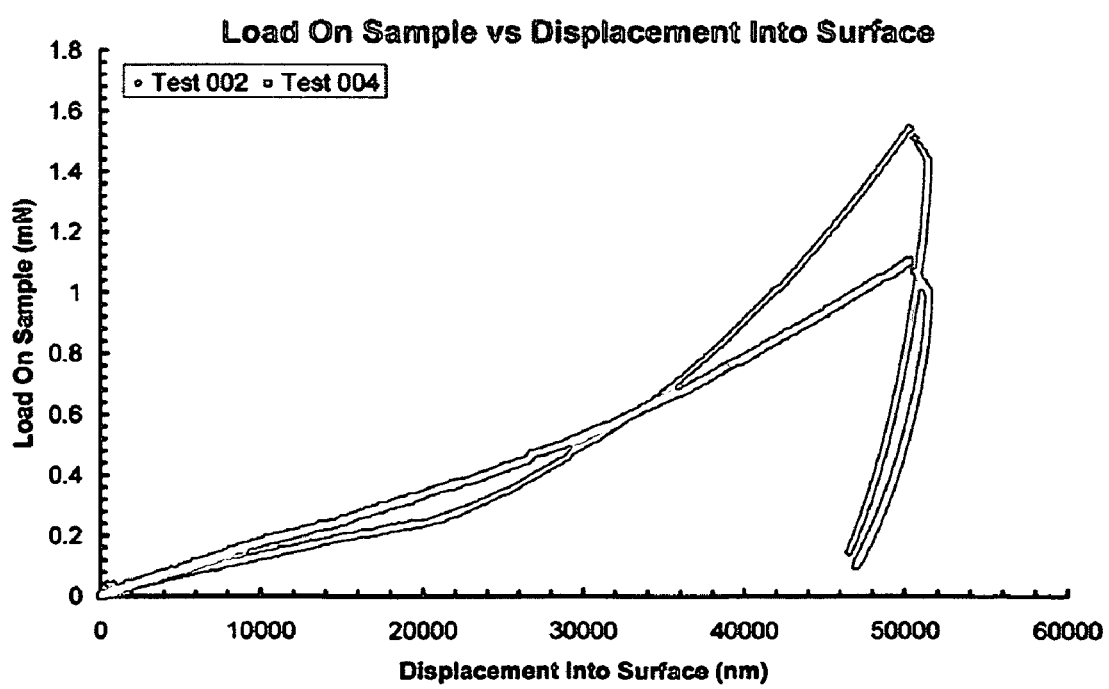
FIG. 27 illustrates two sample load-displacement curves in freshly excised mouse ear tissue obtained with the micro-nanoprojection shown in FIG. 26.

The tissue was indented by fitting the micro-nanoprojection to a Nanoindenter (MTS systems, UK), measuring a force displacement curve. FIG. 27 shows two typical sample results of loading-unloading curves achieved to a depth of ~50 µm. These results show that the micro-nanoprojection probe penetrated through the epidermis and well into the dermis without damage. The difference in magnitude between the curves is typical of biological variability observed in bio-viscoelastic tissue. Importantly, unlike ballistic particle delivery, the depth of penetration is not dependant upon this variability-rather the length of projection.

Indeed, the projections did not break—the loading experiment was simply stopped at a 50 μm setting on the experimental apparatus. This was confirmed by imaging with projections with a microscope after the experiment. This experiment was repeated 20 times, confirming the engineering analyses of probe structure required to target cells in the skin is applicable and valid.

6. Experimental Exemplification 3

Overall Size Range Of Individual Patch

With the biological and engineering criteria investigated on an individual projection, the next logical step is to extend the concept to arrays of patches targeting tissue sites. Presented are several patch arrangements, each designed for a particular targeting need of cells, organelles and/or tissue sites.

6.1 General Dimensions and Design of Patch

Figure 29:
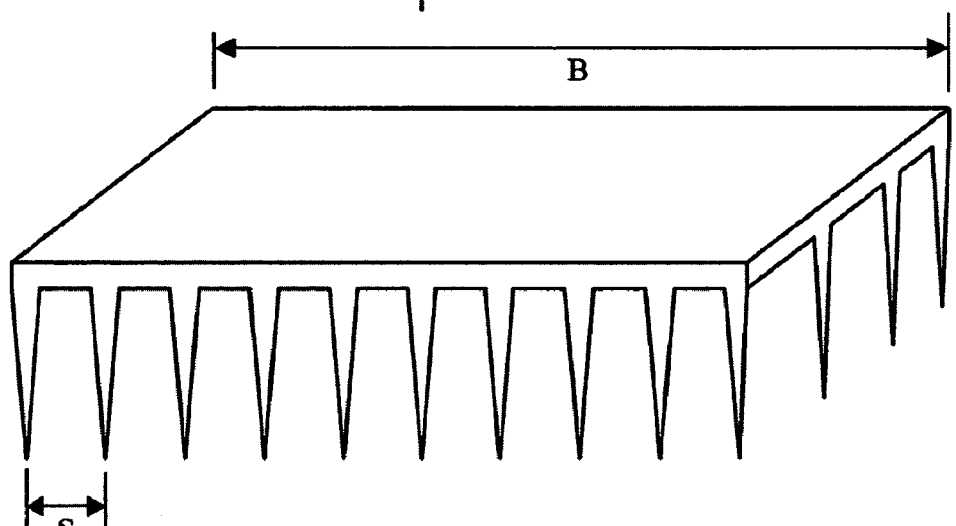
FIG. 29 illustrates an example of a nanoneedle array or patch device.

FIG. 29 shows a schematic of an array of the described micro-nanoprojections configured on a patch, with the spacing between micro-nanoprojections defined as (S) and the patch breadth defined as (B). Recall, the basic dimensions and definitions of an individual micro-nanoprojection are outlined in section 3 and shown schematically in FIG. 20; these are referred to again here.

Operation of the patch with the micro-nanoprojections is, for example:
(a) the slow insertion, by hand (or other means, such as a spring) of the patch onto the tissue, with the micro-nanoprojections inserting into the target tissue of interest.
(b) the patch including the micro-nanoprojections are held in place for a sufficient time for the "event" (biological, physical or other) to take place. This may be instantaneous, or in other cases could take days, weeks or months.
(c) the patch including the micro-nanoprojections are then retracted.

These three stages form a cycle, that may be operated by hand or automated with the aid of suitable mechanical, electrical or electro-mechanical devices.

Patches may be applied to the tissue site once, or a multitude of times depending upon the effect desired.

The case examples presented in 6.2 all centre on the targeting of Langerhans cells or organelles within these cells and the overall dimensions of the individual micro-nanoprojections are configured, using the approximate guideline of Example 1 and 2 shown in Table 2. However, as Table 2 also shows, these parameters (r, $d_1$, $d_2$, $d_3$, a) can vary significantly, depending on the cell/organelle and its position relative to the tissue surface.

6.2 Case Examples of Patch Configurations

The overall size (B×B) of the patch and spacing (S) between the micro-nanoprojections is determined by the application. Note, in all cases, the patch could be square (B×B), circular, elliptic, or any other suitable shape. For simplicity, the square dimensions are quoted throughout. Generally the size is to be less than 15×15 mm (B), with 1<S<1000 μm, preferably with 10<S<200 μm.

Note that an alternative for these and other patch examples is for larger-patches, giving amplified responses and/or which may be easier to handle having regard to end users/patients/practitioners.

6.2.1 Targeting LC Nuclei

Consider Example 1 from Table 2, which is the targeting of nuclei of Langerhans cells. Kendall et al. (2003), Kendall M. A. F., Mulholland W. J., Tirlapur U. K., Arbuthnott E. S., and Armitage, M. "Targeted delivery of micro-particles to epithelial cells for immunotherapy and vaccines: an experimental and probabilistic study", The 6th International Conference on Cellular Engineering, Sydney, August 20-22), suggest that to trigger cellular responses in DNA vaccination, of the order of 100 nuclei of LC are effectively transfected in gene gun applications that lead to the desired cellular (MHC 1) systemic response. A probability analysis has been performed to determine the configuration of patch required to transfect 100 cells. The probability of one micro-nanoprojection making contact with an organelle (or cell) defined over an area and volume is set by:

$$P_{contact} = \frac{V_{probe}}{V_{layer}} \cdot \frac{V_{organelles}}{V_{layer}}$$

In the analysis, it is assumed:
that there is no cell death.
the cell/organelle targeting sections (l) are configured to be at the correct depth (i.e. the depth of the Langerhans cells), and, for simplicity, parallel and lira in diameter ($d_1=d_2=1$ μm).
the cell/organelle targeting sections (l) are coated in DNA. Of course, for simplicity of coating, it is possible that most or all of the micro-nanoprojection structure is coated in DNA.
contact of any part of the micro-nanoprojection along the cell/organelle targeting section with the nucleus is the only mode that leads to transfection (i.e. cytoplasm delivery, cross-priming and other modes are ignored).

With a 1 μm diameter cell/organelle targeting section (l), the probability of contact with a LC nucleus is 0.0131. This probability is ~1000-1500 times higher than a typical probability of a direct "hit" with the biolistics approach and micro-particles. Furthermore, the transfection comparison is even more favourable for the micro-nanoprojection patch, given far fewer cells are killed than by the gene gun.

Table 3 is a summary of configurations of patches that may be used. At one end of the range, a spacing of 100 rods/mm² corresponds to a patch surface area of 76 mm², with a spacing (S) of 100 μm, a breadth of 8.7 mm and a total number of rods of over 7000. Increasing density of rods to 1000 mm² results in a reduction in patch size to less than 3 mm×3 mm.

TABLE 3

Calculated patch configurations for the targeting of nuclei of LC.

| Rod/mm² | Area of patch (mm²) | Spacing (S) (μm) | Breadth of patch (B) (μm) | Total Rods |
|---|---|---|---|---|
| 100 | 76.4 | 100 | 8.7 | 7639 |
| 500 | 15.3 | 45 | 3.9 | 7639 |
| 1000 | 7.6 | 32 | 2.8 | 7639 |

6.2.2 Targeting the LC

In Table 4, this analysis is extended to the configuration of patch required to target 100 LC (i.e. anywhere within the complete cell), using micro-nanoprojections with the same geometry as above, with the probability of the event 0.063.

Not surprisingly, this is higher than the probability of targeting the nuclei. Hence, fewer rods are needed and the patch size can be smaller (4×4 mm down to 1.25×1.25 mm).

TABLE 4

Calculated patch configurations for the targeting of anywhere within complete LC.
The nanoneedle diameter $d_1$ is assumed to be 1 μm.

| Rod/mm² | Area of patch (mm²) | Spacing (S) (μm) | Breadth of patch (B) (μm) | Total Rods |
|---|---|---|---|---|
| 100 | 15.8 | 100 | 4.0 | 1578 |
| 500 | 3.2 | 45 | 1.8 | 1578 |
| 1000 | 1.5 | 32 | 1.3 | 1578 |

6.2. 3 Targeting the Endoplasmic Reticulum of the LC

In Table 5, the analysis is also applied to the targeting of the Endoplasmic Reticulum (Example 2 from Table 2), which may be required for targeted RNA delivery. Using the assumptions from above, with a probe diameter of 400 nm the probability of a single needle contacting the Endoplasmic Reticulum is 0.031. In this case, the size of patch ranges from 8×8 mm to 2.5×2.5 mm.

TABLE 5

Calculated patch configurations for the targeting of the Endoplasmic Reticulum of LC.
The nanoneedle diameter is assumed to be 400 nm.

| Rod/mm² | Area of patch (mm²) | Spacing (S) (μm) | Breadth of patch (B) (μm) | Total Rods |
|---|---|---|---|---|
| 100 | 65 | 100 | 8.0 | 6451 |
| 500 | 13 | 45 | 3.60 | 6451 |
| 1000 | 6.5 | 32 | 2.54 | 6451 |

6.2. 4 A Combination of Micro-Nanoprojection Geometries on a Patch

A patch may also have combinations of micro-nanoprojections, with different geometries. For example the length (L) or indeed the other parameters in FIG. 20 may be varied throughout the patch, either in defined sequences, clusters and/or randomly (within limits). Within this, or separately, the diameter of the projection may be increased on individual micro-nanoprojections significantly in order to induce cell death at controlled locations. This, for example, may be used to induce bystander biological responses (e.g. stimulation/inflammation/activation) to neighbouring healthy cells- which could have or will be interacting with described, smaller micro-nanoprojections configured for minimal cell damage.

7. Specific Bioactives e.g. Nucleic Acids

The bioactive or other stimulus is to be coated or part of the nanoneedle array. The choice of bioactive is determined by the application and target organelles or cells of interest. This range encompasses, but is not restricted to:
No coating
Polynucleotides, DNA (all variants), RNA (all variants), proteins, antigens, allergens and adjuvants, molecules, compounds.
Biosensor molecules and compounds and materials.
Nanosensors (MEMS etc).
Combinations of the above, on a

8. Methods Of Production Of Device

General requirements of the manufacturing method are:
a radial resolution of <200 nm;
to construct the nanoneedle array on a patch (e.g. FIG. 19) in a scaleable process for high throughput manufacturing with minimal human input.
Construction to be of a medical grade material (e.g. Gold, Silver, Titanium, Tungsten or PLA, PGA, PGLA, Silicon)

A range of techniques for micro-nanofabrication methods described in text books, papers and in other literature (e.g. Madou M. J. "Fundamentals of Microfabrication. The science of miniaturization", CRC Press, 2002; McAllister et al. 2003, PNAS, Nov. 25, 2003, Vol 100, number 4) are applicable to the nanoneedle device here.

Furthermore there are a range of materials and fabrication methods being developed that also have potential utility as part of a micro-nanoprojection array. Three construction embodiments are shown here as examples.

Figure 30:
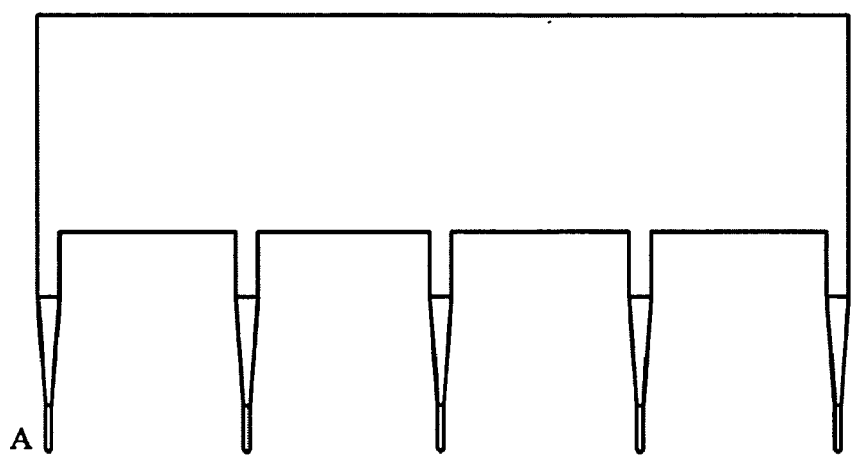
FIG. 30 is a schematic diagram of an example of the nanoneedle array produced with 2PLSM.

In these constructional embodiment example cases, the patch geometry of manufacture is summarised in Table 3, with an area of patch ~76.4 mm², a spacing of 100 μm and the minimum tip size of 1 μm ($d_1$). A schematic of this array on patch is shown in FIG. 30. Of course, the techniques can be applied to a range of geometries.

8.1 Constructional Embodiment Example 1

As an example of the fabrication of silicon micro-nanoprojections, the following is applied. Deep Reactive Ion Etching (DRIE) is used as a process ideal for these high aspect ratio structures, where in one example (Oxford Instruments Plasmalab System 100, Modular ICP180 Etch System—S12), etch rates of >2.5 μm/min, and sometimes >5 μm/min, are possible. Full details of etch protocols for this system are available in the literature, including Oxford Instruments company manuals.

Briefly, chromium was sputter deposited then lithographically patterned as an array of dots onto 3 inch (75 mm) 100 oriented silicon wafers. The array of dots had a centre-to-centre spacing of 100 μm, and in some earlier test cases, 10-20 μm. Similarly, through iteration with the conditions and exploring the extent of undercut, the diameter of the dots 1 μm, and in other cases, 3 μm, 5 μm, and 10 μm. Deep Reactive Ion Etching (DRIE, Oxford Instruments, Bristol, UK) was then carried out to obtain the desired by profile by adjusting the etch rate. The typical instrument conditions included a 20 standard cm³/min (sccm) $SF_6$ and 15 sccm ($O_2$) at a pressure of 20 Pa. Power was varied. The etching process was performed at cryo-cooled conditions, achieving temperatures of −100 to −150° C. Lower etch rates were used for the tapered sections, whereas higher rates were used for the more parallel sections. Micro-nanoprojection fabrication was finished when the chromium masks became fully undercut and fell off the projection tips. The process is completed in less than 100 minutes, resulting in several patch configurations on the wafer.

The patches were then cut from the silicon wafer, with a dedicated cutter.

To increase the strength of the base of the patch, an additional, thicker material is affixed to the back surface (i.e. the surface without the projections).

This process is repeated to fabricate a large quantity of micro-nanoprojection array patches.

A variation of the described DRIE method may also be applied to other materials, including Silicon Carbide (SiC).

8.2 Constructional Embodiment Example 2

This constructional embodiment example applies to a broader range of micro-nanoprojections materials than those described in the constructional embodiment Example 1. These materials include Metals, polymers, silicon and oxides/carbides.

As an example, this case illustrates a method of fabricating tungsten micro-nanoprojection arrays on a patch. Three of the steps in this production process are discussed.

Step 1. Construction of a Template (Male)

To construct a male template with the profile of the micro-nanoprojections, LIGA is used (a German acronym for X-ray lithography, electrodeposition and molding). This template will serve in the production of several molds in a soft polymer. LIGA, which utilizes a Synchroton, is ideal for creating the template because it has a very high resolution (<20 nm), can fabricate in metals, and will easily fabricate a patch (maximum component size is 3.4 inches in the Axsun technologies system). Fabrication protocols to construct the template are detailed in Chapter 6 of Madou M. J. "Fundamentals of Microfabrication. The science of miniaturization", CRC Press, 2002 manuals and literature from companies (e.g. AXSUN Technologies, Ca, USA). The choice of materials for fabrication include Nickel (Ni), Nickel-Iron (NiFe), Nickel-Cobalt (Ni—Co) Gold, Copper and Silver. In this example, Nickel is selected as the material from which the micro-nanoprojection array template is constructed.

It should be noted here that as an alternative, LIGA could be used to make individual patches directly (e.g. of gold or silver-which are both biocompatible) in large quantities. With current costs of the LIGA technology, this is not practical—but with LIGA technology advances, this could be feasible in the future.

Step 2: Construction of a Mask (Female Component)

Figure 31A:
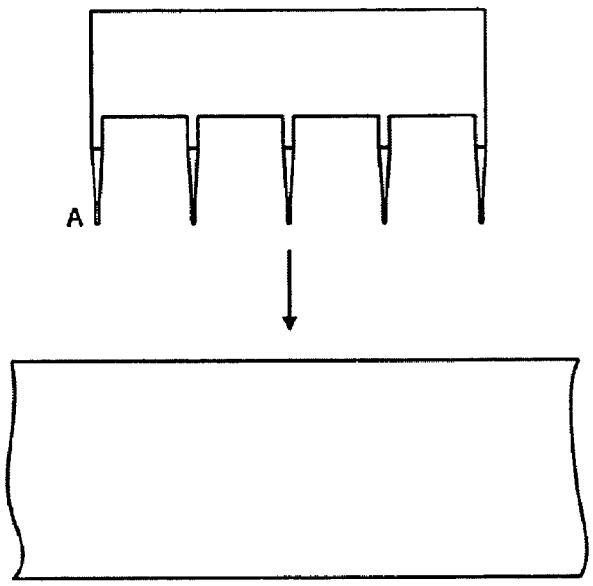
FIG. 31 illustrates a sequence for producing a mask.
Figure 31B:
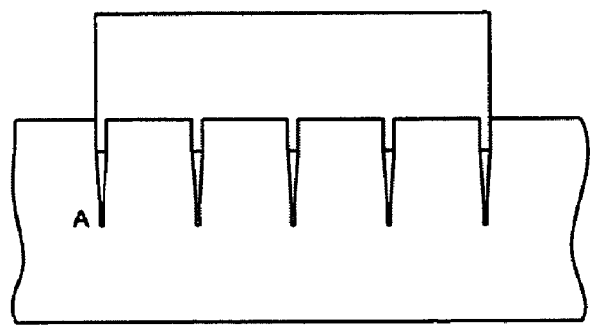
Figure 31C:
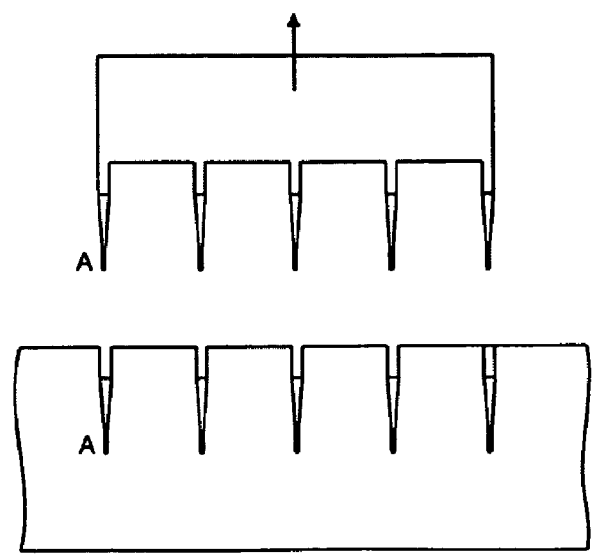

Because of the discussed current characteristics of LIGA (e.g. cost), LIGA is not used to mass-fabricate micro-nanoprojection array patches for direct use with the tissue in large numbers. However, here it can be used as a template for many multi-stage processes. As one examples, the template is used for multiple insertions into a soft polymer to produce a mask, as shown in FIG. 31, performed in the following steps:

FIG. 31 (A) Insertion of the template directly into the soft polymer. This is repeated several times to produce many indentations in the polymer with a given mask.

FIG. 31 (B) Allowing the soft polymer to harden, or "cure" with the addition of catalysts and or temperature.

FIG. 31 (C) Remove the template to leave behind a mask.

Step 3: Final Construction of the Nanoneedle Array with the Mask

The masks are then be placed in a vacuum chamber and deposited with a vacuum deposition/sputtering process. The material to be sputtered is a biocompatible inert material, such as titanium, gold, or silver. In this process, the polymer surface is treated with an air discharge before the chamber is pumped down to a vacuum at 27 degrees C. The titanium, gold or silver film is then deposited. Commercial sputtering machines may be used in this process (such as the VarianVM8 Sputterer).

If a charge is required to produce an anode to enhance the coating of the nanoneedle section, then the end extension of this piece can be "opened up" to expose a stronger anode which the positive charged metallic ions in solution are attracted to. This technique makes use of Magnetron Sputtering.

Step 4: Constructional Embodiment Example 3 Method

The mask can then be removed by immersion of a liquid (e.g. alcohols) to dissolve it.

8.3 Constructional Embodiment Example 3

Alternatively, a mask (female) can be directly manufactured using Two-Photon Stereo Lithography (2PSL), in which the geometry co-ordinates shown in FIG. 31 (C) are applied to construct the desired shape with the photosensitive resin.

Femtosectond two-photon stereo-lithography (2PSL) is described in detail by Miwa et al. (2001, Appl Physics. A 73, 561-566). Zhou et al. (2002, Vol 296, Science), Stellacci et al. (2002, Adv. Mater. 14 (3)) and Halik et al. (2003, Chem. Commun. 1490-1491). This approach has demonstrated the ability to construct complicated 3D shapes with a resolution of <200 nm out of materials including photosensitive polymer resins and metals in conjunction with dyes. Lattice structures of the desired scale have been constructed with the technique using resins impregnated with Silver (from Stellacci et al. 2002).

Briefly, the technique works by scanning with a femtosecond laser in a liquid photosensitive resin bath. The two-photon effect ensures that solidification occurs only where the energy of the laser is concentrated to a femtolitre volume (typically 200 nm×200 nm×400 nm, x, y, z). The method of manufacture is to start at the tip of the nanoneedle (marked A in FIG. 30) and then work up the needle to the base.

The same approach applies to the rest of the nanoneedles. The process is fully automated with a motorised x-y stage with the laser co-ordinates determined from engineering drawings of the structure. Therefore, thousands of nanoneedles can be constructed in a scaleable process. The technique allows complicated 3D structures to be constructed by the scanning of a pulsed (80 MHz), femtosecond pulse length laser concentrating light at 400-1000 nm to a femtolitre volume to induce a two photon excitation of the material and induce solidification.

The nanoneedles may be constructed with a photosensitive polymer/resin, (such as the commercial grade SCR 500) or an alternative impregnated with Silver (following Stellacci et al. 2002).

These materials are currently not suited to be used directly in the skin, due to: insufficient stiffness. Young's Modulus of SCR 500 is 0.49 Gpa compared with 116 Gpa for Titanium or 77.2 Gpa for Gold.

Not medical grade material. At the time of writing, photosensitive resins such as SCR 500 had not gained approval for medical grade purposes.

However, the technique is rapidly improving and may be a possible fabrication method in the future.

8. 4 Constructional Embodiment Example 4

In this case nanoneedles are constructed with silicon, with a 200 nm tip for a length of 5 μm followed by two other parallel sections separated by tapered sections. This structure may be constructed by Electron Beam Lithography and Reactive Ion Etching, a standard technique in the microelectronics industry. The manufacturing approach has been applied by Henry et al. (Journal of Pharmaceutical Sciences 87(8), 1998) and in Lebouitz and Pisano et al. (U.S. Pat. No. 5,928,207) in the construction of microneeedles.

Figure 32:
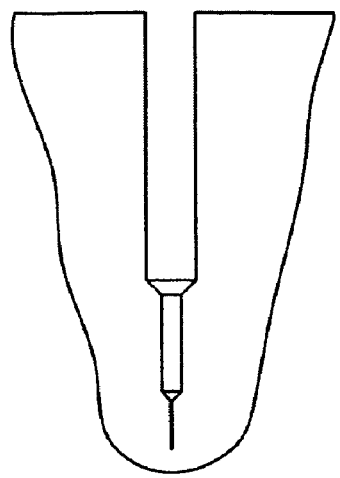
FIG. 32 is a schematic diagram of an example of a "Stepped" nanoneedle.

FIG. 32 shows the structure produced with one of these techniques. In this case of the nanoneedles, each parallel section may be constructed with silicon 100 wafers and the tapered sections constructed with silicon 111 (or other) wafer material—where the angle of the taper is a preferred etching line of the material. The shown shape is made from 5 wafers (one wafer per geometry). A gradual taper mould can be constructed from the one silicon wafer.

Alternatively, the silicon arrays may be used as masters for microarray moulds.

9. Methods Of Treatment

Recall in section 1 the specific target sites of key cells and organelles are described, followed in section 2 by their location within many tissue and in-vitro sites. With the described approach of targeting individual cells, then several cells and the shape/coating/fabrication considerations outlined, the methods of applying these micro-nanoprojection arrays to various tissue sites are now discussed.

9.1 Intradermal Application

With the described embodiments for the skin previously described, the patch is inserted into the skin either by user control or by mechanical, electrical or other controlled means. All these options are possible, as the magnitude of the forces is low. For example, the insertion force is approximately calculated to be less than 1 N (based on 7000 probes, 1 µm in diameter piercing tissue with a yield of 20 MPa).

Similarly, the time of insertion, residence and removal from the tissue can be controlled by user and/or the described mechanical/electrical means.

One embodiment of a simple application system for the patch is shown in FIG. 33.

In this example, the application system 3300 is formed from a structure in the form of a housing or body 3310. The body 3310 defines a cavity 3320 having an opening 3330. In use, a patch 100, having a number of projections 110 provided on a base 120, is moveably mounted within the cavity 3320. This may be achieved in any one of a number of manners, but typically involves having the patch 100 suitable sized to allow movement along the cavity towards and away from the opening 3330.

Figure 33A:
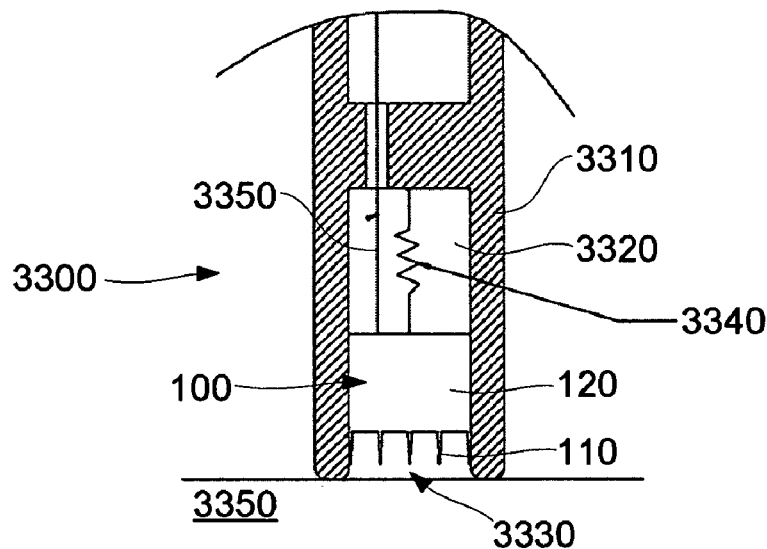
FIG. 33 illustrates an example of an intradermal application of nanoneedle patches.
Figure 33B:
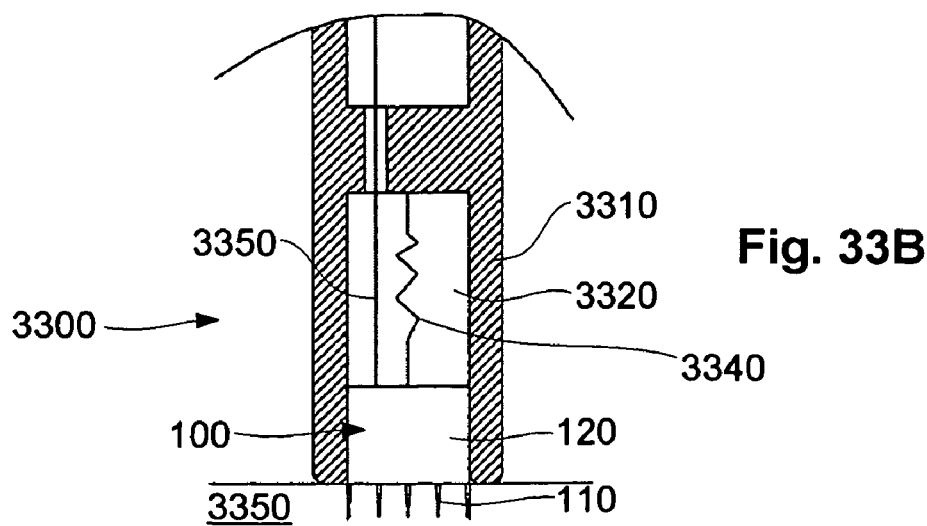

The patch 100 is mounted to an actuator, so that in use the patch may be moved from a retracted position shown in FIG. 33A, to an extended position shown in 33B. The actuator may be of any suitable form, but in one example, includes a spring 3340 and a releasing means 3350.

In the retracted position, the spring 3340 is biased against the patch 100, thereby urging the patch 100 towards the opening 3330, with the patch 100 being retained in the retracted position by the releasing member 3350. When the releasing means is activated, for example, by having an operator release the wire, the spring 3340 urges the patch 100 towards the opening 3330, so that the projections 110 extend therethrough.

It will be appreciated from this that if the structure 3310 is positioned within the opening 3330 adjacent a subject's skin 3360, then operation of the releasing means 3350 causes the patch 100 to be pressed against the subject's skin 3360, so that the projections 110 enter the viable epidermis as described above.

In the retracted position (FIG. 33 (a)) the micro-nano-projections patch is recessed and thus protected, preventing accidental administration. Other packaging/devices may also be used for these purposes, for example a protective cap to be removed before administration.

In this example, the patch is attached to a compressed spring that is held in place by a tensioned string. It will be appreciated that the releasing means typically is arranged so that the patch 100 is retained in the retracted position until the releasing means is activated. Thus, the patch 100 may be retained in position by a clip that is released upon activation of the releasing means. This allows the operator to position the device against the subject's skin 3360 without having to retain the patch in the retracted position. When located on the tissue, the string. is released by a means (e.g. pressing a button, not shown in FIG. 33) and the patch is released to enter the tissue surface (FIG. 33(b)).

9.2 Mucosal Application

To effectively target mucosal sites (e.g. mouth, nasal, rectal, vaginal), the described patch arrangements may be fitted to an applicator designed to safely transport the patch into the mouth and to accurately locate on to the mucosal site. This could be done by using the described intradermal patch in the mouth.

Figure 34:
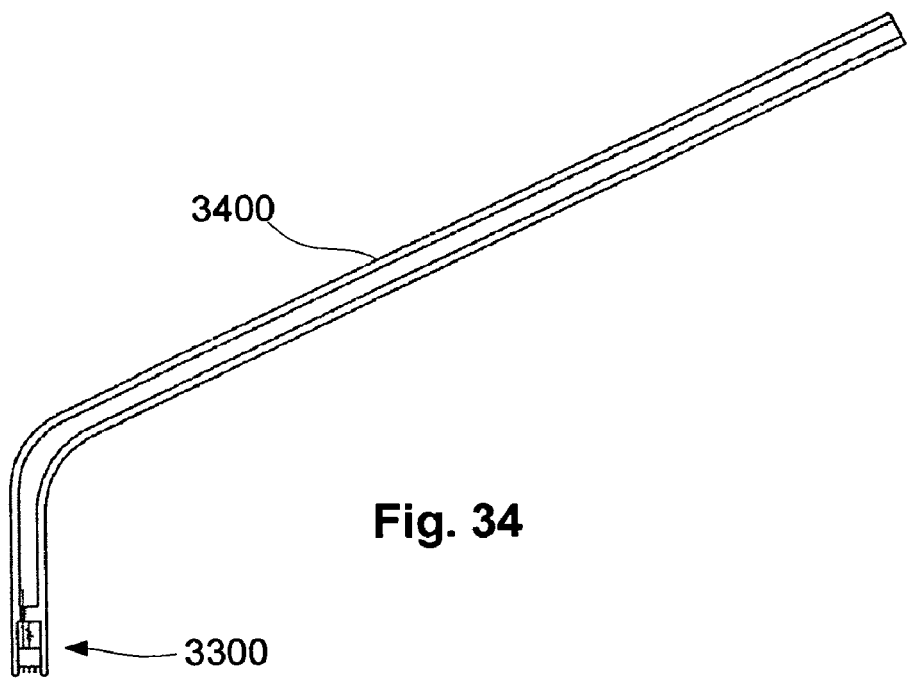
FIG. 34 is a schematic diagram of an example of an applicator, fitted with the patch for mucosal delivery.

Alternatively, FIG. 34 shows one example of and applicator for mucosal delivery for the buccal mucosa (mouth). In this example, the patch arrangement from FIG. 33 in the form of the application system 3300 is coupled to an arm 3400, allowing the application system 3300 to be positioned in otherwise hard to reach places. The spring arrangement allows the patch to be applied, but other mechanisms equally could be used. The applicator could have a button at the distal end of the arm 3400 from the patch to allow the operator to release the patch onto the mucosal site.

Other features may include a knurled surface towards the distal end to aid user grip.

9.3 Lower Airway/Lung Application

Figure 35:
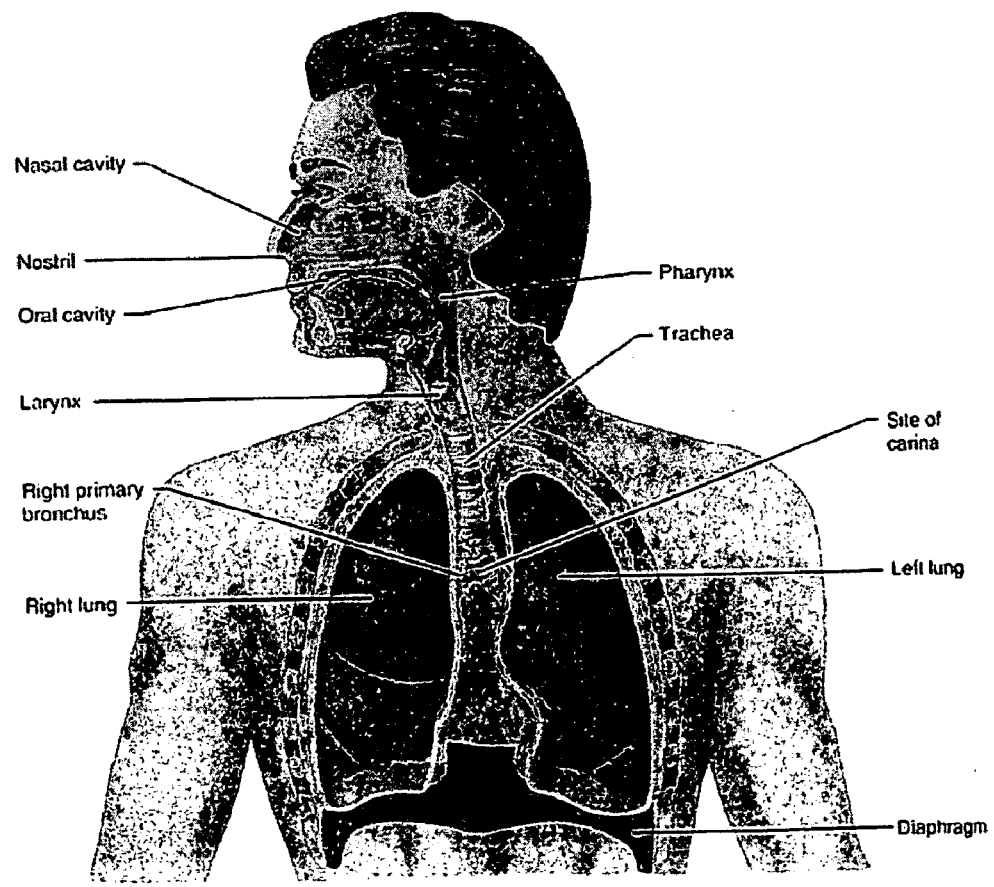
FIG. 35 illustrates the major respiratory organs.

FIG. 35 shows a schematic of the physiology of the airways in a human. To apply the micro-nanoprojections to targeting cells in the tracheal or lung lining, an applicator that can flexibly and compactly reach these sites, target the sites, and then retract, is required.

Figure 36A:
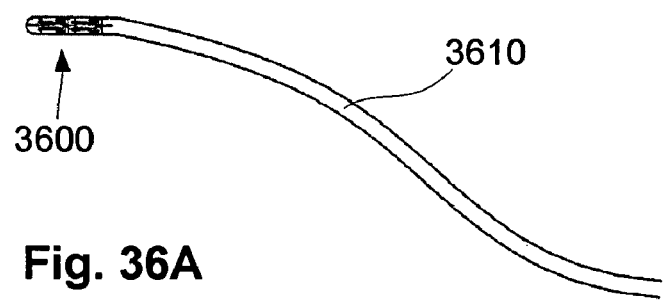
FIG. 36 is a schematic diagram of an example of a deployable patch structure for targeting the lower airway and lung.

As one example, FIG. 36 shows a deployable structure embodiment for targeting these sites.

In this example, the apparatus includes an application system 3600 mounted to a flexible structure, such as an arm, allowing the application system 3600 to be inserted into a passageway 3620, such as an airway, of the subject. To allow the application system 3600 to be guided to the correct location, the flexible structure may be in the form of a manipulable fibrescope, or the like.

Figure 36B:
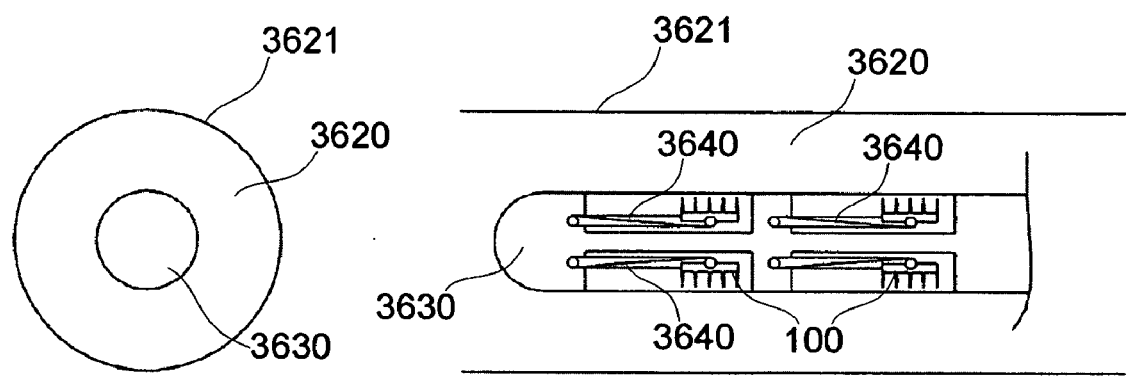
Figure 36C:
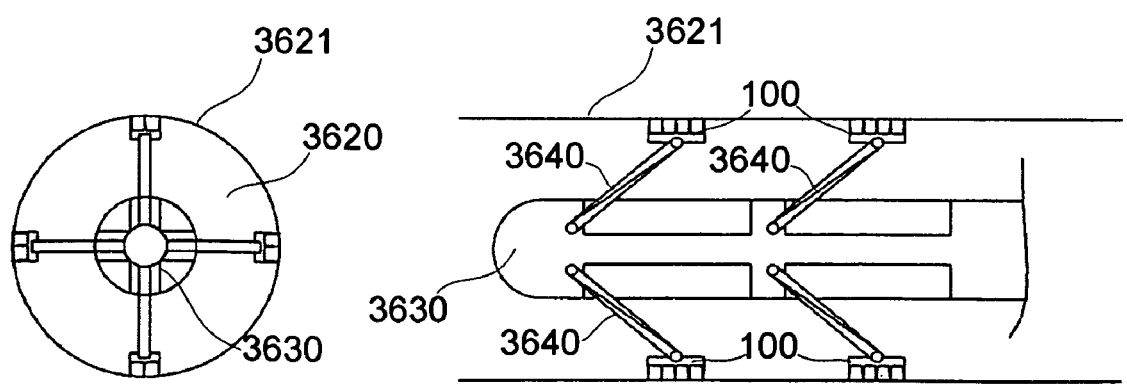

The application system includes a structure such as a body 3630, having a number of arms 3640 movably mounted thereto, to allow the arms to move between a retracted position shown in FIG. 36B and an extended position shown in FIG. 36C. In use, the arms 3640 are typically biased towards the extended position, and are retained in the retracted position, using a releasing mechanism, such as a clip or the like. It will be appreciated that this may be similar to the releasing means described above with respect to FIG. 35.

In any event, patches 100 are mounted to the arms, so that when the arms are released, the patches are urged against a surface 3621 of the passageway 3620, allowing the projections 110 provided on each patch to penetrate the surface 3621, and deliver material or stimulus to prospective targets.

In the example shown, the eight arms 3640 are provided in two sets of four, with the four arms in each set being circumferentially spaced around the body 3630, as shown in FIG. 36C.

The method of operation is as follows. The flexible structure (FIG. 36(*a*)) is guided through the throat to the site of interest. This device may be fitted with imaging/illumination systems to help guidance. FIG. 36(*b*) shows the system in location in a "retracted" position. The arms fitted with the patches are held in place against a spring load with pivot points. Then, by mechanical actuation, the arms are released (FIG. 36(*c*)), with the springs providing the force for location on the tissue.

The device does not need to be exactly centralised as the arms are self-locating. By tension with wires, the arms are retracted, and the device is removed through the throat.

In another embodiment, the arms are replaced by an inflatable structure (a "sock") fully coated by the micro-nanoprojections on the outside surface. When deflated, this sock would be held in a structure which would look similar to FIG. 36(*a*) on the outside. When in place, the sock would be inflated via a pressurised gas, locating on the tissue wall. This approach would be particularly useful where large surfaces need targeting, such as the lung. At the required time, the pressure is released with a valving arrangement and the sock collapses back into flexible targeting system and the device is removed.

9.4 Other Internal Tissues

Other internal organs or tissues (e.g. liver, kidney, heart) are not as readily accessed as those described above. Here, more invasive means are required to expose the site of interest before targeting. One example is a more compact "catheter" version of the described lower airway/lung targeting devices, reaching the site via keyhole routes.

Another embodiment is surgery to fully open the site before application with the patch.

9.5 In-Vitro Sites

The micro-nanoprojections may be fitted to patches for in-vitro targeting, allowing a high-throughput targeting of cells. In one example, larger patches with thousands and perhaps millions of projections could be mechanically lowered onto cell monolayers, and then removed, similar to a mechanical "press" arrangement. This could, for instance, allow a mass transfection of cells, in-vitro.

As another variation, cells are dynamically moving in a shallow fluid stream. As these cells move, they pass below large plates with thousands, and perhaps millions of micro-nanoprojections. These plates pressing into this cell layer repeatedly, in a synchronised manner so that each pressing cycle targets the appropriate batch of cells.

The invention claimed is:

1. A device for delivery of material or stimulus to targets within a body to produce a desired response, the targets being at least one of cells of interest, cell organelles of interest and cell nuclei of interest, the device including a number of projections for penetrating a body surface, and wherein:
   a) the projections include a targeting section for delivering the material or stimulus to the targets to thereby cause the desired response and a support section for supporting the targeting section;
   b) the number of projections is selected to deliver material or stimulus to a number of targets that is at least sufficient to produce the desired response, the number of projections being at least 500;
   c) a spacing between projections is at least partially determined based on an arrangement of the targets within the body, the spacing between at least some of the projections being selected to be greater than a diameter of a target of interest; and
   d) at least part of at least some of the projections are coated with a non-liquid material.

2. A device according to claim 1, wherein the number of projections is selected by:
   a) determining a likelihood of a projection targeting at least one of the targets;
   b) determining a number of targets to be targeted; and,
   c) determining the number of projections using the determined likelihood and the determined number of targets.

3. A device according to claim 2, wherein the likelihood of a projection targeting a target of interest is $P_{contact}$ and is at least partially based on:

$$P_{contact} = \frac{V_{tar}}{V_{layer}}$$

where:
   $V_{layer}$ is the volume of the layer containing targets,
   $V_{tar}$ is the volume including the target of interest to which material or stimulus can be delivered.

4. A device according to claim 2, wherein the number of targets to be targeted depends on the number of targets that need to be transfected to produce the desired response.

5. A device according to claim 4, wherein the number of targets to be targeted is at least one of:
   a) at least 10;
   b) at least 100;
   c) at least 1000;
   d) at least 10000;
   e) at least 100000;
   f) at least 1000000; and,
   g) at least 10000000.

6. A device according to claim 1, wherein the number of projections is at least one of:
   a) at least 1000;
   b) at least 10000;
   c) at least 100000;
   d) at least 1000000; and,
   e) at least 10000000.

7. A device according to claim 1, wherein a maximum number of projections is based on at least one of:
   a) the total surface area of the target site available;
   b) a minimum projection spacing (S); and,
   c) an upper limit in active material or stimulus to be delivered.

8. A device according to claim 1, wherein the projection spacing is based at least partially on at least one of:
   a) a size of the targets of interest; and,
   b) a spacing between the targets of interest.

9. A device according to claim 1, wherein the spacing between at least some of the projections is selected to avoid multiple projections targeting a single target of interest.

10. A device according to claim 1, wherein the spacing between at least some of the projections is selected to be approximately equal to the spacing between the targets of interest.

11. A device according to claim 1, wherein the projection spacing (S) is at least one of:
   a) $1 \ \mu m \leq S \leq 10000 \ \mu m$; and,
   b) $10 \ \mu m \leq S \leq 200 \ \mu m$.

12. A device according to claim 1, wherein projection dimensions are based at least partially on an arrangement of targets within the body.

13. A device according to claim 12, wherein at least some of the projections have a diameter of at least one of:
 a) less than the size of targets; and,
 b) substantially equal to the size of targets within the targets.

14. A device according to claim 12, wherein at least some of the projections have a projection length at least partially based on a depth of the targets below a surface of the body against which the device is to be applied in use.

15. A device according to claim 12, wherein at least some of the projections within a targeting configuration have different dimensions.

16. A device according to claim 1, wherein the targeting section has a diameter of less than at least one of:
 a) 5 µm;
 b) 2 µm;
 c) 1 µm; and,
 d) 0.5 µm.

17. A device according to claim 1, wherein a length for the targeting section is at least:
 a) less than 0.5 µm;
 b) less than 1.0 µm;
 c) less than 2.0 µm; and,
 d) less than 20 µm.

18. A device according to claim 1, wherein a length for the support section is at least partially based on a depth of the targets below a surface of the body against which the device is to be applied in use.

19. A device according to claim 18, wherein the length for the support section is at least partially determined in accordance with properties of a surface of the body against which the device is to be applied in use.

20. A device according to claim 19, wherein a length for the support section is at least one of:
 a) for epidermal delivery <200 µm;
 b) for dermal cell delivery <1000 µm;
 c) for mucosal delivery >100 µm;
 d) for delivery to basal cells in the epithelium of the mucosa 600-800 µm; and,
 e) for lung delivery of the order of 100 µm.

21. A device according to claim 19, wherein the support section penetrates the body surface in use to thereby position the targeting section of at least some of the projections substantially at the depth of the targets below the surface of the body.

22. A device according to claim 1, wherein at least one of a support section length and the number of projections is at least partially based on a likelihood of a projection penetrating the targets at a defined depth ($P_{depth}$):

$$P_{depth} = \int_{B-Q\sigma}^{T+B-Q\sigma} \frac{dx}{\sigma\sqrt{2\pi}} e^{-(\frac{x-D}{\sigma})^2}$$

where:
 σ is the standard deviation from a mean location, accounting for the skin surface undulations;
 D is a distance of the targets below a surface of the body against which the device is to be applied in use;
 Q is a number of standard deviations from a mean level of the surface of the body at which the device comes to rest in use;
 B is a length of the support section; and,
 T is a length of a targeting section.

23. A device according to claim 1, wherein the length of the targeting section is greater than the target dimension.

24. A device according to claim 1, wherein the projections are solid.

25. A device according to claim 1, wherein the projections are non-porous and non-hollow.

26. A device according to claim 1, wherein at least part of at least some of the projections are coated with a bioactive material.

27. A device according to claim 1, wherein at least part of a targeting section of at least some of the projections are coated.

28. A device according to claim 1, wherein the coating is at least one of:
 a) nanoparticles;
 b) a nucleic acid or protein;
 c) an antigen, allergen, or adjuvant;
 d) parasites, bacteria, viruses, or virus-like particles;
 e) quantum dots, SERS tags, raman tags or other nanobiosensors;
 f) metals or metallic compounds; and,
 g) molecules, elements or compounds.

29. A device according to claim 1, wherein each of the number of projections is for penetrating the body surface.

30. A device according to claim 1, wherein the targets of interest are at least one of antigen-presenting cells, antigen-presenting cell organelles and antigen-presenting cell nuclei.

31. A device according to claim 1, wherein the desired response is at least one of an immune response and a tolerogenic response.

32. A device according to claim 1, wherein the device is a patch including a base and an array of projections extending substantially perpendicularly from the base, each projection including a tip for penetrating the body surface.

33. A device according to claim 1, wherein at least some of the projections perturb the targets in use to thereby induce bystander responses.

34. Apparatus for delivery of material or stimulus to targets of interest within a body to produce a desired response, the targets being at least one of cells of interest, cell organelles of interest and cell nuclei of interest, the apparatus including:
 a) a structure;
 b) a plurality of projections movably mounted to the structure for penetrating a body surface;
 c) an actuator for selectively releasing the plurality of projections mounted on the movable structure from a retracted position such that upon contact with the body surface the plurality of projections enter the body, the actuator including:
  i) a spring coupled to the structure and the at least one patch;
  ii) a releasing means for releasing the spring, to thereby release the plurality of projections from the retracted position; and,
  iii) a number of arms, each arm being coupled to a respective spring and including a first end pivotally mounted to the structure and a second end coupled to a respective plurality of projections, and wherein activation of the releasing means causes each of the arms to be released from a retracted position to thereby cause projections on the respective patch to enter the body.

35. Apparatus according to claim 34, wherein the plurality of projections are provided on a patch.

36. Apparatus according to claim 34, wherein the releasing means is a tensioned string for holding the spring in compression.

37. Apparatus according to claim 34, wherein the releasing means is manually operated.

38. Apparatus according to claim 34, wherein the arms are circumferentially spaced around a part of the structure.

39. Apparatus according to claim 34, wherein the structure is flexible structure allowing the structure to be guided to a desired location within the body.

40. Apparatus according to claim 34, wherein the releasing means includes an inflatable structure coated with the plurality of projections.

41. Apparatus according to claim 34, wherein:
   a) the number of projections is selected to produce a desired response, the number being at least 500; and,
   b) a spacing between projections is at least partially determined based on an arrangement of the targets within the body.

42. A device for delivery of material or stimulus to targets within a body to produce a desired response, the targets being at least one of cells of interest, cell organelles of interest and cell nuclei of interest, the device including a number of projections for penetrating a body surface, and wherein:
   a) the number of projections is selected to deliver material or stimulus to a number of targets that is at least sufficient to produce the desired response, the number of projections being at least 500;
   b) a spacing between projections is at least partially determined based on an arrangement of the targets within the body, the spacing between at least some of the projections being selected to be greater than a diameter of a target of interest; and,
   c) the device includes at least some uncoated projections to thereby stimulate or perturb the targets in use.

43. A device for delivery of material or stimulus to targets within a body to produce a desired response, the targets being at least one of cells of interest, cell organelles of interest and cell nuclei of interest, the device including a number of projections for penetrating a body surface, and wherein:
   a) at least part of at least some of the projections are coated with a non-liquid bioactive material for delivery to the targets, to thereby cause the desired response;
   b) the number of projections is selected to deliver material or stimulus to a number of targets that is at least sufficient to produce the desired response, the number of projections being at least 500; and
   c) a spacing between projections is at least partially determined based on an arrangement of the targets within the body, the spacing between at least some of the projections being selected to be greater than a diameter of a target of interest.

44. A device according to claim 43, wherein at least part of at least some of the projections are coated with two or more different non-liquid materials on the same projection.

45. A device according to claim 43, wherein at least some of the targets are at least one of antigen-presenting cells, antigen-presenting cell organelles and antigen-presenting cell nuclei, and the desired response being at least one of an immune response and a tolerogenic response.

46. A device according to claim 43, wherein at least some of the targets are at least one of:
   a) macrophages;
   b) monocytes;
   c) B lymphocytes;
   d) monocytic-granulocytic-DC precursors;
   e) marginal zone Kupffer cells;
   f) microglia;
   g) T cells;
   h) Langerhans cells;
   i) dendritic cells;
   j) activated T lymphocytes;
   k) eosinophils;
   l) keratinocytes;
   m) astrocytes;
   n) follicular cells;
   o) microglial cells;
   p) thymic cortical cells;
   q) endothelial cells;
   r) Schwann cells;
   s) retinal pigment epithelial cells;
   t) myoblasts;
   u) vascular smooth muscle cells;
   v) chondrocytes;
   w) enterocytes;
   x) thymocytes;
   y) kidney tubule cells; and,
   z) fibroblasts.

47. A device for delivery of material or stimulus to targets within a body to produce a desired response, the targets being at least one of cells of interest, cell organelles of interest and cell nuclei of interest, the device including a number of projections for penetrating a body surface, and wherein:
   a) the number of projections is selected to deliver material or stimulus to a number of targets that is at least sufficient to produce the desired response, the number of projections being at least 500;
   b) a spacing between projections is at least partially determined based on an arrangement of the targets within the body, the spacing between at least some of the projections being selected to be greater than a diameter of a target of interest; and,
   c) at least part of at least some of the projections dissolve upon penetrating the body surface.

48. A device according to claim 47, wherein a bioactive material is releasably incorporated into the projections to thereby allow the bioactive material to be delivered to the targets as the at least part of at least some of the projections dissolve.

49. A device for delivery of material or stimulus to targets within a body to produce a desired response, the targets being at least one of cells of interest, cell organelles of interest and cell nuclei of interest, the device including a number of projections for penetrating a body surface, and wherein:
   a) the number of projections is selected to deliver material or stimulus to a number of targets that is at least sufficient to produce the desired response, the number of projections being at least 500;
   b) a spacing between projections is at least partially determined based on an arrangement of the targets within the body, the spacing between at least some of the projections being selected to be greater than a diameter of a target of interest; and,
   c) at least some of the projections have dimensions that are different to corresponding dimensions of at least some other projections of the device.

50. A device for delivery of material or stimulus to targets within a body to produce a desired response, the targets being at least one of cells of interest, cell organelles of interest and cell nuclei of interest, the device including a number of projections for penetrating a body surface, and wherein:
   a) the projections include a targeting section for delivering the material or stimulus to the targets to thereby cause the desired response and a support section for supporting the targeting section;
   b) the number of projections is selected to deliver material or stimulus to a number of targets that is at least sufficient to produce the desired response, the number of projections being at least 500;
c) a spacing between projections is at least partially determined based on an arrangement of the targets within the body, the spacing between at least some of the projections being selected to be greater than a diameter of a target of interest;
d) projection dimensions are based at least partially on an arrangement of targets within the body; and,
e) at least some of the projections within a targeting configuration have different dimensions.

51. A device for delivery of material or stimulus to targets within a body to produce a desired response, the targets being at least one of cells of interest, cell organelles of interest and cell nuclei of interest, the device including a number of projections for penetrating a body surface, and wherein:
   a) the projections include a targeting section for delivering the material or stimulus to the targets to thereby cause the desired response and a support section for supporting the targeting section;
   b) the number of projections is selected to deliver material or stimulus to a number of targets that is at least sufficient to produce the desired response, the number of projections being at least 500;
   c) a spacing between projections is at least partially determined based on an arrangement of the targets within the body, the spacing between at least some of the projections being selected to be greater than a diameter of a target of interest;
   d) at least some of the projections perturb the targets in use to thereby induce bystander responses.

52. Apparatus for delivery of material or stimulus to targets of interest within a body to produce a desired response, the targets being at least one of cells of interest, cell organelles of interest and cell nuclei of interest, the apparatus including:
   a) a structure;
   b) a plurality of projections movably mounted to the structure for penetrating a body surface; and
   c) an actuator for selectively releasing the plurality of projections mounted on the movable structure from a retracted position such that upon contact with the body surface the plurality of projections enter the body, the actuator including a releasing means for releasing the plurality of projections from the retracted position, the releasing means including an inflatable structure coated with the plurality of projections.

* * * * *